(12) United States Patent
Courtney et al.

(10) Patent No.: US 8,460,195 B2
(45) Date of Patent: Jun. 11, 2013

(54) SCANNING MECHANISMS FOR IMAGING PROBE

(75) Inventors: Brian Courtney, Toronto (CA); Nigel Robert Munce, Toronto (CA); Amandeep Singh Thind, Toronto (CA); Victor Xiao Dong Yang, Toronto (CA); Francis Stuart Foster, Toronto (CA); Alan Soong, Etobicoke (CA); Brian Heng Li, Kitchener (CA)

(73) Assignee: Sunnybrook Health Sciences Centre, Toronto, ON (CA)

( * ) Notice: Subject to any disclaimer, the term of this patent is extended or adjusted under 35 U.S.C. 154(b) by 665 days.

(21) Appl. No.: 12/385,014

(22) Filed: Mar. 27, 2009

(65) Prior Publication Data

US 2009/0264768 A1 Oct. 22, 2009

Related U.S. Application Data

(63) Continuation-in-part of application No. 12/010,206, filed on Jan. 22, 2008, now Pat. No. 8,214,010.

(60) Provisional application No. 60/881,169, filed on Jan. 19, 2007.

(51) Int. Cl.
*A61B 8/14* (2006.01)
(52) U.S. Cl.
USPC ............ 600/463; 600/459; 600/462; 600/466
(58) Field of Classification Search
USPC ................. 600/137, 160, 178, 459, 462–463, 600/466, 407, 476, 478, 427, 473
See application file for complete search history.

(56) References Cited

U.S. PATENT DOCUMENTS

| 4,697,577 A | 10/1987 | Forkner |
|---|---|---|
| 4,794,931 A | 1/1989 | Yock |

(Continued)

FOREIGN PATENT DOCUMENTS

| JP | 2005224399 | 8/2005 |
|---|---|---|
| WO | 9616600 | 6/1996 |

(Continued)

OTHER PUBLICATIONS

Hoff, Harm ten. "Scanning mechanisms for intravascular ultrasound imaging: a flexible approach", Diss. Erasmus University, Rotterdam. 1993. Print: 117-151, 195-199.

(Continued)

*Primary Examiner* — Unsu Jung
*Assistant Examiner* — Daniel Huntley
(74) *Attorney, Agent, or Firm* — Hill & Schumacher; Lynn C. Schumacher; Stephen W. Leonard

(57) ABSTRACT

The present invention provides scanning mechanisms for imaging probes using for imaging mammalian tissues and structures using high resolution imaging, including high frequency ultrasound and/or optical coherence tomography. The imaging probes include adjustable rotational drive mechanism for imparting rotational motion to an imaging assembly containing either optical or ultrasound transducers which emit energy into the surrounding area. The imaging assembly includes a scanning mechanism including a movable member configured to deliver the energy beam along a path out of said elongate hollow shaft at a variable angle with respect to said longitudinal axis to give forward and side viewing capability of the imaging assembly. The movable member is mounted in such a way that the variable angle is a function of the angular velocity of the imaging assembly.

37 Claims, 42 Drawing Sheets

U.S. PATENT DOCUMENTS

| | | | |
|---|---|---|---|
| 4,869,258 | A | 9/1989 | Hetz |
| 4,895,158 | A | 1/1990 | Kawabuchi et al. |
| 4,951,677 | A | 8/1990 | Crowley |
| 4,972,839 | A | 11/1990 | Angelsen |
| 5,152,293 | A | 10/1992 | Vonesh et al. |
| 5,373,845 | A | 12/1994 | Gardineer |
| 5,373,849 | A | 12/1994 | Maroney |
| 5,375,602 | A | 12/1994 | Lancee |
| 5,379,772 | A | 1/1995 | Imran |
| 5,427,107 | A | 6/1995 | Milo |
| 5,429,136 | A | 7/1995 | Milo |
| 5,465,724 | A | 11/1995 | Sliwa, Jr. et al. |
| 5,469,853 | A | 11/1995 | Law et al. |
| 5,485,845 | A | 1/1996 | Verdonk et al. |
| 5,505,088 | A | 4/1996 | Chandraratna et al. |
| 5,606,975 | A | 3/1997 | Liang |
| 5,647,367 | A | 7/1997 | Lum et al. |
| 5,651,366 | A | 7/1997 | Liang |
| 5,682,895 | A | 11/1997 | Ishiguro |
| 5,718,231 | A | 2/1998 | Dewhurst |
| 5,779,643 | A | 7/1998 | Lum et al. |
| 5,817,021 | A | 10/1998 | Reichenberger |
| 6,035,229 | A | 3/2000 | Silverstein |
| 6,110,121 | A | 8/2000 | Lenker |
| 6,134,003 | A | 10/2000 | Tearney et al. |
| 6,171,247 | B1 | 1/2001 | Seward et al. |
| 6,178,346 | B1 | 1/2001 | Amundson |
| 6,200,268 | B1 | 3/2001 | Vince |
| 6,264,610 | B1 | 7/2001 | Zhu |
| 6,315,732 | B1 | 11/2001 | Suorsa |
| 6,390,978 | B1 | 5/2002 | Irion et al. |
| 6,445,939 | B1 | 9/2002 | Swanson et al. |
| 6,450,964 | B1 | 9/2002 | Wedler |
| 6,485,413 | B1 | 11/2002 | Boppart |
| 6,546,272 | B1 * | 4/2003 | MacKinnon et al. ......... 600/407 |
| 6,583,914 | B1 | 6/2003 | Muller et al. |
| 6,592,526 | B1 | 7/2003 | Lenker |
| 6,626,834 | B2 | 9/2003 | Dunne et al. |
| 6,690,958 | B1 | 2/2004 | Walker et al. |
| 6,949,072 | B2 | 9/2005 | Furnish et al. |
| 6,975,898 | B2 | 12/2005 | Seibel |
| 7,077,808 | B2 | 7/2006 | Couvillon |
| 7,123,175 | B2 * | 10/2006 | Katakura et al. ............. 341/112 |
| 7,289,842 | B2 | 10/2007 | Maschke |
| 7,366,376 | B2 | 4/2008 | Shishkov et al. |
| 7,761,139 | B2 | 7/2010 | Tearney et al. |
| 2003/0023019 | A1 | 1/2003 | Kondou et al. |
| 2005/0020926 | A1 | 1/2005 | Wiklof et al. |
| 2005/0101859 | A1 * | 5/2005 | Maschke ...................... 600/427 |
| 2006/0116571 | A1 | 6/2006 | Maschke et al. |
| 2007/0016062 | A1 | 1/2007 | Park et al. |
| 2007/0161893 | A1 | 7/2007 | Milner et al. |
| 2009/0203991 | A1 | 8/2009 | Papaioannou et al. |

FOREIGN PATENT DOCUMENTS

| | | |
|---|---|---|
| WO | 9732182 | 9/1997 |
| WO | 03/067526 | 8/2003 |
| WO | 2004/010856 | 2/2004 |
| WO | 2004/096049 | 11/2004 |
| WO | 2006/121851 | 5/2006 |
| WO | 2007123518 A1 | 11/2007 |

OTHER PUBLICATIONS

Caplan JD et al, "Near-infrared spectroscopy for the detection of vulnerable coronary artery plaques". J Am Coll Cardiol. Apr. 18, 2006:47(8Suppl):C92-C96.

de Korte et al., "Identification of atherosclerotic plaque components with intravascular ultrasound elastography in vivo: A yucatan pig study", Circulation, 2002; 105, 1627-1630.

Goertz et al., "Contrast harmonic intravascular ultrasound: A feasibilty study for vasa vasorum imaging", Investigative Radiology, vol. 41, No. 8, Aug. 2008, pp. 631-638.

Picano et al, "Angle dependence of ultrasonic backscatter in arterial tissues: a study in vitro", Circulation, 1985, 72; 572-576.

Mao et al, "Graded-index fiber lens proposed for ultrasmall probes used in biomedical imaging", Applied Optics, vol. 46, No. 23, Aug. 10, 2007, pp. 5887-5894.

Motz et al., "In vivo raman spectral pathology of human atherosclerosis and vulnerable plaque", J. Biomed Optics, vol. 11(2), Mar./Apr. 2006, pp. 021003-1-021003-9.

Funovics et al., "Catheter-based in vivo imaging of enzyme activity and gene expression: feasibility study in mice", Radiology, Jun. 2004, 231; pp. 659-666.

Brezinski et al. "Assessing atherosclerotic plaque morphology: comparison of optical coherence tomography and high frequency intravascular ultrasound." BMJ Heart. May 1997, p. 397-406, vol. 77(5), http://80-gateway1.ovid.com.lane-proxy.stanford.org/ovidweb.cgi.

Nair et al. "Coronary Plaque Classification With Intravascular Ultrasound Radiofrequency Data Analysis." Circulation. 2002; 106; 2200-2206.

Kubo et al. "Assessment of Culprit Lesion Morphology in Acute Myocardial Infarction." J. Amer. Col. Cardiology. 2007, vol. 50, No. 10, p. 933-939.

Klingensmith et al. "Evaluation of Three-Dimensional Segmentation Algorithms for the Identification of Luminal and Medial-Adventital Borders in Intravascular Ultrasound Images." IEEE Transactions on Medical Imaging. Oct. 2000, vol. 19, No. 10. p. 996-1011.

Daniels et al. "Sonoluminescence in Water and Agar Gels During Irradiation with 0.75 MHz Continuous-Wave Ultrasound." Ultrasound in Med. & Biol. 1991, vol. 17, No. 3, p. 297-308.

Kawasaki et al. "Diagnostic Accuracy of Optical Coherence Tomography and Integrated Backscatter Intravascular Ultrasound Images for Tissue Characterization of Human Coronary Plaques." J. Amer. Col. Cardiology. 2006, vol. 48, No. 1, p. 81-88.

* cited by examiner

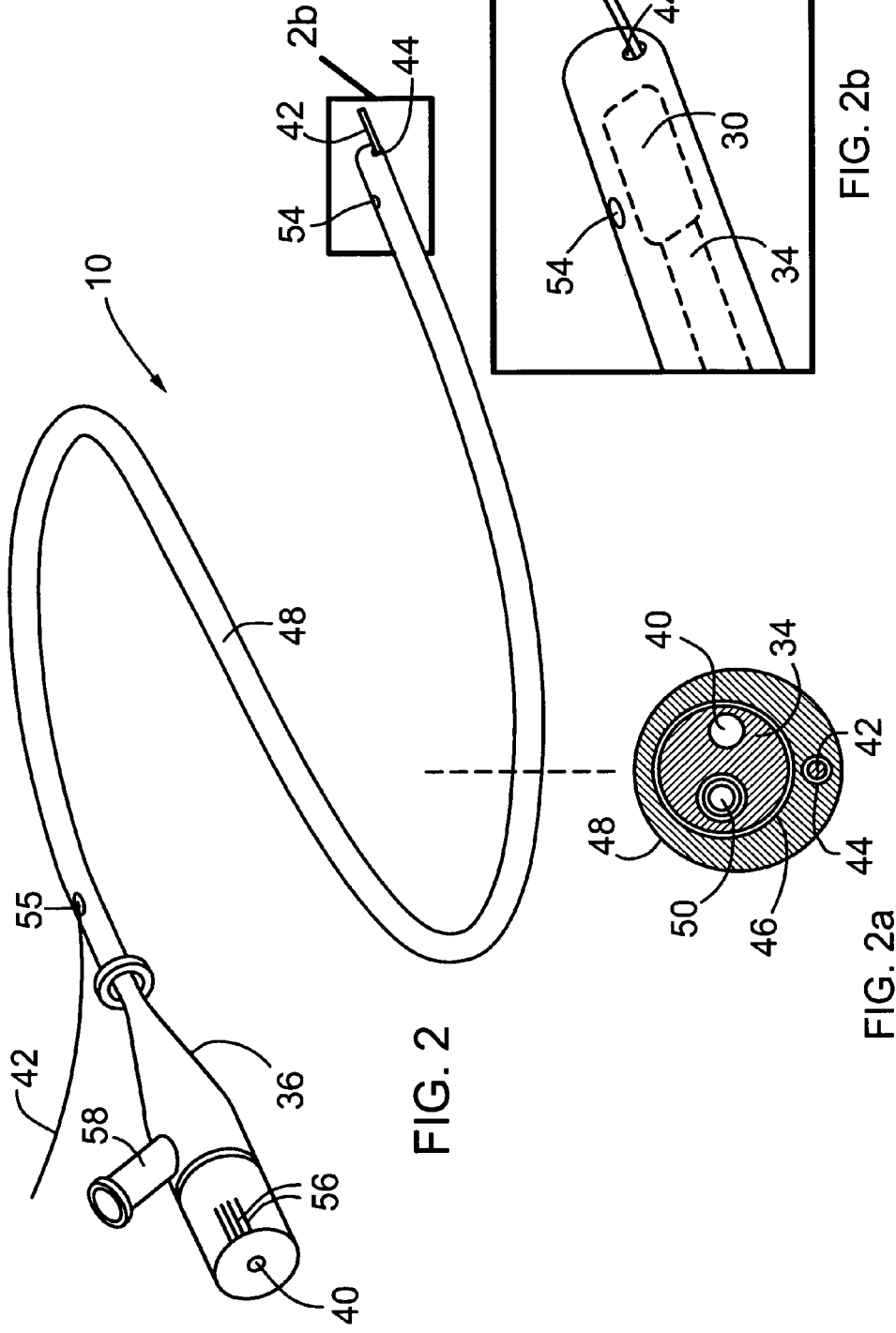

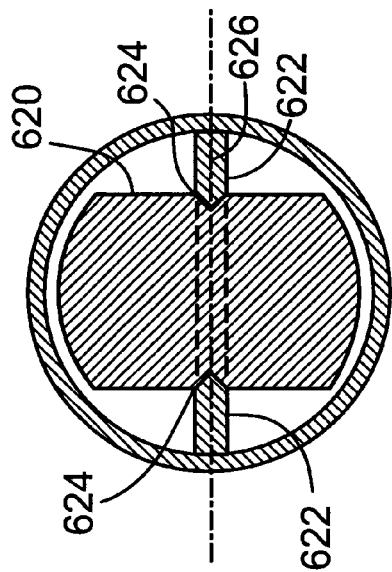
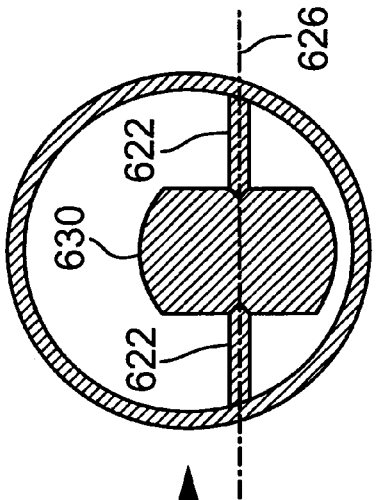
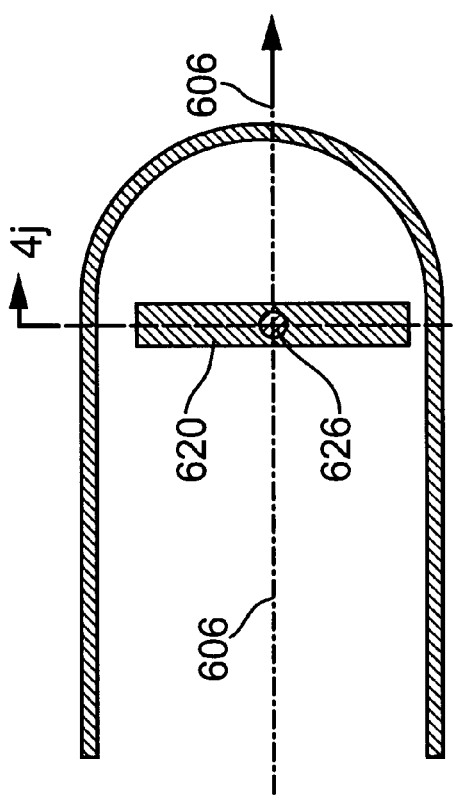
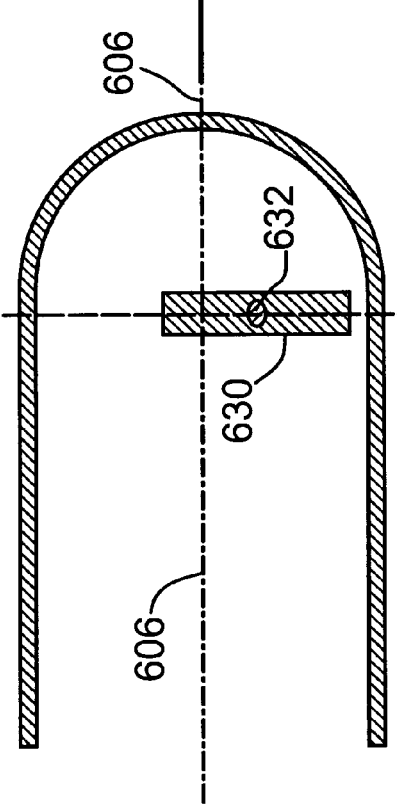

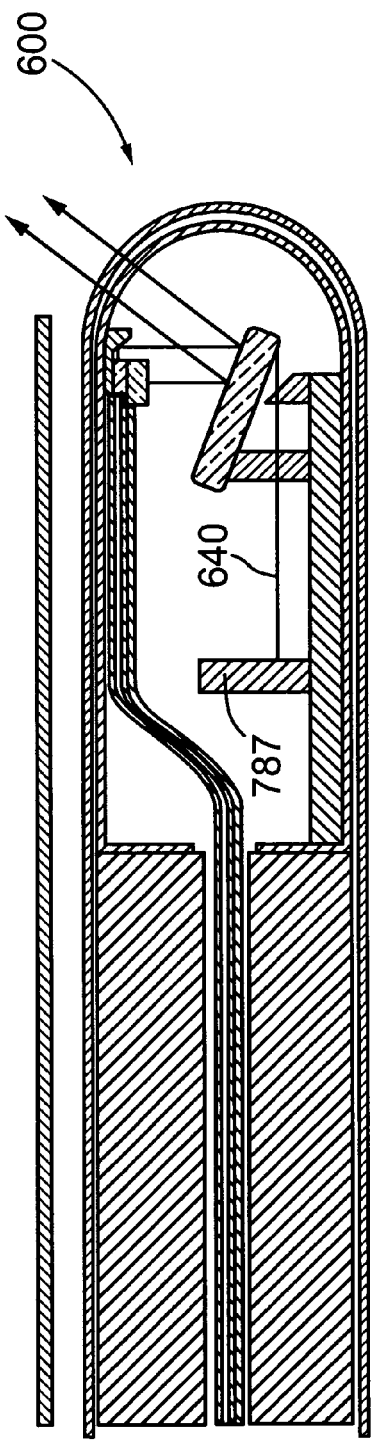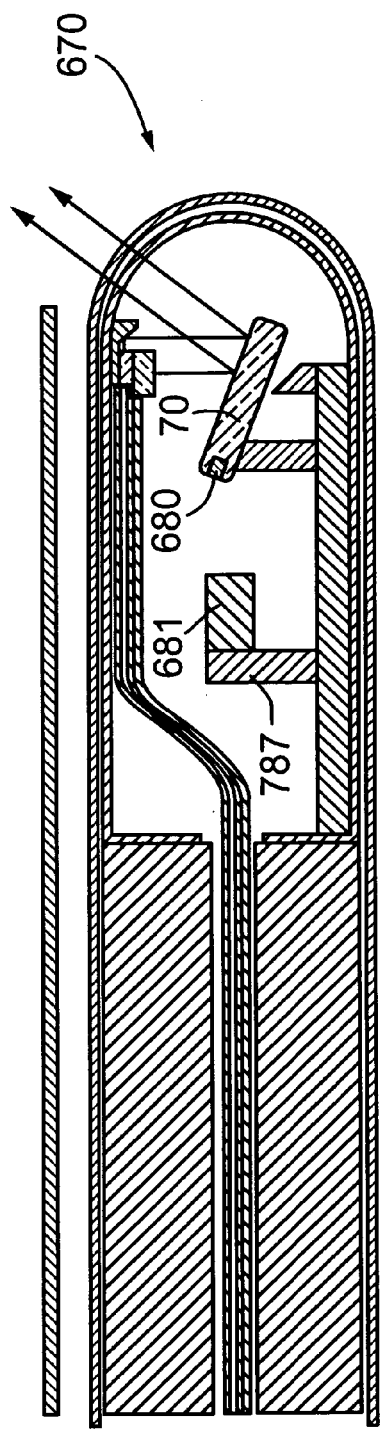
FIG. 5e
FIG. 5f

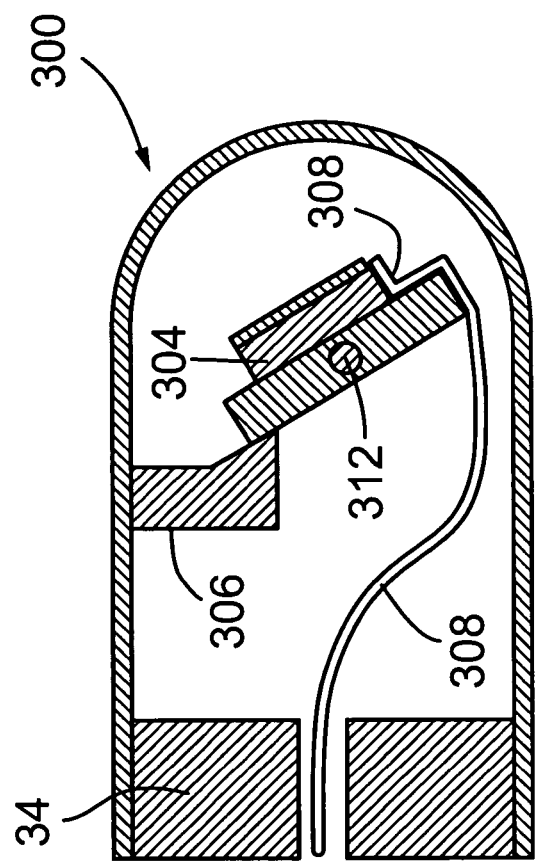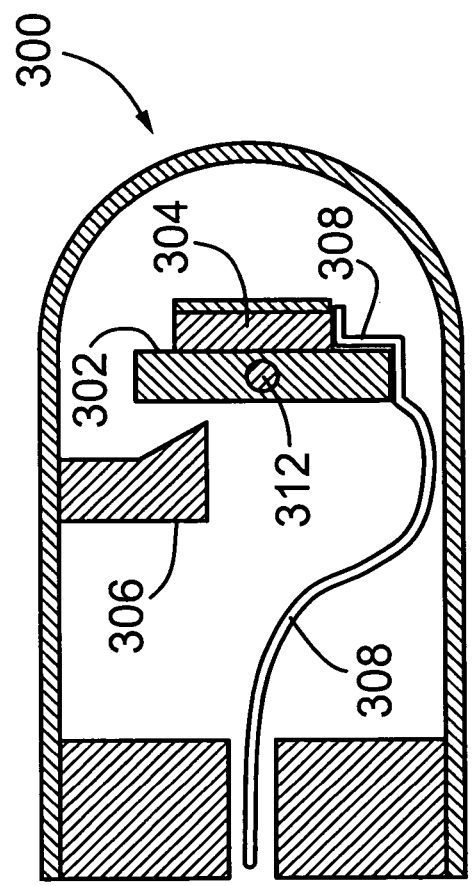

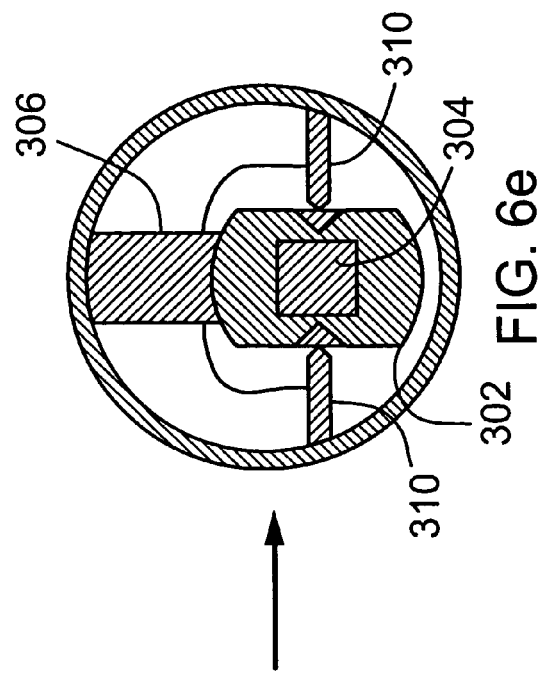
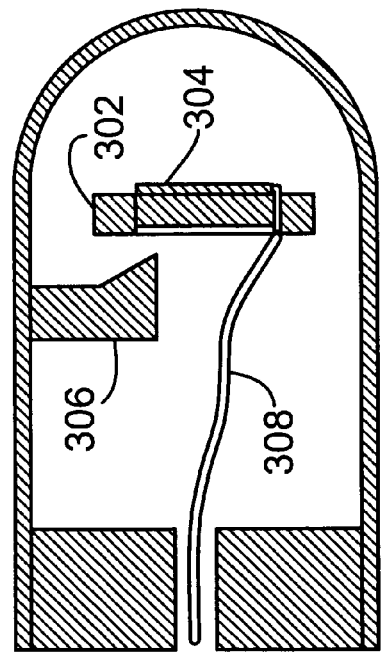
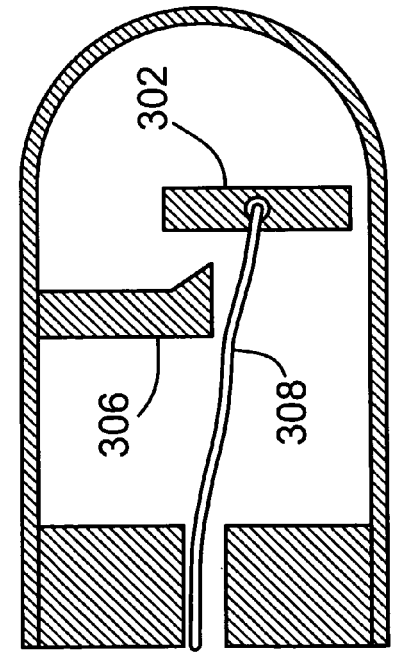

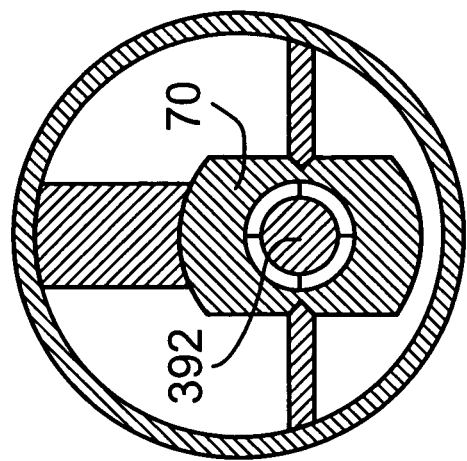
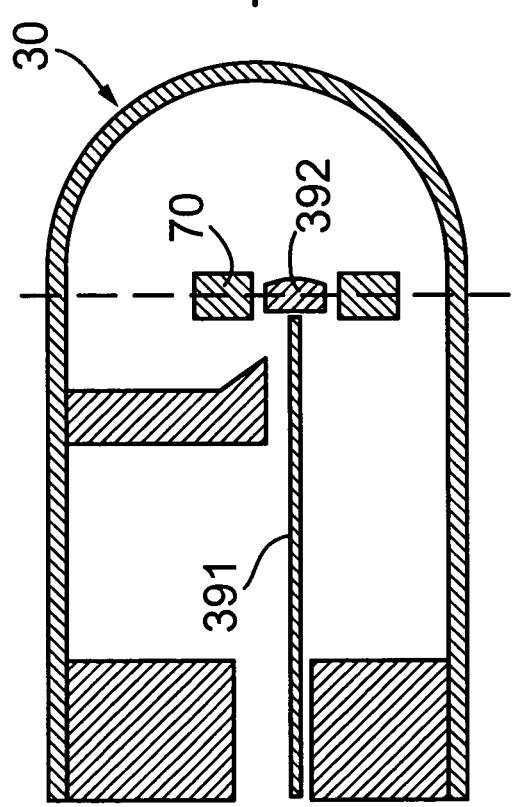
FIG. 6g
FIG. 6f

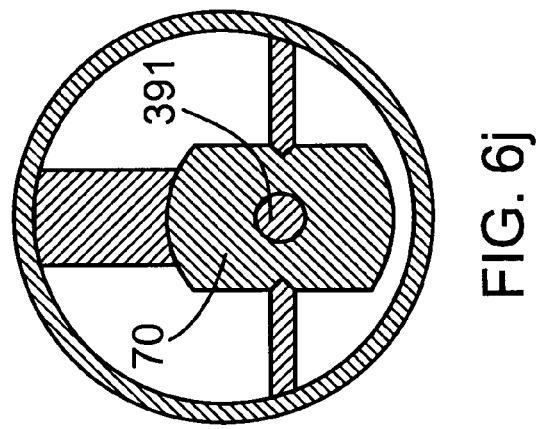
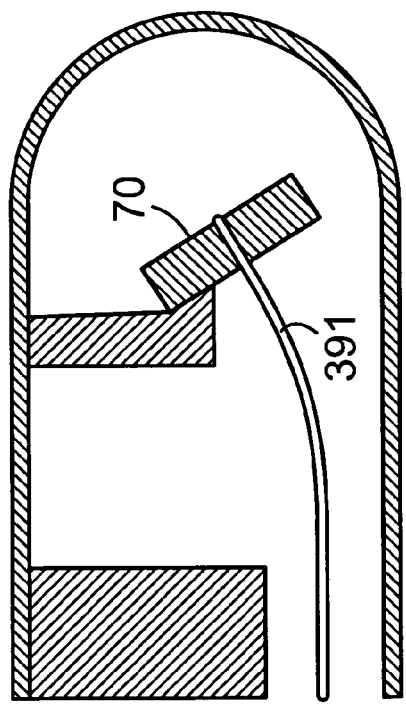
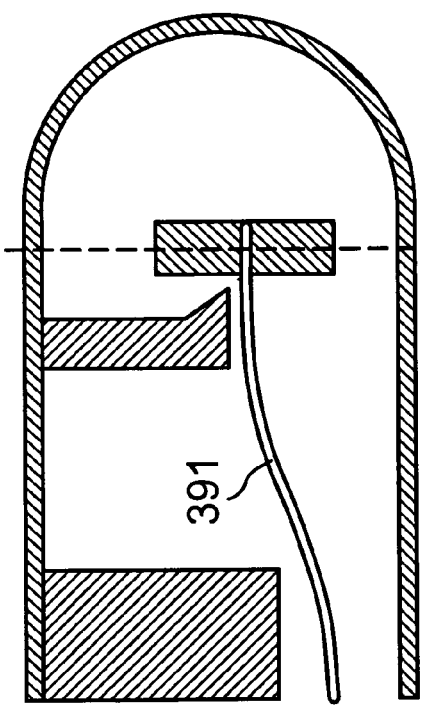

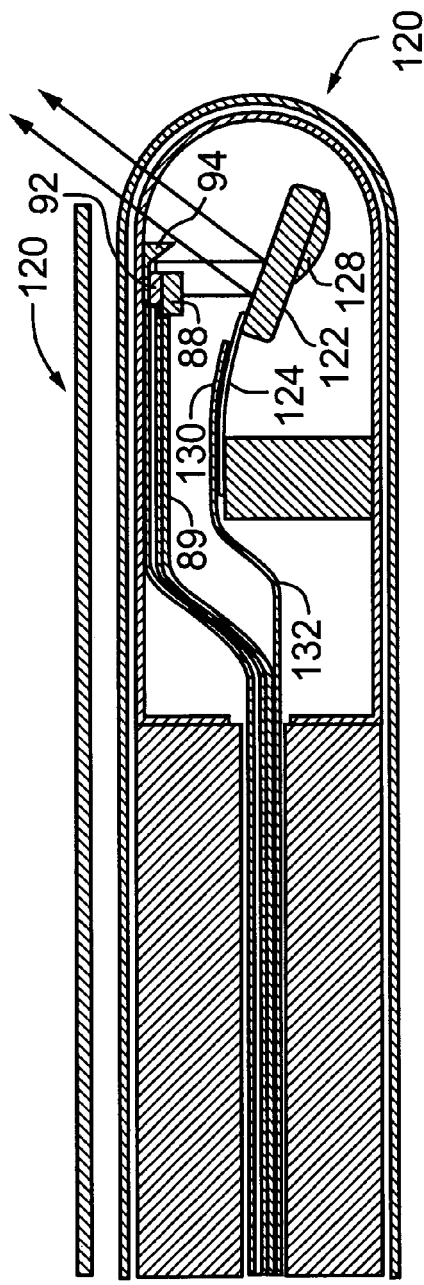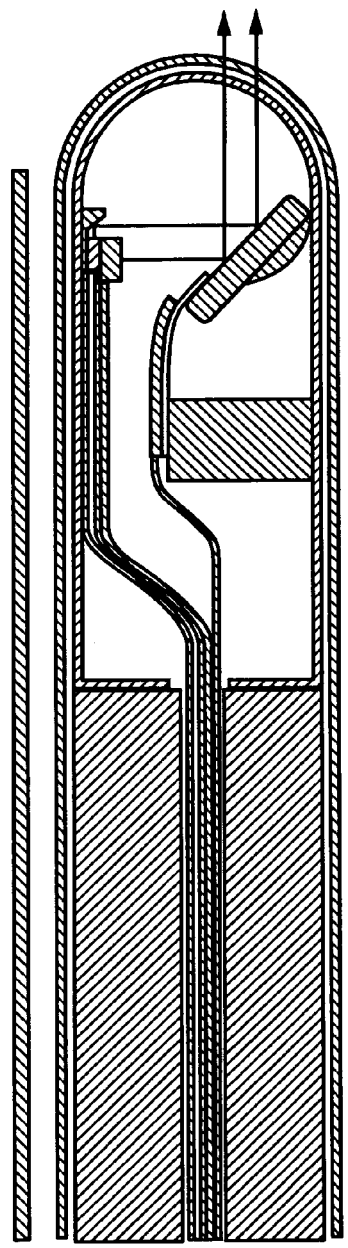
FIG. 10a
FIG. 10b

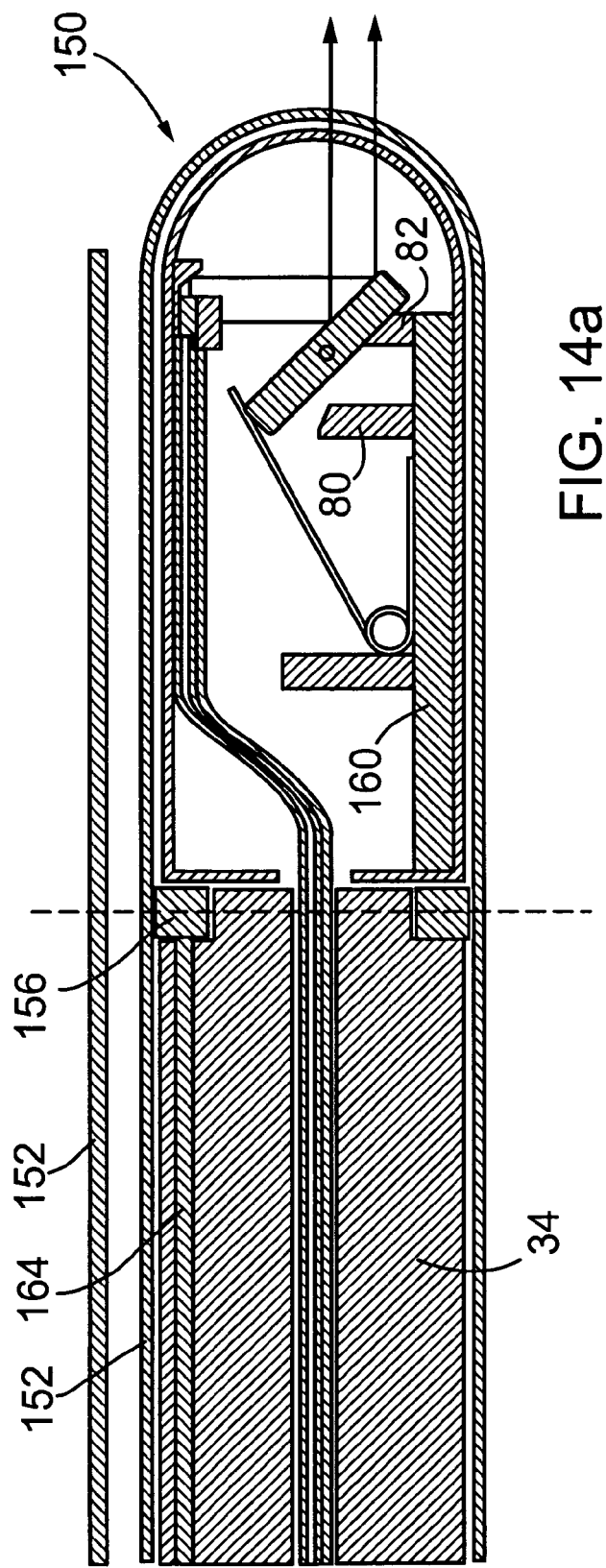
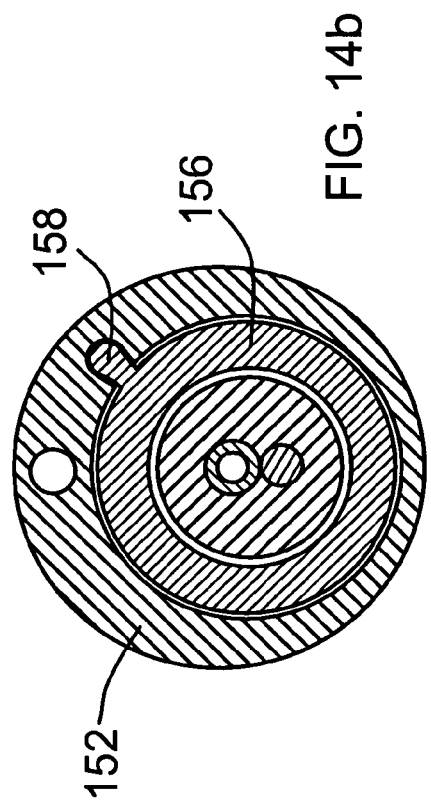
FIG. 14a
FIG. 14b

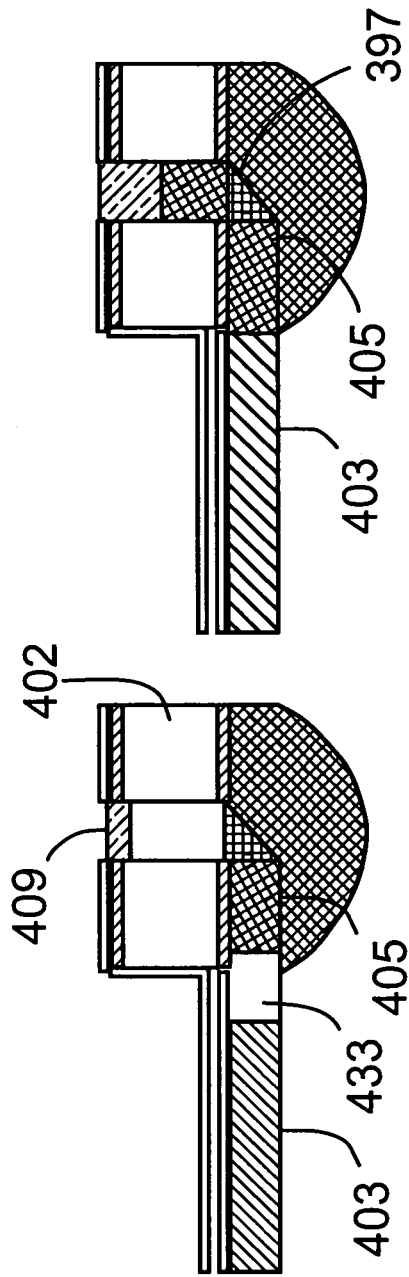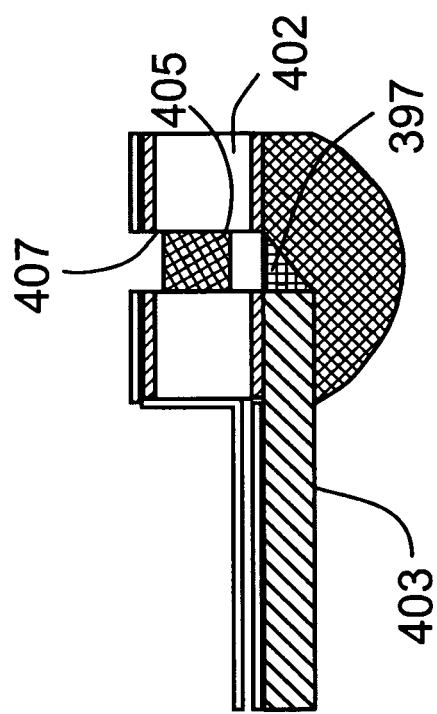
FIG. 17f
FIG. 17g
FIG. 17h

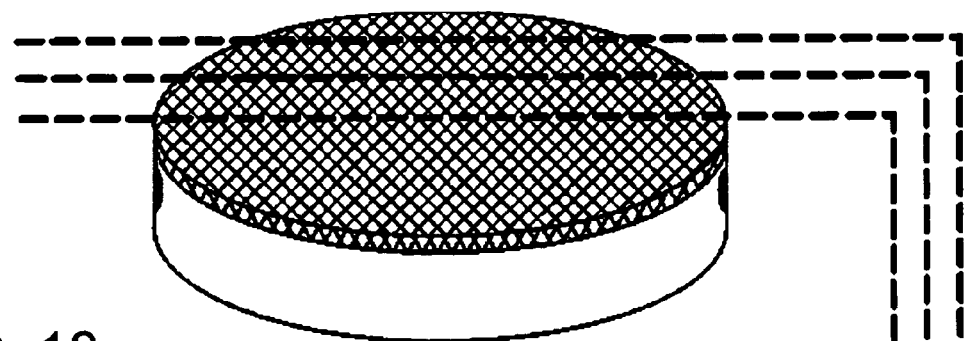
FIG. 18a
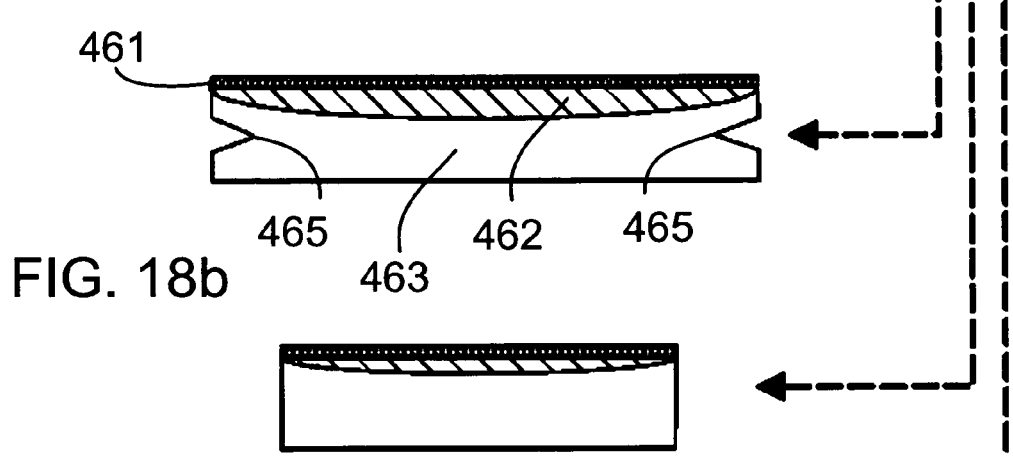
FIG. 18b
FIG. 18c
FIG. 18d

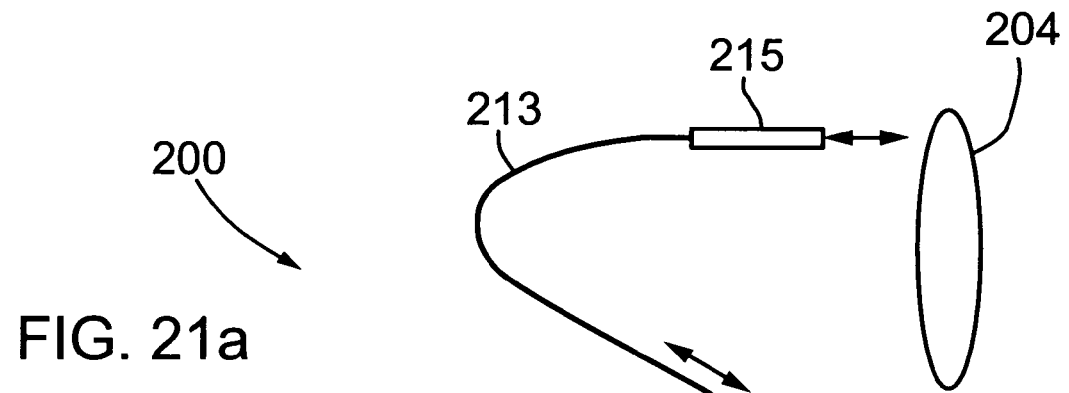
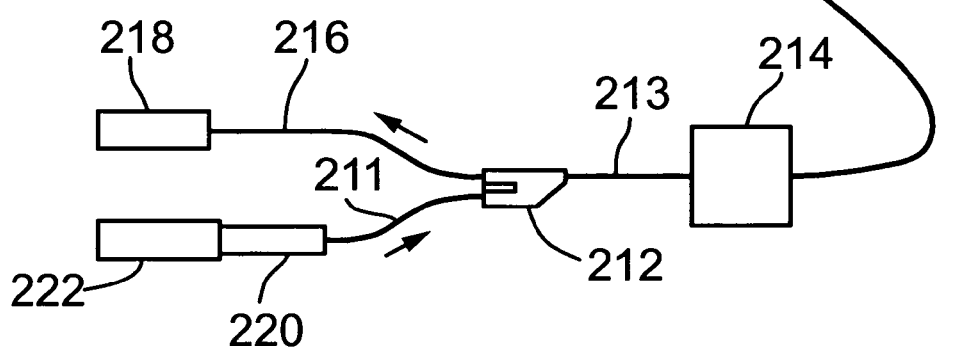
FIG. 21a
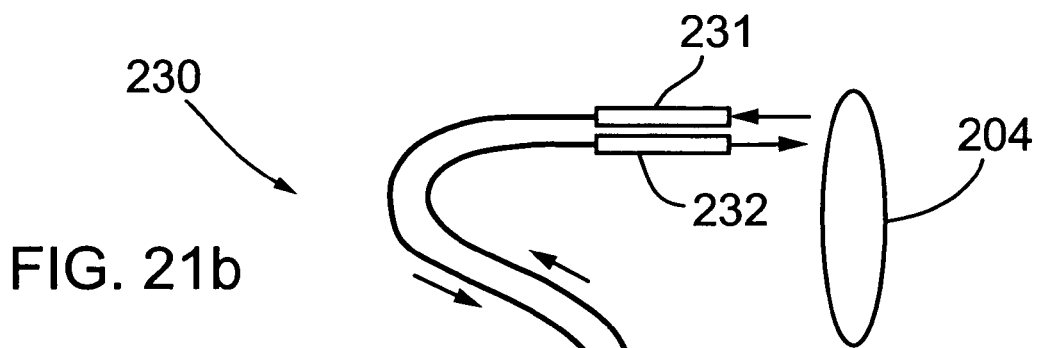
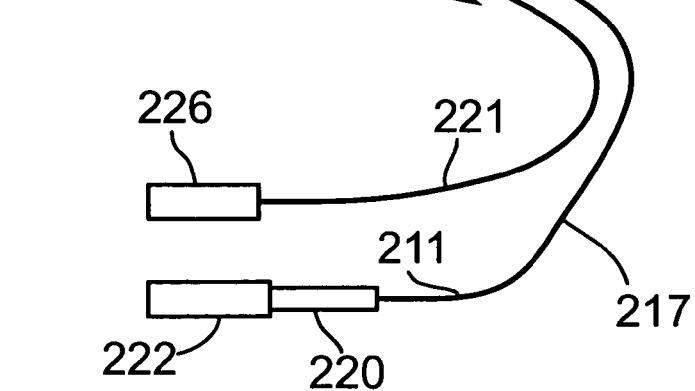
FIG. 21b

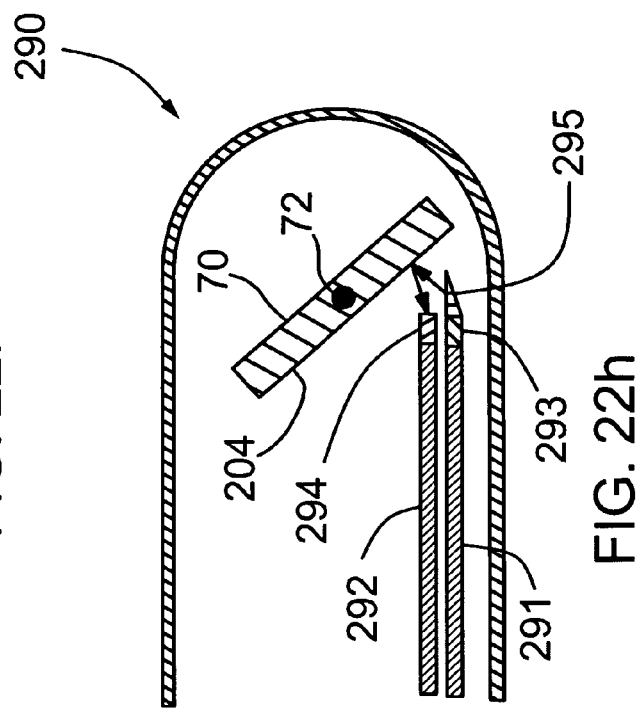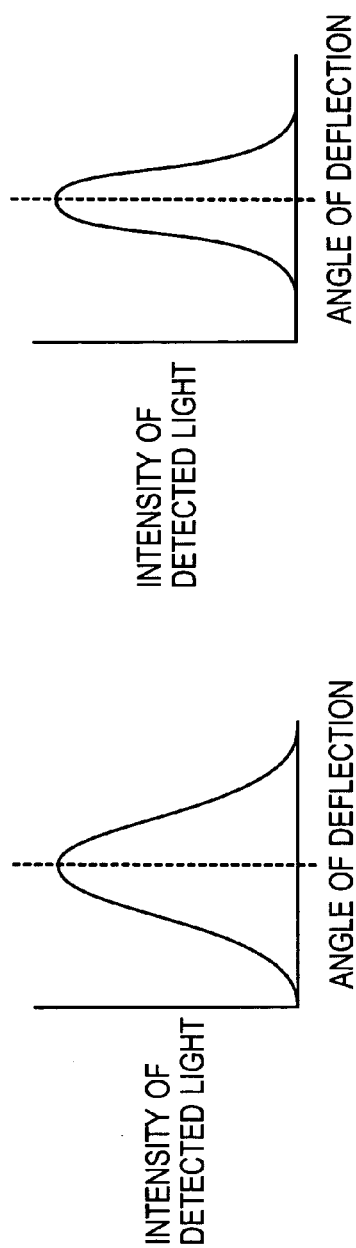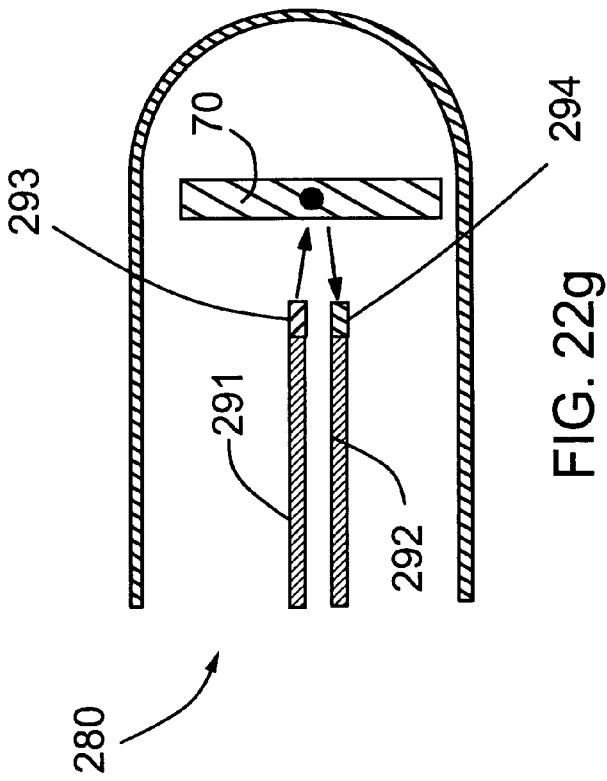

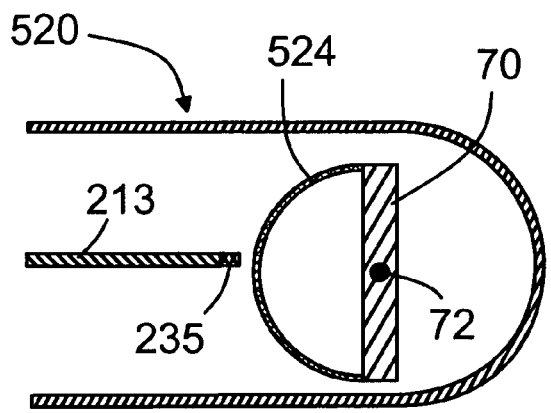
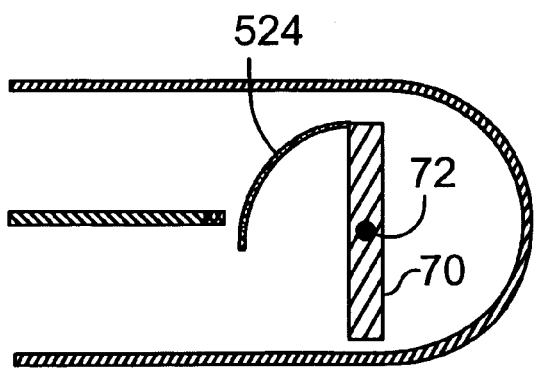
FIG. 23a    FIG. 23b
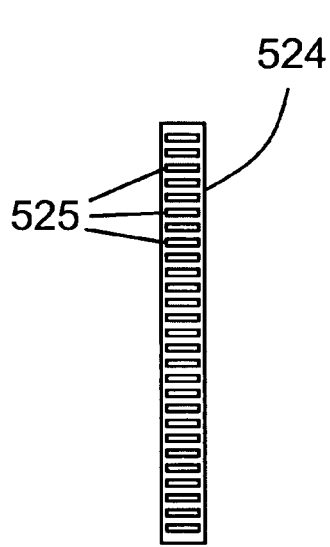 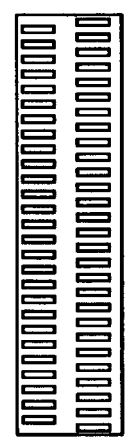 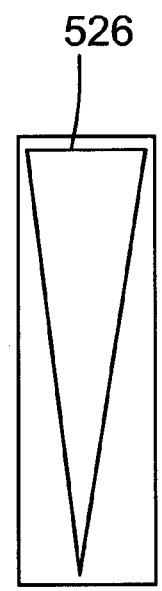
FIG. 23c    FIG. 23d    FIG. 23e

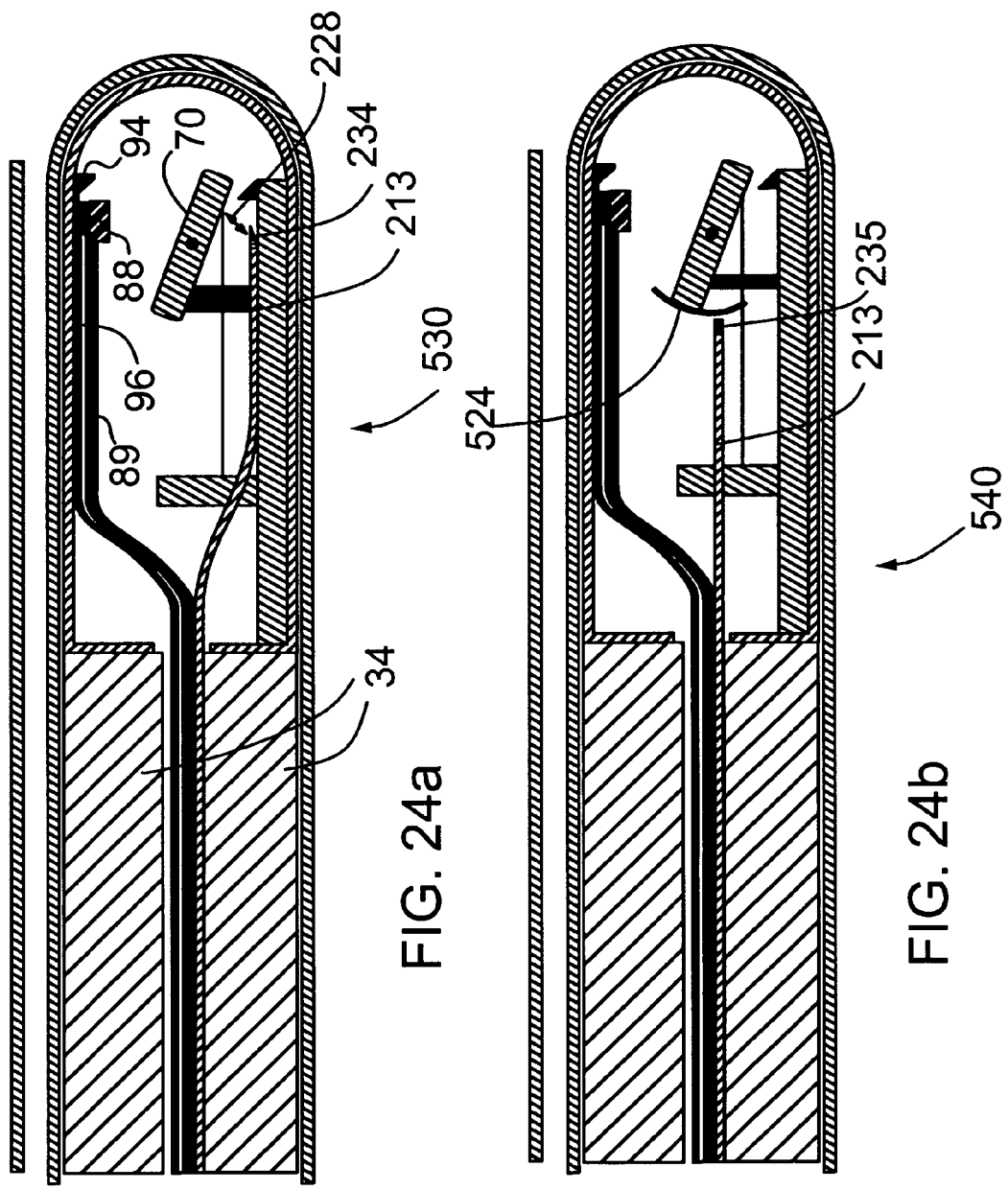

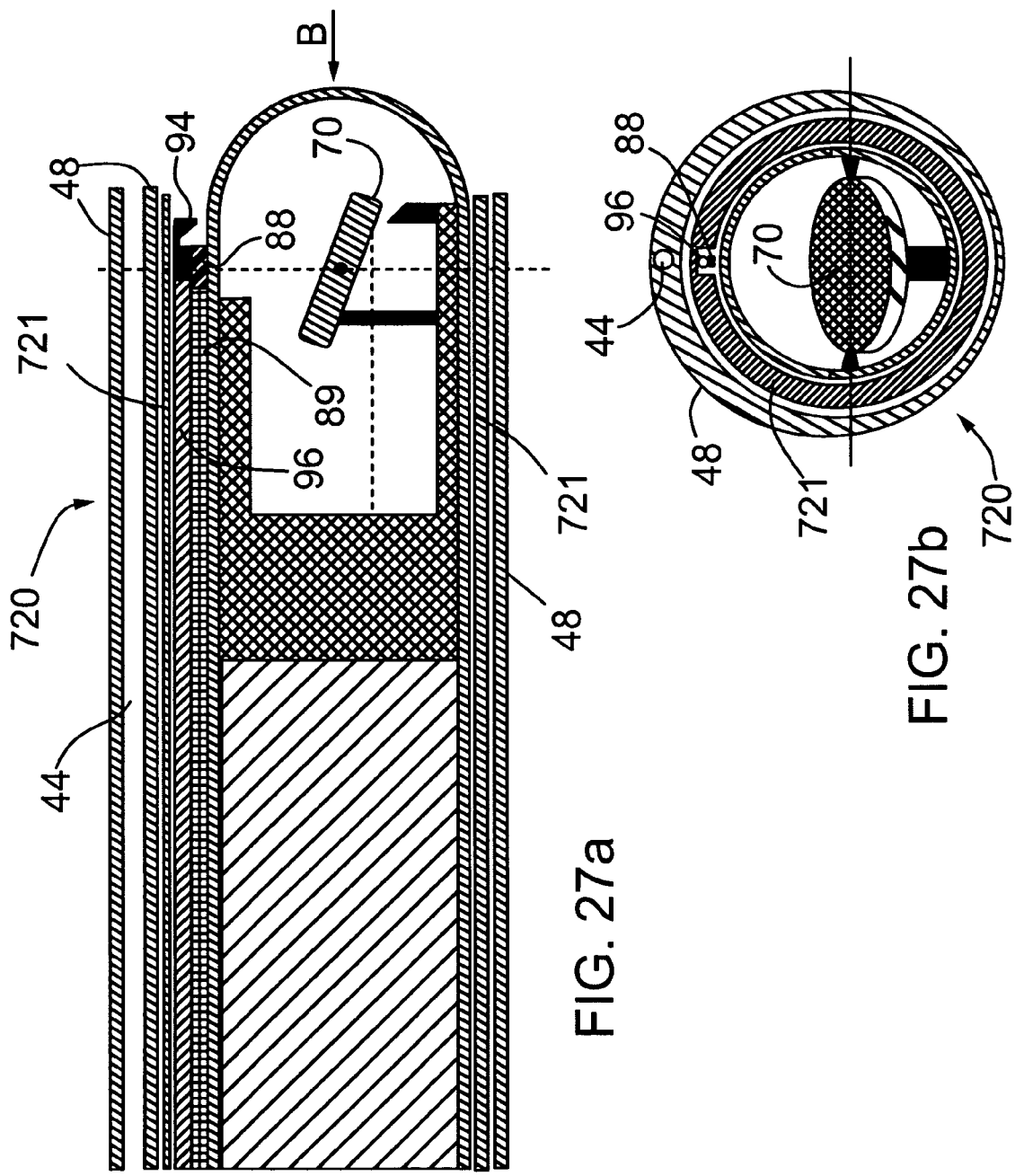

SCANNING MECHANISMS FOR IMAGING PROBE

CROSS REFERENCE TO RELATED U.S. APPLICATIONS

This patent application is a continuation-in-part (CIP) of U.S. patent application Ser. No. 12/010,206, which relates to, and claims the priority benefit from, U.S. Provisional Patent Application Ser. No. 60/881,169 filed on Jan. 19, 2007, in English, entitled IMAGING PROBE, which is incorporated herein by reference in its entirety.

FIELD OF THE INVENTION

The present invention relates generally to the field of imaging probes for imaging mammalian tissues and structures using high resolution imaging, including high frequency ultrasound and optical coherence tomography. More particularly the present invention relates to imaging assemblies incorporating scanning mechanisms for providing forward and side viewing capabilities of the imaging probe.

BACKGROUND OF THE INVENTION

High resolution imaging of the body serves multiple purposes, including any of i) assessing tissue structures and anatomy; ii) planning and/or guiding interventions on localized regions of the body; and iii) assessing the result of interventions that alter the structure, composition or other properties of the localized region. High resolution imaging in this particular case refers to high frequency ultrasound and optical imaging methods. For the purposes of this invention, high frequency ultrasound typically refers to imaging with frequencies of greater than 3. MHz, and more typically in the range of 9 to 100 MHz. High frequency ultrasound is very useful for intravascular and intracardiac procedures. For these applications, the ultrasound transducers are incorporated into a catheter or other device that can be inserted into the body. By way of example, two particularly important implementations of high frequency ultrasound are intravascular ultrasound (IVUS), for imaging blood vessels, and intracardiac echocardiography (ICE) for imaging cardiac chambers. Both ICE and IVUS are minimally invasive, and involve placing one or more ultrasound transducers inside a blood vessel or cardiac chamber to take high quality images of these structures.

Optical imaging methods based on fiber optic technology used in the field of medicine include optical coherence tomography, angioscopy, near infrared spectroscopy, Raman spectroscopy and fluorescence spectroscopy. These modalities typically require the use of one or more optical fibers to transmit light energy along a shaft between an imaging site and an imaging detector. Optical coherence tomography is an optical analog of ultrasound, and provides imaging resolutions on the order of 1-30 microns, but does not penetrate as deeply into tissue as ultrasound in most cases. Fiber optics can also be used to deliver energy for therapeutic maneuvers such as laser ablation of tissue and photodynamic therapy. Additional forms of imaging related to this invention include angioscopy, endoscopy and other similar imaging mechanisms that involve imaging a site inside the patient using a probe to take pictures based on either the backreflection of light in the visible or infrared ranges of the spectrum. Further additional forms of high resolution imaging can use acoustic energy to create optical energy (sonoluminescence imaging) or optical energy to create acoustic energy (photoacoustic imaging).

High resolution imaging means have been implemented in many forms for assessing several different regions of mammalian anatomy, including the gastrointestinal system, the cardiovascular system (including coronary, peripheral and neurological vasculature), skin, eyes (including the retina), the genitourinary systems, breast tissue, liver tissue and many others. By way of example, imaging of the cardiovascular system with high frequency ultrasound or optical coherence tomography has been developed for assessing the structure and composition of arterial plaque. High resolution imaging has been used to measure vessel or plaque geometry, blood flow through diseased arteries and the effect of interventions on arterial plaque (such as by atherectomy, angioplasty and/or stenting). Attempts have also been made using high resolution imaging to identify vascular lesions that have not led to clinical symptoms, but are at increased risk of rupturing or eroding and causing an acute myocardial infarction. These so-called "vulnerable plaques" are an area of intense interest as the prospect of treating such plaques to pre-empt adverse clinical events is conceptually appealing. However, no particular imaging modality has as of yet demonstrated efficacy in this regard.

Chronic total occlusions are a specific subset of vascular lesions where the entire lumen of the vessel has been occluded (based on the angiographic appearance of the lesion) for over approximately one month. Most intravascular imaging modalites are "side-viewing" and require passage of an intravascular imaging device through a lesion. In order to image chronic total occlusions, methods of high resolution imaging would be more useful if they were adapted to a "forward-looking" rather than "side-viewing" configuration.

Another area of increasing interest is the use of image guidance for procedures in structural heart disease and electrophysiology procedures. It is often necessary to place catheters within specific positions in the cardiac chambers in order to perform a therapeutic maneuver, such as the implantation of a device (such as a closure device for patent foramen ovales, valvular repair or replacement devices, left atrial appendage closure devices) or the placement of a therapeutic catheter (such as an ablation or cryotherapy catheter). It may also be necessary to guide intermediate steps in a procedure, such as crossing the atrial septum of the heart. The use of high resolution imaging can facilitate these steps. Intracardiac echo (ICE), currently performed using linear phased arrays, is one such technology currently used for this purpose.

SUMMARY OF RELATED ART

A catheter-based system for intravascular ultrasound is described by Yock (U.S. Pat. No. 4,794,931) to provide high resolution imaging of structures in blood vessels. This system comprises an outer sheath, within which there is an ultrasound transducer near the distal end of a long torque cable. When a motor rotates the torque cable and ultrasound transducer assembly, 2D cross-sectional images of anatomical structures, such as blood vessels, can be made. Linear translation of the catheter or the torque cable and ultrasound transducer in combination with the rotational motion of the ultrasound transducer allows for acquisition of a series of 2D images along the length of the catheter.

The use of intravascular ultrasound (IVUS) has since become commonplace, with many improvements and adaptations to the technology. A flexible torque cable (Crowley, U.S. Pat. No. 4,951,677) improves the fidelity of the transmission of rotational torque along the length of an IVUS catheter, minimizing an artifact known as non-uniform rotational distortion.

Liang et al. (U.S. Pat. Nos. 5,606,975 and 5,651,366, the entirety of which are incorporated by reference) describe means of implementing forward-looking intravascular ultrasound using relative rotational motion, where ultrasound is directed towards a mirror with a fixed tilt that causes the ultrasound beam to scan a surface ahead of the probe. The surface scanned approaches the shape of a curved plane, and the resultant shape results from relative rotational motion between the ultrasound transducer and the mirror. They also describe means of varying the angle of deflection of the mirror using either a micromotor, a gear clutch mechanism, steering cables or bimorph elements such a shape memory alloys, piezoelectric files or conductive polymers.

Suorsa et al (U.S. Pat. No. 6,315,732) describe a catheter for intravascular delivery that has an ultrasound transducer that can pivot around an axis other than the longitudinal axis of the catheter by means of a cable system.

Maroney et al (U.S. Pat. No. 5,373,849) and Gardineer (U.S. Pat. No. 5,373,845) also describe a catheter for pivoting an ultrasound transducer using a pivot/cable mechanism.

Hossack et al (WO/2006/121851) describe a forward looking ultrasound transducer using a capacitive micromachined ultrasound transducer (CMUT) and a reflective surface.

Couvillon et al (U.S. Pat. No. 7,077,808) describe an intravascular ultrasound catheter with a reflective component that is actuated using an electroactive polymer to achieve a variable angle of imaging from the longitudinal axis of the catheter.

Ultrasound transducers themselves are improving considerably, including the use of single crystal ultrasound transducers and composite ultrasound transducers.

The center frequency of IVUS lies within the range of 3 to 100 MHz and more typically in the range of 20 to 50 MHz. Higher frequencies provide higher resolution but result in lesser signal penetration and thus a smaller field of view. Depth of penetration can range from less than a millimeter to several centimeters depending on several parameters such as center frequency and geometry of the transducer, the transducer's sensitivity, the attenuation of the media through which the imaging occurs and implementation-specific specifications that affect the signal to noise ratio of the system.

Variations of high frequency ultrasound exist, where the signal acquisition and/or analysis of the backscattered signal are modified to facilitate obtaining or inferring further information about the imaged tissue exist. These include elastography, where the strain within tissue is assessed as the tissue is compressed at different blood pressures (de Korte et al Circulation. 2002 Apr. 9; 105(14):1627-30); Doppler imaging which assesses motion such as blood flow within anatomic structures; virtual histology, which attempts to infer the composition of tissue using the radio-frequency properties of the backscattered signal combined with a pattern recognition algorithm (Nair, U.S. Pat. No. 6,200,268); second harmonic imaging (Goertz et al, Invest Radiol. 2006 August; 41(8):631-8) and others. Each of these forms of imaging can be improved upon by means described in the present invention.

It is known that many tissue components have a degree of angle dependence when imaged using ultrasound from various angles. Courtney et al. (Ultrasound in Medicine and Biology, January 2002, 28:81-91) showed that the inner layers (media and intima) of a normal coronary artery have different angle-dependent backscatter properties than the outer layer (the adventitia). Picano at al (Circulation, 1985; 72(3):572-6) showed angular dependent ultrasound properties of normal, fatty, fibrofatty, fibrous and calcified tissues. A mechanism to image tissue, such as arterial plaque, at different angles, may be a valuable tool for improving in vivo tissue characterization by intravascular imaging means.

Tearney et al (U.S. Pat. No. 6,134,003) describe several embodiments that enable optical coherence tomography to provide higher resolution imaging than is readily obtained by high frequency ultrasound. Boppart et al (U.S. Pat. No. 6,485,413) describe several embodiments of optical coherence tomography imaging, including forward-looking implementations. Either an optical fiber or a gradient index (GRIN) lens is displaced using a mechanism such as a motor, a piezoelectric, a moveable wire, inflation means and others. Mao et al (Appl Opt. 2007 Aug. 10; 46(23):5887-94) describe methods for creating ultra-small OCT probes using single mode fiber, coupled to a small length of GRIN fiber which acts as a lens. Including an optical spacer between the fiber and the lens can alter the working distance of the fiber-lens system. Furthermore, adding a small length of no-clad fiber to the distal end, and cutting the no-clad fiber at an angle can add a deflecting element to the end of the fiber-lens system.

Optical coherence tomography generally has superior resolution to ultrasound and has the potential to better identify some structures or components in vascular and other tissues. It may also have better penetration than ultrasound through certain tissue components, such as calcified components. For example, fibrous cap thickness or the presence of inflammatory or necrotic regions near the surface of arteries may be better resolved with optical coherence tomography. However, optical coherence tomography is limited by its small penetration depth (on the order of 500 to 3000 microns) in most biologic media. Most such media are not optically transparent.

Variations of optical coherence tomography (OCT) include polarization sensitive OCT (PS-OCT) where the birefringent properties of tissue components can be exploited to obtain additional information about structure and composition; spectroscopic OCT which similarly provides improved information regarding the composition of the imaged structures; Doppler OCT which provides information regarding flow and motion; elastography via OCT; and optical frequency domain imaging (OFDI), which allows for a markedly more rapid acquisition of imaging data and therefore enables imaging to occur over a larger volume of interest in less time. Again, each of these forms of imaging can be improved upon by means of the present invention.

In comparison to OCT, ultrasound has the ability to better penetrate through biological media such as blood and soft tissues and has a depth of penetration that typically extends several millimeters beyond that of optical coherence tomography. The ability to image with either or both methods of imaging using a combined imaging device provides advantages with respect to selecting the required resolution and depth of penetration Several other forms of fiber-optic based imaging exist other than OCT. Amundson et al describe a system for imaging through blood using infra-red light (U.S. Pat. No. 6,178,346). The range of the electromagnetic spectrum that is used for their imaging system is selected to be one which optimizes penetration through blood, allowing optical imaging through blood similar to that afforded by angioscopy in the visible spectrum, but without the need to flush blood away from the region being imaged.

Angioscopy, endoscopy, bronchoscopy and many other imaging devices have been described which allow for the visualization of internal conduits and structures (such as vessels, gastrointestinal lumens and the pulmonary system) in mammalian bodies based on the principle of illuminating a region within the body near the distal end of a rigid or flexible shaft. Images are then created by either having a photodetector array (such as a CCD array) near the end of the shaft or by having a bundle of fiber optics transmit the received light from the distal end of the shaft to the proximal end where a photodetector array or other system that allows the operator to generate or look at an image representative of the illuminated region. Fiber bundles are bulky and reduce the flexibility of the shaft among other disadvantages.

Other fiber optic based modalities for minimally invasive assessment of anatomic structures include Raman spectroscopy as described by Motz et al (J Biomed Opt. 2006 March-April; 11(2)), near infrared spectroscopy as described by Caplan et al (J Am Coll Cardiol. 2006 Apr. 18; 47(8 Suppl): C92-6) and fluorescence imaging, such as tagged fluorescent imaging of proteolytic enzymes in tumors (Radiology. 2004 June; 231(3):659-66).

It would be advantageous to provide high resolution imaging probes for acoustic or optical imaging as "forward-looking" probes rather than "side-viewing" proves. It would also be helpful to provide similar probes that can look backwards, or from multiple angles in a generally side-viewing configuration. It would also be helpful to provide similar probes that are capable of generating 3D imaging data sets.

It would also be advantageous to provide 3D high-resolution imaging probes that combine ultrasound imaging with one or more optical imaging means.

It would also be advantageous to provide minimally invasive imaging probes that can be used for photoacoustic imaging or sonoluminescent imaging.

We present several embodiments for novel scanning mechanisms that are broadly applicable to medical imaging.

To the best of the inventors' knowledge, there is no description of a system or means that utilizes the scanning mechanisms described in the present invention.

SUMMARY OF THE INVENTION

The present invention provides imaging probes for imaging mammalian tissues and structures using high resolution imaging, including high frequency ultrasound and/or optical coherence tomography. More particularly the present invention relates to imaging assemblies incorporating scanning mechanisms for providing forward and side viewing capabilities of the imaging probe.

Thus in one embodiment the present invention provides imaging probe for insertion into bodily lumens and cavities for imaging an interior of said bodily lumens and cavities or imaging exterior surfaces of a body, comprising:

a) a hollow shaft having a longitudinal axis having distal and proximal end sections and a midsection, an imaging assembly being located in said elongate hollow shaft for emitting an energy beam and receiving reflected energy signals reflected back from interior surfaces of said bodily lumens and cavities or exterior surfaces, said imaging assembly being connected at a first position along an imaging conduit, said imaging conduit extending through the hollow shaft and being connectable at a second position thereof to an image processing and display system through the proximal end section, said imaging conduit being configured to deliver energy to said imaging assembly;

b) said imaging conduit and said imaging assembly being connectable to a rotational drive mechanism for imparting rotational motion to said imaging conduit and said imaging assembly about said longitudinal axis at an angular velocity, the rotational drive mechanism including adjustment means for varying said angular velocity; and c) said imaging assembly including a scanning mechanism having a movable member movably mounted about an axis substantially perpendicular to said longitudinal axis and positioned to receive said energy beam from said imaging conduit and direct said energy beam out of said elongate hollow shaft at an imaging angle with respect to said longitudinal axis to give forward or side viewing capability of said imaging assembly and to receive said received reflected energy signals back to said imaging conduit, said movable member being movably mounted in such a way that the imaging angle is variable and a function of said angular velocity, said scanning mechanism being configured to receive and deliver said reflected energy signals to said image processing system through said imaging conduit; and d) said rotational drive means being connectable to a controller which is connected to said image processing and display system; and e) an imaging angle encoder circuit coupled to said imaging assembly and the controller for detecting the variable angle of the movable member, said imaging angle encoder including an angle encoder interface associated with said movable member, and including optical delivery means for delivering light to said angle encoder interface, and receiving light reflected from said angle encoder interface and delivering said reflected light to a detector, and wherein an output of said detector is representative of the imaging angle or a change in the imaging angle based on the degree of deflection or tilt of the deflectable or movable component.

In another embodiment the present invention provides an imaging probe for insertion into bodily lumens and cavities for imaging an interior of said bodily lumens and cavities or imaging exterior surfaces of a body, comprising:

a) an outer elongate sheath and an imaging conduit located in said outer elongate sheath having a longitudinal axis having distal and proximal end sections and a midsection, an imaging assembly being located in said distal end section of said imaging conduit for directing an energy beam out of said distal end section and receiving reflected energy signals reflected back from interior surfaces of said bodily lumens and cavities or exterior surfaces, said imaging assembly being connected to a first end of said imaging conduit, said imaging conduit extending through the outer elongate sheath and being connectable at a second end thereof to an image processing and display system through the proximal end section;

b) said imaging conduit and said imaging assembly being connectable to a rotational drive mechanism for imparting rotational motion to said imaging conduit and said imaging assembly, relative to said outer elongate sheath, about said longitudinal axis at an angular velocity, the rotational drive mechanism including adjustment means for varying said angular velocity; and c) said outer elongate sheath having a distal end section and a proximal end section and a midsection aligned with said proximal end section, midsection and distal end section of said imaging conduit, and an energy emitting device affixed to said outer elongate sheath at said distal end section thereof for producing said energy beam;

d) said imaging assembly including a scanning mechanism including a movable reflective member configured to receive said energy beam from said energy emitting device and to deliver said energy beam along a path out of said imaging conduit at a variable angle with respect to said longitudinal axis to give forward or side viewing capability of said imaging assembly, wherein said movable reflective member is mounted in such a way that the variable angle is a function of said angular velocity, said scanning mechanism being configured to receive and deliver said reflected energy signals to said image processing system through said imaging conduit; and e) said rotational drive means being connectable to a controller which is connected to said image processing and display system.

In a further embodiment, the present invention provides a imaging probe for insertion into bodily lumens and cavities for imaging an interior of said bodily lumens and cavities or imaging exterior surfaces of a body, comprising:

a) an outer elongate sheath, an inner elongate sheath located in said outer elongate sheath having a longitudinal axis having distal and proximal end sections and a midsection, and an imaging conduit located in said inner elongate sheath having a longitudinal axis having distal and proximal end sections and a midsection, an imaging assembly being located in said distal end section of said imaging conduit for directing an energy beam out of said distal end section and receiving reflected energy signals reflected back from interior surfaces of said bodily lumens and cavities or exterior surfaces, said imaging assembly being connected to a first end of said imaging conduit, said imaging conduit extending through the inner elongate sheath and being connectable at a second end thereof to an image processing and display system through the proximal end section;

b) said imaging conduit containing said imaging assembly being connectable to a first rotational drive mechanism for imparting rotational motion to said imaging conduit and said imaging assembly, relative to said inner elongate sheath, about said longitudinal axis at an angular velocity, the rotational drive mechanism including adjustment means for varying said angular velocity; and c) said outer elongate sheath having a distal end section and a proximal end section and a midsection aligned with said proximal end section, midsection and distal end section of said inner elongate sheath, and an energy emitting device affixed to said inner elongate sheath at said distal end section thereof for producing said energy beam;

b) said inner elongate sheath being connectable to a second rotational mechanism for imparting rotational motion to said inner elongate sheath, for rotating said energy emitting device, relative to said imaging conduit, about said longitudinal axis;

d) said imaging assembly including a scanning mechanism which includes a movable member configured to receive said energy beam from said energy emitting transducer and to deliver said energy beam along a path out of said elongate hollow shaft at a variable angle with respect to said longitudinal axis to give forward or side viewing capability of said imaging assembly, wherein said movable member is mounted in such a way that the variable angle is a function of said angular velocity, said scanning mechanism being configured to receive and deliver said reflected energy signals to said image processing system through said imaging conduit; and e) said rotational drive means being connectable to a controller which is connected to said image processing and display system.

In another embodiment there is provided a mechanism for insertion into bodily lumens and cavities that enables the delivery and/or collection of energy to an interior bodily region, comprising:

a rotary component having a rotary axis, a rotary drive mechanism connected to said rotary component, a tiltable or deflectable component, and a coupling mechanism for coupling said tiltable or deflectable component to said rotary component, an energy emitting device configured and positioned in said rotary component to deliver an energy beam from said tiltable or deflectable component, detection means configured and positioned in said rotary component to detect energy from said tiltable or deflectable component, said coupling mechanism being configured to couple said tiltable or deflectable component to said rotary component in such a way that a change in speed of rotation of the rotary component induces movement of said tiltable or deflectable component resulting in a change of an angle between a surface of the tiltable or deflectable component with respect to the rotary axis, wherein said rotary component is configured to rotate around said rotary axis, when driven by said rotary drive mechanism, that provides an initial degree of freedom with respect to a direction in which the energy beam is delivered to, or collected from, the tiltable or deflectable component, said tiltable or deflectable component providing a second degree of freedom with respect to the direction in which the energy beam is delivered or collected from, whereby the tiltable or deflectable component causes the energy beam to be delivered or collected at a general angle from the rotary axis, whereby the general angle from the rotary axis is determined substantially by the rotation of the rotary component.

A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, in which:

FIG. 2 is a perspective drawing of a flexible imaging probe with a connector, conduit and imaging assembly;

FIG. 2a is a cross-sectional view of the mid section of the imaging probe of FIG. 2 taken along the dotted line;

FIG. 2b is an expanded perspective drawing of the distal region of the imaging probe of FIG. 2;

FIG. 3a shows one embodiment of an over-the-wire configuration for an external sheath that may be incorporated with the imaging probe if a guidewire lumen is included;

FIG. 3b shows a cross-section through the imaging probe along the vertical line 3b-3b in FIG. 3a to demonstrate the guidewire lumen configuration;

FIG. 3c shows a rapid access configuration for an external sheath that may be incorporated with the imaging probe if a guidewire lumen is included;

FIG. 3d shows a cross-section through a portion of the imaging probe taken along line 3d-3d in FIG. 3c that does not contain a guidewire lumen;

FIG. 3e shows a cross-section through a portion of the imaging probe along line 3e-3e in FIG. 3c that does contain a guidewire lumen;

FIG. 4b illustrates the relevant axes for an imaging assembly containing a tiltable component of FIG. 4a;

FIGS. 4c-4l illustrate some examples of longitudinal and axial cross-sections of tiltable components that would have preferred orientations if they were rotated around the longitudinal axis of the imaging probe in the absence of external forces, in which the tilt axis is substantially perpendicular to the longitudinal axis;

FIGS. 5a-5g demonstrate the distal end of an imaging probe capable of both acoustic and optical imaging where a tiltable deflecting surface can change the imaging angle as a function of the rotational velocity of the imaging assembly;

FIGS. 6a-6e demonstrate the distal end of an imaging probe capable of acoustic imaging where an acoustic transducer is directly mounted on a tiltable component;

FIGS. 6f to 6j demonstrate the distal end of an imaging probe capable of optical imaging where at least a portion of an optical emitter and/or received is mounted directly on a tiltable component;

FIGS. 10a and 10b demonstrate an example of an imaging probe where the deformable component carries an energy deflecting component rather than an emitter and/or receiver;

FIG. 14a is an example of an imaging probe that includes a tiltable component to act as a deflector and an optical rotary encoder to identify the angular position of the imaging assembly relative to an external sheath;

FIG. 14b provides a cross-sectional depiction of the probe where a rotary encoder is included;

FIG. 17a-17g depict embodiments suitable for combining optical imaging with an ultrasound transducer for the present invention.

FIG. 18a is a perspective drawing of a deflecting component that comprises a flat optically reflective layer and a shaped acoustically reflective layer;

FIGS. 18b through 18d depict cross-sections of the deflecting component;

FIG. 21a shows a schematic diagram for an imaging angle encoder circuit for detecting the imaging angle of a tiltable or deflectable member;

FIG. 21b is a schematic diagram for an alternative embodiment of the optical encoder circuit shown in FIG. 21a;

FIG. 22a shows an embodiment of an imaging probe configured to use the imaging angle encoder circuit of FIG. 21a;

FIG. 22c shows an alternative embodiment of the probe shown in FIG. 22a;

FIG. 22e shows an exemplary plot of the intensity of light that would be detected as a function of angle of deflection without the use of a lens used in the embodiment of FIG. 22d;

FIG. 22f shows a comparison plot of how the intensity of light detected would be more sensitive to slight changes in the angle of deflection or tilt as a result of adding a focusing element to the distal end of fiber optic as used in the embodiment of FIG. 22d;

FIG. 22g shows another alternative embodiment of an imaging probe that uses a light source or a photodetector sized with adequate miniaturization to fit within the distal end the imaging probe;

FIG. 22h shows another embodiment of the imaging probe of FIG. 22g where a prism is further employed to deflect light from the light source;

FIG. 23a shows an alternative embodiment of an imaging probe wherein the encoder interface includes a generally arc-shaped encoder that extends proximate to the distal end of a fiber optic in the imaging angle encoding circuit which is attached to a tiltable component at both ends;

FIG. 23b shows an alternative embodiment of the imaging probe of FIG. 23a in which the arc-shaped encoder is attached to the tiltable component at a single end;

FIGS. 23c, 23d and 23e show non-limiting designs for encoder interfaces prior to being configured into the arc-shaped interfaces used in the imaging probes of FIGS. 23a and 23b;

FIG. 24a is a cross sectional view of an alternative embodiment of the imaging probe shown in FIG. 5a which includes an encoder circuit fiber optic within the imaging conduit;

FIG. 24b shows another alternative embodiment of an imaging probe including an encoder circuit where the encoder interface is an arc-shaped encoder that resides proximate to the distal end of encoder circuit fiber optic;

FIG. 26 shows an experimental setup used to demonstrate the functioning of the scanning mechanism shown in FIG. 25a;

FIG. 27a shows longitudinal cross sectional view of an embodiment of an imaging probe which makes use of relative rotational motion, but allows the rotational position of the ultrasound transducer and/or optical emitter/receiver to be adjusted by separately mounting the ultrasound transducer and/or optical emitter/receiver; and FIG. 27b shows a view along arrow B of FIG. 27a.

DETAILED DESCRIPTION OF THE INVENTION

Generally speaking, the systems described herein are directed to an imaging probe using either optical or ultrasonic (or both) imaging. As required, embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to an imaging probe.

As used herein, the terms "about", and "approximately" when used in conjunction with ranges of dimensions, temperatures or other physical properties or characteristics is meant to cover slight variations that may exist in the upper and lower limits of the ranges of dimensions so as to not exclude embodiments where on average most of the dimensions are satisfied but where statistically dimensions may exist outside this region. For example, in embodiments of the present invention dimensions of components of the imaging probe are given but it will be understood that these are not meant to be limiting.

As used herein, the phrase "co-registration of images" refers to the process of identifying a subset of imaging data acquired by one imaging means with a subset of imaging data acquired using another imaging means where the identified imaging data from the two means was acquired by detecting a form of imaging energy (e.g. photons or ultrasound) from the same object (or tissue in the case of the present invention). Each co-registered point in the first subset can then be mapped to a corresponding point in the second subset such that the two points from the two different imaging means are thought to have been acquired from a similar focal region of the imaged object (or tissue).

Successful and accurate co-registration of images, or portions thereof, between images acquired using two (2) or more imaging means is helpful in that it can provide multiple opportunities to assess features of interest of the imaged object by more than one imaging means.

Figure 1:
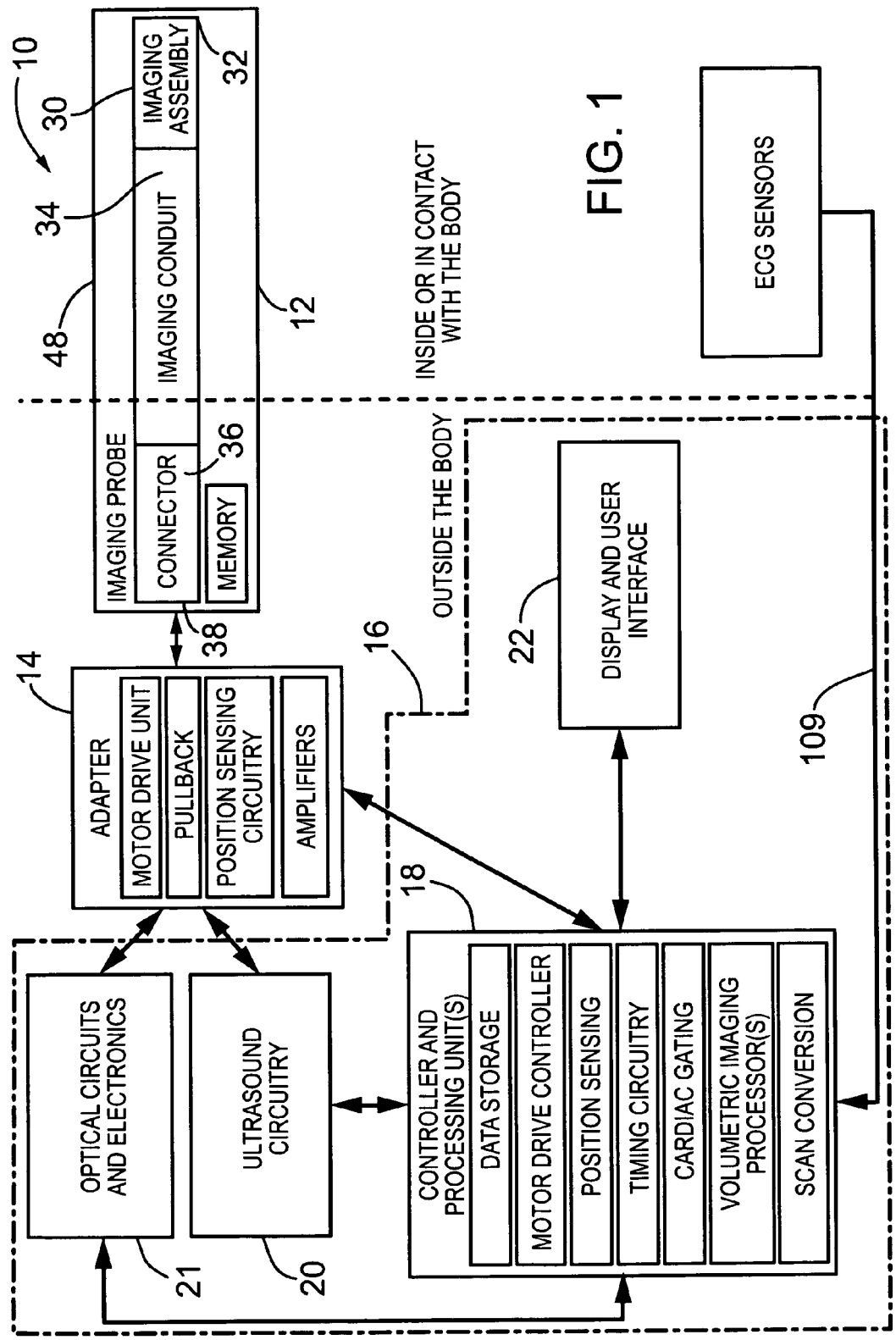
FIG. 1 is a schematic of an imaging system for either ultrasound imaging, optical imaging or both.

FIG. 1 represents an overview of an exemplary imaging system constructed in accordance with the present invention shown generally at 10. It comprises an imaging probe 12, which connects via an adapter 14 to an image processing and display system 16. The image processing and display system 16 comprises the necessary hardware to support one or more of the following imaging modalities: 1) ultrasound, 2) optical coherence tomography, 3) angioscopy, 4) infrared imaging, 5) near infrared imaging, 6) Raman spectroscopy-based imaging and 7) fluorescence imaging.

Implementations of the optical coherence tomography, ultrasound, angioscopy and infrared imaging circuitry have been described in the prior art.

The system herein described further typically comprises a controller and processing unit 18 to facilitate the coordinated activity of the many functional units of the system, and may further comprise a display and/or user interface and may further comprise electrode sensors 109 to acquire electrocardiogram signals from the body of the patient being imaged. The electrocardiogram signals may be used to time the acquisition of imaging data in situations where cardiac motion may have an impact on image quality. The electrocardiogram may also serve as a trigger for when to begin an acquisition sequence, such as when to begin changing the speed of rotation of a motor in order to cause a desired scan pattern to take effect. For example, ECG-triggered initiation of an imaging sequence may enable images to be acquired during a particular phase of the cardiac cycle, such as systole or diastole.

The optical circuits and electronics 21 forming image processing and display system, if included in a particular implementation of the present invention, may include any or all of the following components: interferometer components, one or more optical reference arms, optical multiplexors, optical demultiplexors, light sources, photodetectors, spectrometers, polarization filters, polarization controllers, timing circuitry, analog to digital converters and other components known to facilitate any of the optical imaging techniques described in the background and prior art sections. The ultrasound circuitry 20 may include any or all of the following components: pulse generators, electronic filters, analog to digital converters, parallel processing arrays, envelope detection, amplifiers including time gain compensation amplifiers and other components known to facilitate any of the acoustic imaging techniques described in the background and prior art sections.

The controller and processing units 18, if included in a particular implementation of the present invention, serve multiple purposes and the components would be markedly adapted based on the needs of a particular imaging system. It could include one or a combination of motor drive controller, data storage components (such as memory, hard drives, removable storage devices, readers and recorders for portable storage media such as CDs and DVDs), position sensing circuitry, timing circuitry, cardiac gating functionality, volumetric imaging processors, scan converters and others. A display and user interface 22 is also optionally provided for either real time display or display of data at a time later than the time at which imaging data is acquired.

The imaging probe 12 comprises an imaging assembly 30 near its distal end 32, an optional imaging conduit 34 along a substantial portion of its length, and a connector 36 at its proximal end 38. For the purposes of this invention, an imaging assembly 30 generally refers to the component of the imaging probe 12 from which the signals (acoustic or optical (or both)) are collected for the purposes of imaging a region that is proximate to the imaging assembly 30. The imaging assembly 30 includes one or more emitters of imaging energy and one or more receivers of imaging energy. For the purposes of this invention, "imaging energy" refers to light or acoustic energy or both. Specifically, light refers to electromagnetic waves that span the ultraviolet, visible and infrared spectrum of wavelengths. For example, for acoustic imaging, the imaging assembly 30 contains an ultrasound transducer that is both an emitter and receiver of acoustic energy.

For optical imaging, the imaging assembly 30 typically contains the distal tip of a fiber optic, as well as a combination of optical components such as a lens (such as a ball lens or GRIN lens), which collectively serve the purpose of acting as an optical receiver and may also serve as an optical emitter. A mirror and/or a prism are often incorporated as part of an optical emitter and/or receiver. The imaging assembly 30, connector 36 and/or imaging conduit 34 may be liquid-filled, such as with saline and may be flushed.

The imaging probe 12 may contain ports at one or more points along its length to facilitate flushing. For optical imaging, it is possible to consider a gas filled imaging probe 12. Preferably, the gas would substantially comprise carbon dioxide or another readily dissolved gas. Alternatively, the imaging assembly may be compartmentalized such that there is at least one gas-filled compartment or lumen for optical imaging and at least one fluid-filled compartment or chamber for acoustic imaging.

The imaging conduit 34 comprises at least one optical waveguide or at least one conductive wire (preferably two or more) that connect an emitter and/or receiver via a connector to an adapter. The imaging conduit 34 may also act as a mechanical force transmission mechanism for rotating or translating the imaging assembly. For example, the imaging conduit 34 may comprise a fiber optic, wrapped by two layers of electrical wire that are insulated from each other. The imaging conduit 34 may further be reinforced by other structural features, such as helically wrapped wires or other designs used to construct imaging torque cables for rotating scan mechanisms, as described in the related art.

The adapter 14 facilitates transmission of signals within any fibers and/or wires to the appropriate image processing units. It preferably contains a motor drive unit, for imparting rotation motion to rotary components of the imaging probe. The adapter 14 may also incorporate a pullback mechanism 49 (FIG. 2d) or a reciprocating push-pull mechanism to facilitate longitudinal translation of the imaging assembly. Such longitudinal translation of the imaging assembly 30 may occur in conjunction with the longitudinal translation of an external shaft that surrounds the imaging conduit 34, or may occur within a relatively stationary external shaft.

Additional sensors may be incorporated as part of the adapter 14, such as position sensing circuitry, for example to sense the angle of rotation of a rotary component within the imaging probe 12. The imaging probe 12 may also include a memory component such as an EEPROM or other programmable memory device that includes information regarding the imaging probe to the rest of the imaging system. For example, it may include specifications regarding the identification of specifications of the imaging probe 12 and may also include calibration information regarding the probe 12. Additionally, the adapter 14 may include amplifiers to improve the transmission of electrical signals or power between the imaging probe and the rest of the system.

It is important to recognize the need to optimize the geometry of a minimally invasive probe so that it is as small as reasonably possible to achieve its desired purpose. Current IVUS and ICE probes are approximately 0.9 to 4 mm in diameter and the smaller sizes of probes can be delivered more distally within the vascular tree of the coronary anatomy as the vessel size tapers down. Thus, smaller sizes generally allow for interrogation of a larger portion of the coronary anatomy. It is therefore desirable to have embodiments of a probe that enable imaging, such as using imaging performed with the scanning mechanisms described herein, in arrangements that minimize certain dimensions of the probe, such as the diameter of the probe.

FIG. 2 is a perspective drawing of a flexible catheter containing a fiber optic 40 and a co-axial electrical wire 50. The proximal connector contains fiber optic 40 that can be received by the adapter to optically couple the imaging fiber optic 40 to the optical imaging system "back-end". There are also electrical connectors 56 that allow the one or more electrical conduits to be connected to the ultrasound circuitry and/or controller and processing units. In embodiments where the imaging conduit rotates around its longitudinal axis, there may be a need to couple the rotating components of the imaging fiber optic with a relatively stationary fiber optic that connects to the optical imaging system's back-end 16. The coupling of a rotating fiber optic probe can be accomplished using a fiber optic rotary joint incorporated either as part of the proximal connector of the imaging probe 36 or as part of the adapter 14. Similarly, in embodiments where the imaging conduit rotates around its longitudinal axis, there may be a need to couple conductive wires that rotate with the imaging conduit with relatively stationary conductors of the ultrasound circuitry and/or controller and processing units, preferably by means of slip rings. These slip rings can be incorporated as part of the proximal connector of the imaging probe 36 or as part of the adapter 14.

FIG. 2a shows a cross sectional view of the mid section of the imaging probe of FIG. 2 taken along the dotted line which shows a fiber optic 40, guidewire port 44 and guide wire 42, imaging conduit 34, imaging conduit lumen 46, external sheath 48 which is a hollow, flexible elongate shaft made of a physiologically compatible material and having a diameter suitable to permit insertion of the hollow elongate shaft into bodily lumens and cavities, and coaxial electrical wiring 50. The expanded detailed view of the end of the imaging probe 10 shown in FIG. 2b shows the distal end of the guidewire 42 extended beyond the end of the outer sheath 48 and a flush port 54 at the end of the sheath 48. In FIG. 2 the proximal end of the imaging probe 10 includes another guidewire port 55 into which guidewire 42 is inserted and the connector assembly 36 which includes a flush port 58 and electrical contacts 56 along the connector body.

Figure 2C:
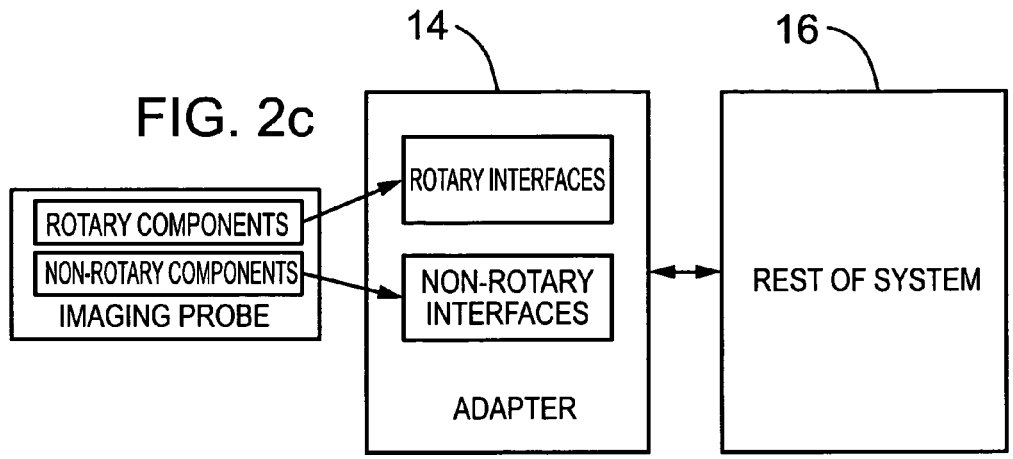
FIG. 2c shows a schematic of how the rotary and non-rotary components of the imaging probe can be coupled with an adapter to the rest of an imaging system.
Figure 2D:
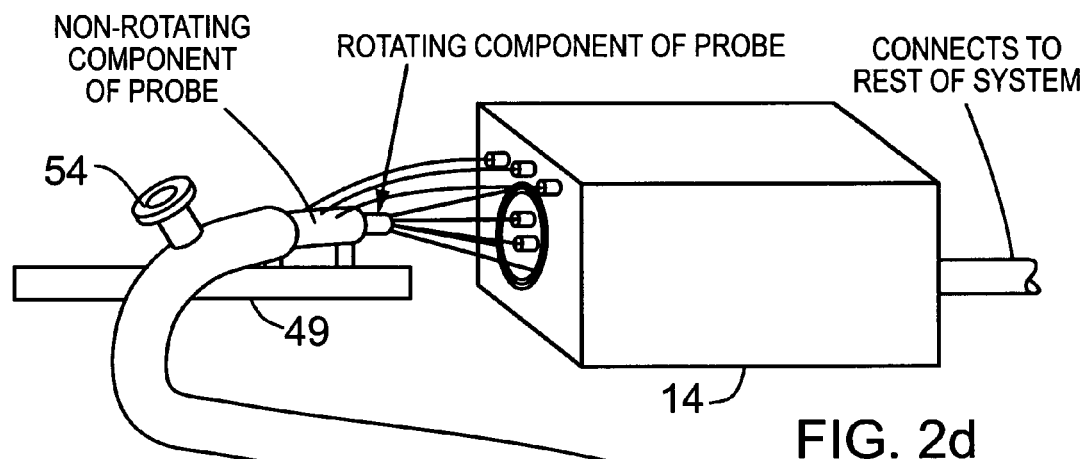
FIG. 2d is a perspective drawing of an example of the coupling of the rotary and non-rotary components of the probe to an adapter.

FIG. 2c shows a schematic of how the rotary and non-rotary components of the imaging probe can be coupled with an adapter to the rest of an imaging system. FIG. 2d schematically shows how the rotating components of the imaging probe can be coupled to the rotating components of an adapter. The rotating components of each can be electrically, optically and/or mechanically coupled using connectors and other configurations known in the art. Similarly, the non-rotating components of the imaging probe can be coupled to the non-rotating components of the adapter 14. The adapter 14 can include slip rings, optical rotary joints and other such implements for electrically or optically coupling a rotary component to a non-rotary component and enable communication of necessary electrical and optical signals with the rest of the system.

Dual-fiber optical rotary joints are also available but considerably more complex. Electrical coupling between any conductor mounted onto a rotating component in the imaging probe 12 can be coupled to non-rotating conducting elements via metallic slip rings and springs, metallic slip rings and brushes or other commonly known methods of forming conductive contact between a stationary conductor and a rotary conductor.

While the electrical, optical and mechanical connections are shown separately in FIG. 2d, it is possible to reduce the several connectors that must each be separately connected between the probe and adapter with fewer connectors by combining several connectors into combined connectors, as needed for a specific embodiment.

While the embodiments described above are illustrated using both acoustic and optical imaging, it is possible to implement the catheter either without acoustic means or without optical means.

Figure 3A:
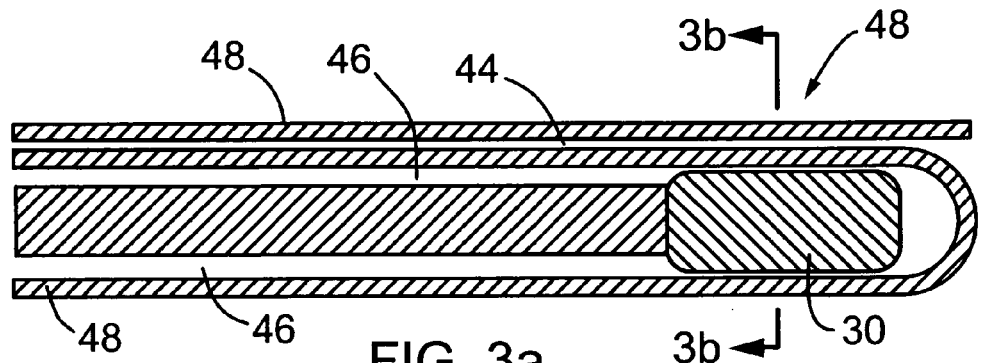
FIGS. 3a to 3e are representative of general imaging catheter configurations described in the prior art.
Figure 3B:
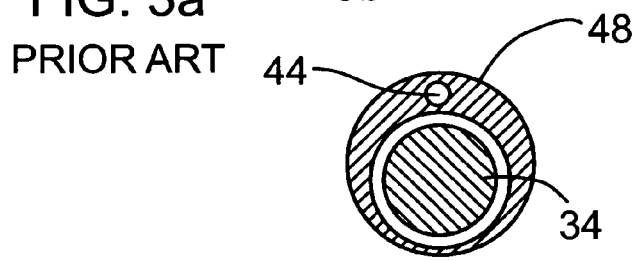

FIG. 3a shows one embodiment of an over-the-wire configuration for an external sheath at 48 and FIG. 3b shows a cross-section of sheath 48 through the portion that contains the imaging assembly 30 along the vertical line 3b-3b in FIG. 3a. In FIG. 3a the guidewire conduit 44 is located in the thicker portion of the outer sheath 48 as seen in the cross sectional of FIG. 3b along the vertical line 3b-3b of FIG. 3a.

Figure 3C:
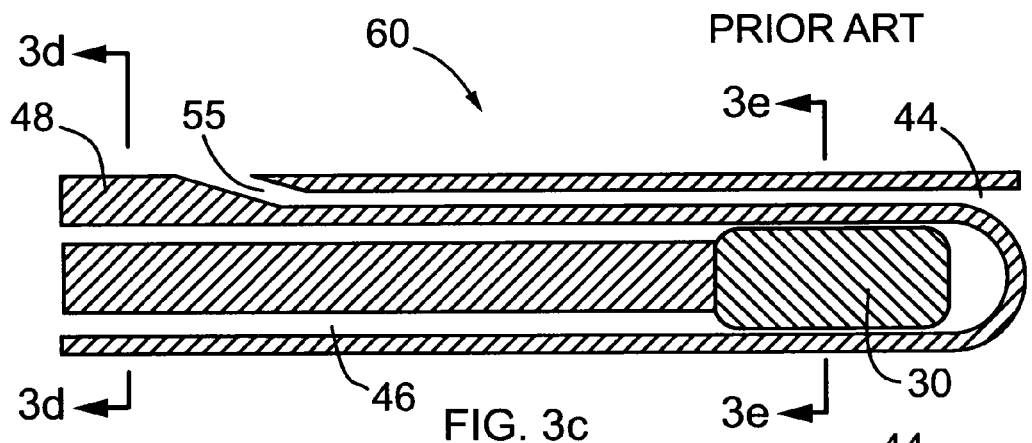
Figure 3D:
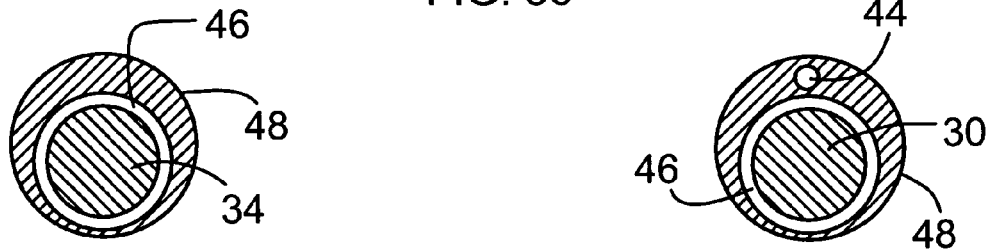
Figure 3E:
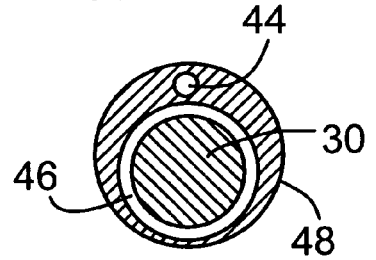

FIG. 3c shows an embodiment of another sheath 60 that is a "rapid exchange" configuration for the external sheath that may be incorporated with the imaging probe if a guidewire is required. Sheath 60 in FIG. 3c includes the entry port 55 shown in FIG. 2. FIG. 3d shows a cross-section of the "rapid-exchange" configuration 60 through the portion that is proximal to the entry port 55 for a guidewire along line 3d-3d in FIG. 3c. FIG. 3e shows a cross-section along line 3e-3e in FIG. 3c.

The present invention discloses embodiments of scanning mechanisms for providing forward and side-looking ultrasound (IVUS) and optical coherence tomography (OCT) imaging. For ultrasound and optical coherence tomography, the ability to adjust the angle of propagation of the emitted and/or received imaging energy, when combined with the rotational motion of the imaging assembly, allows a 3D volume to be scanned. For angioscopy and infrared imaging, the ability to adjust the angle of propagation of the emitted and/or received imaging energy, when combined with the rotational motion of the imaging assembly, allows an image to be produced using a single fiber optic rather than requiring a bundle of fibers or an array of photosensitive elements. Such an improvement results in greater flexibility and/or allows for further miniaturization of imaging devices.

It is a further advantage of this invention that the optical and acoustic imaging can occur in a configuration where the optical and acoustic imaging energy travels through the same general space, facilitating co-registration of optical and acoustic images and minimizing the amount of space required within the imaging assembly to accommodate more than one modality of imaging. Notwithstanding, the scanning mechanisms can be applied in conjunction with a single imaging modality, such as ultrasound or a single optical imaging technique. Similarly, two or more optical imaging techniques (combined with or without ultrasound) can simultaneously make use of the scanning mechanism on a single probe.

Figure 4A:
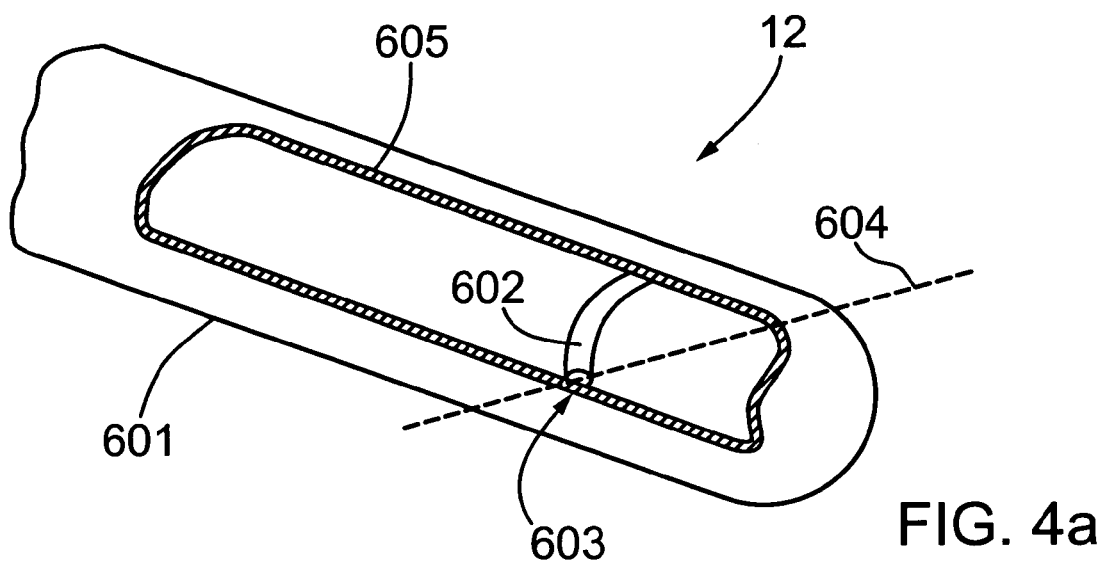
FIG. 4a is a perspective cutaway image of an assembly shell of a distal end section of an imaging probe containing a tiltable component.

FIG. 4a shows a perspective cutaway drawing of the distal region of an imaging probe 12 showing a portion 605 of the outer sheath 601 removed. Located inside the imaging probe 12 is a tiltable component 602, forming part of the imaging assembly, mounted on a pin 603 that extends through the tilt axis 604 of the tiltable component 602.

In several of the embodiments of the present invention that enable scanning of a volume for imaging purposes, the principle of centripetal acceleration is used advantageously. Mechanisms such as motors or cable and pulley systems that directly cause either a transducer to tilt or a reflector to tilt have been proposed in the prior art. Several embodiments of the present invention disclosed herein have the ability to either tilt or deform a component by changing the rotational velocity of the imaging assembly.

Figure 4B:
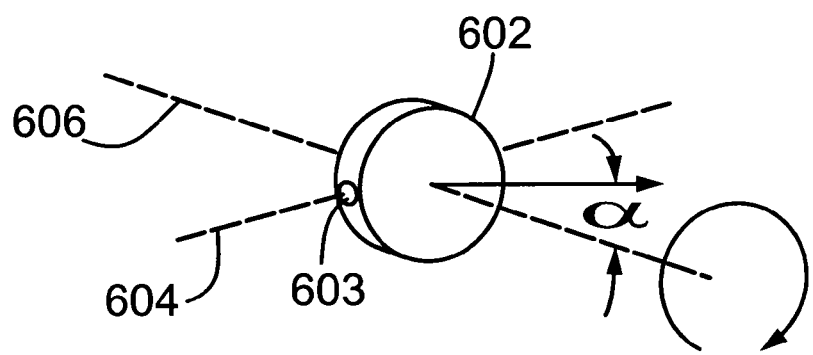

Referring to FIG. 4b, the tilting or deformation of a component is used to change the tilt angle α. The imaging angle is defined as the angle between the longitudinal axis 606 of the imaging probe 12 and the direction in which imaging energy is emitted and/or received. In the present invention, the imaging angle is either a function of the tilt angle α of a tiltable component 602, or the degree of deformation of a deformable component, which can often also be represented by a tilt angle α.

FIG. 4b demonstrates a schematic representation of the tilt angle α relative to the axis of rotation of the tiltable component 602, wherein the tiltable component 602 is shown as a disc that pivots around tilt axis 604. The ability to change the angular velocity of a tiltable or deformable component 602 of an imaging system and subsequently change the imaging angle will be illustrated in the description of the invention below and from our experimental results.

First, the case where the imaging angle is altered by means of a tiltable component 602 will be described. The imaging assembly includes a tiltable component 602 capable of rotating around an axis 604 (the tilting axis) that is substantially perpendicular to the longitudinal axis 606 of the imaging probe. For example, the tiltable component 602 can be mounted on or otherwise associated with a hinge, one or more pins (such as pin 603 mentioned above), a spring or on a deformable substrate to enable rotation around the tilting axis 604. Alternatively, the pins can be replaced by tensile elements, such as wires under tension whereby each wire is anchored to both the tiltable component 602 and another component of the imaging assembly 30, allowing the tiltable component 602 to be suspended in place within the imaging assembly and still enable rotation around the tilting axis 604.

It will be understood that in all embodiments disclosed herein the imaging assembly may be translationally movable within the hollow shaft and may emit anywhere along its length and is not restricted to the distal end of the hollow shaft.

The tiltable component 602 specifically has the property that it has a discrete number of preferred orientations (typically one or two) when the imaging assembly is rotated about an axis other than the tilt axis. Preferably, the axis of rotation of the imaging assembly is substantially coincident with (i.e. substantially parallel and proximate to) the longitudinal axis 606 of the imaging probe. Preferably, the tilt axis is orthogonal to the longitudinal axis. In the absence of gravity or any other forces (such as the restoring forces referred to below) other than the centripetal forces involved in the rotation of the imaging assembly, the tiltable component 602 will orient itself around the tilting axis in a preferred orientation.

FIGS. 4c to 4l illustrate several non-limiting examples of longitudinal and axial cross-sections of tiltable components that would have preferred orientations if they are rotated around the longitudinal axis 606 of the imaging probe 12 in the absence of external forces, in which the tilt axis 604 is substantially perpendicular to the longitudinal axis 606.

Figure 4D:
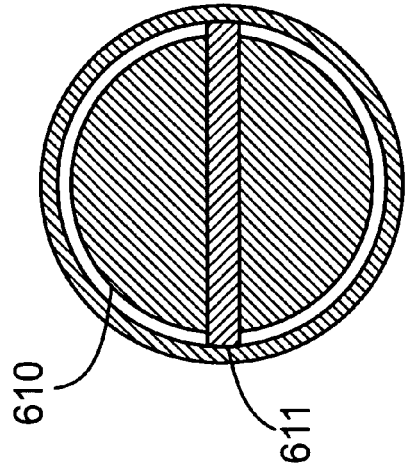
Figure 4F:
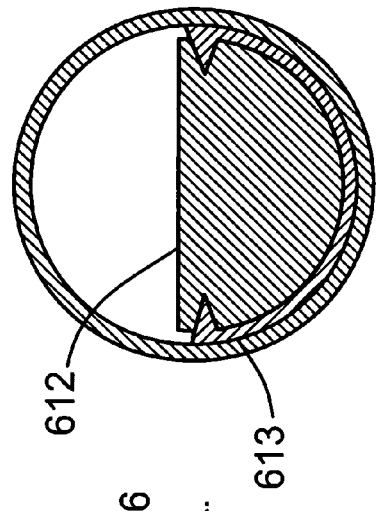
Figure 4C:
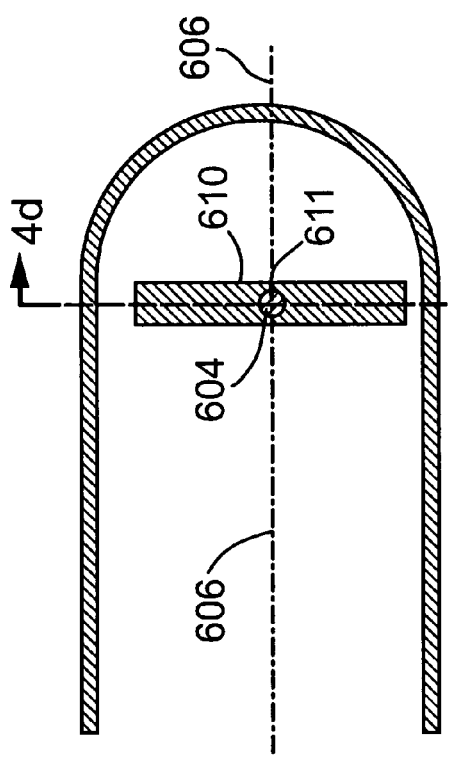

Specifically, FIG. 4c is a longitudinal cross section of an example of an embodiment of an imaging probe where the tiltable component is a disc 610 mounted on a pin 611. FIG. 4d is the corresponding cross-sectional view taken along line 4d-4d.

Figure 4E:
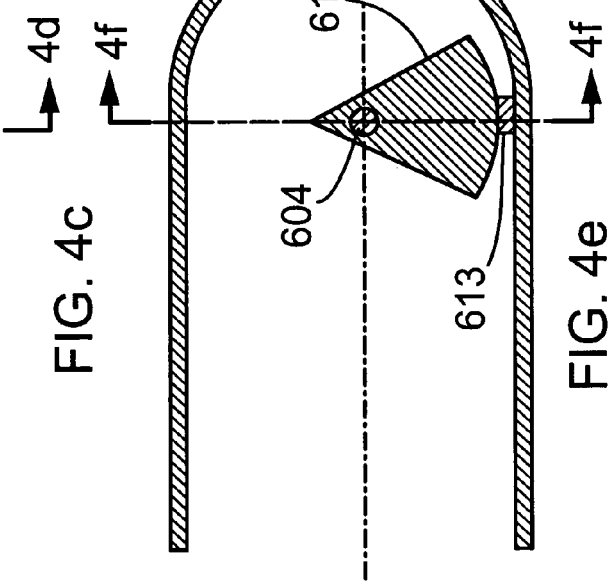

FIG. 4e is a longitudinal cross section of an embodiment of an imaging probe where the tiltable component is a portion of a sphere 612 mounted on a bracket 613. FIG. 4f is the corresponding cross-sectional view taken along line 4f-4f of FIG. 4e.

Figure 4H:
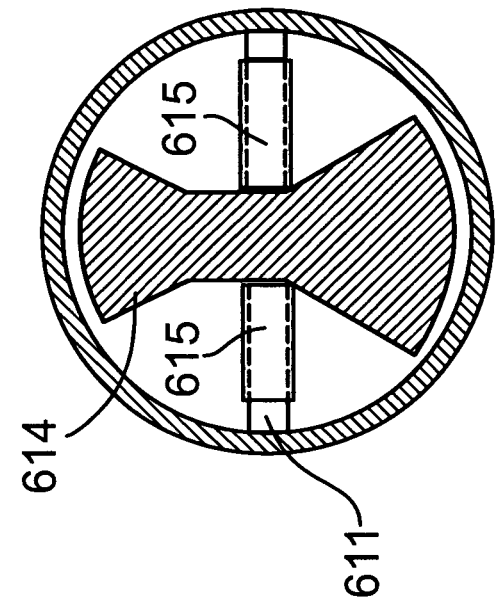
Figure 4G:
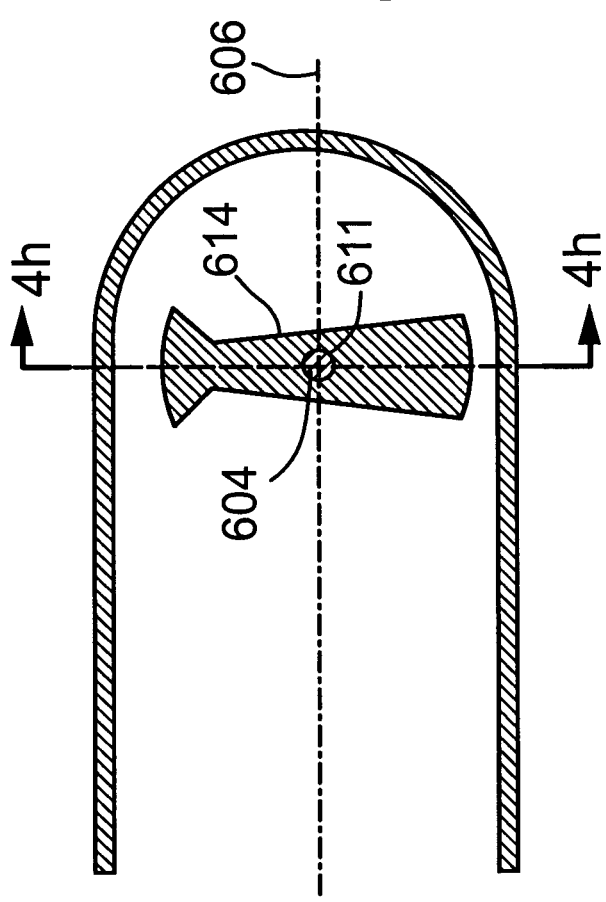

FIG. 4g is a longitudinal cross section of an embodiment of an imaging probe where the tiltable component 614 has a more arbitrary geometry, and is mounted on a pin 611 with spacers 615 (seen only in FIG. 4h) that help to stabilize the position of the tiltable component 614 on the pin 611. FIG. 4h is the corresponding cross-sectional view taken along line 4h-4h of FIG. 4g.

FIG. 4i is a longitudinal cross section of an embodiment of an imaging probe where the tiltable component 620 is mounted by pins 622 so tiltable component 620 pivots about pivot axis 626. FIG. 4j is the corresponding cross-sectional view taken along line 4j-4j of FIG. 4i that shows the pins 622 extending into divots 624 located on the sides of tiltable component 620 that receive the pins 622. The small surface area of the pivot mechanism in this embodiment is advantageous for minimizing friction around the pivot axis 626. Preferably, a pin 622 only contacts the tiltable component 620 near the point of the pin in order to minimize surface contact area.

FIG. 4k is a longitudinal cross section of an embodiment of an imaging probe where a tiltable component 630 is mounted with a pivot axis 632 that does not intersect with the rotational axis 606 of the imaging probe. FIG. 4l is the corresponding cross-sectional view taken along line 4l-4l of FIG. 4k. Functionally, the pivot axis is identical to the tilt axis in the embodiments involving tiltable components.

The functional purpose of the tiltable component 70 is to be able to vary the angle from the longitudinal axis of the imaging probe 31 (FIG. 5a) at which imaging energy (such as a beam of light or acoustic energy) is emitted towards and/or received from the surrounding environment. This can be achieved by mounting an emitter and/or receiver (such as an ultrasound transducer or optical components) on the tiltable component 70. By varying rotational speed of the imaging assembly, the tilt angle will vary and therefore the angle at which the light or acoustic energy is emitted and/or received will vary.

Alternatively, the tiltable component can be used to deflect imaging energy that is emitted and/or received by a component 88 that is not attached directly to the tiltable component 70 as shown in FIG. 5. For example, as mentioned above the ultrasound transducer 88 or optical emitter 92 can direct imaging energy towards the tiltable component 70. The imaging energy is then deflected by an energy deflecting component mounted on the tiltable component 70. For ultrasound imaging, the energy deflecting component (the tiltable component 70) may comprise an acoustically reflective surface, such as a solid metal surface (e.g. stainless steel) or crystalline surface, such as quartz crystal or glass or a hard polymer.

For optical imaging, the energy deflecting component (tiltable component 70) can comprise an optically reflective surface such as a mirror surface made from polished metal, metallized polymer such as metallized biaxially oriented polyethlylene terephthalate (Mylar), sputtered or electrochemically deposited metal, metal foil or other reflective components such as thin film reflectors. Metals commonly used to make mirrors include aluminum, silver, steel, gold or chrome.

Figure 5A:
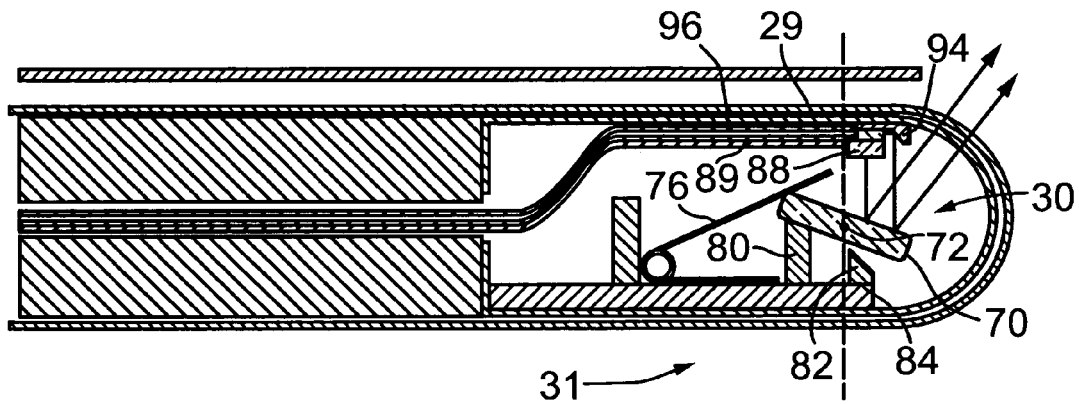
Figure 5B:
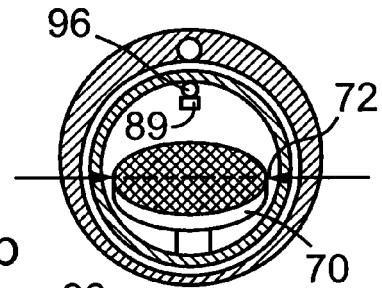

FIG. 5a shows an embodiment of a distal end 29 of an imaging probe 31 containing an imaging assembly 30 that includes a tiltable component 70 where the tiltable component is a disc mounted on pins 72 that enable the disc 70 to pivot about the pin similar to FIG. 4b discussed above. The pins 72 define the tilting axis of the tiltable disc 70. When the imaging assembly 30 is at rest, the disc 70 will remain in an arbitrary starting position. In the example shown, this starting position is defined by a stop 80 that corresponds to a maximal imaging angle, where a restoring force providing by a torsion spring 76 is pushing the disc 70 towards the aforementioned stop 80. FIG. 5b shows a cross section along line 5b-5b of FIG. 5a.

If the tiltable component 70 is tilted away from its preferred orientation by an external force, such as gravity, magnetic forces, electrostatic forces, friction with another moving part or fluid, compressive forces, cantilever forces, normal forces or any other source of incompletely opposed torque on the tiltable component 70 around the tilt axis, the tilt angle will increase.

One or more stops 80 and 82 may limit the range of the tilt angle of the tiltable component 70. For example, stop 80 may be a post or lip extending from the shell 84 of the imaging assembly 30 as a stop to prevent the tilting component 70 from further changing its tilt angle while it makes contact with the stop 80. Therefore, the stop can be used to limit the tilt angle from exceeding a maximum value determined by the position of the stop. Once the tilt angle hits this maximum, the normal force exerted by the stop 80 on the tiltable component 70 opposes the restoring mechanism. In many embodiments, this maximum tilt angle is the tilt angle that is achieved when the imaging assembly 30 is at rest and at low rotational speeds.

An additional or alternative stop 82 can be included to create a minimum tilt angle that the tiltable component 70 will achieve at rotational speeds in the upper end of the operating range. Indeed, there are many situations in which there is no significant benefit in allowing the tilt angle to reach zero, as will become apparent in the following descriptions of specific embodiments.

Figure 5C:
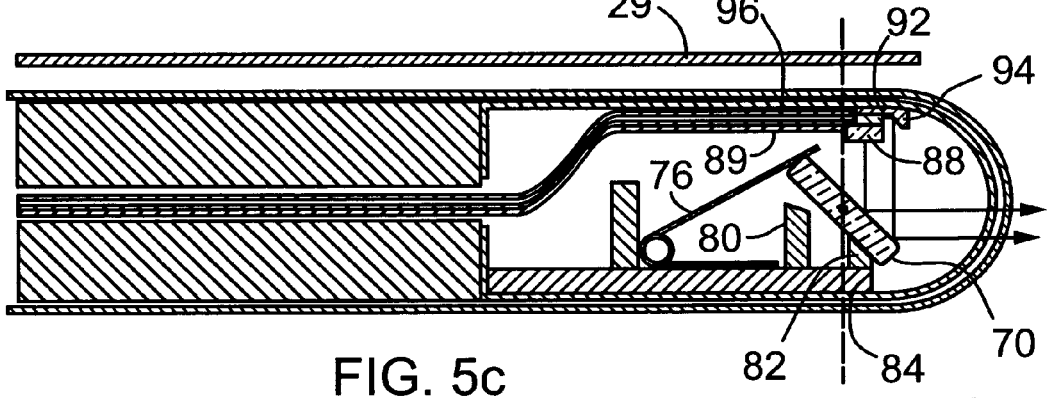

Preferably imaging assembly 30 includes one or more mechanisms that tend to cause the tiltable component 70 to have its tilting angle increase. For the purposes of this invention, such a mechanism is referred to as a restoring mechanism. The torsion spring 76 (as shown in FIGS. 5a and 5c) or a compression spring can be used as a restoring mechanism, where one end of the spring 76 is mechanically in contact with or coupled to the tiltable component 70. The other end is mechanically coupled to another part of the imaging probe 31, such as the body of the imaging assembly.

Figure 5D:
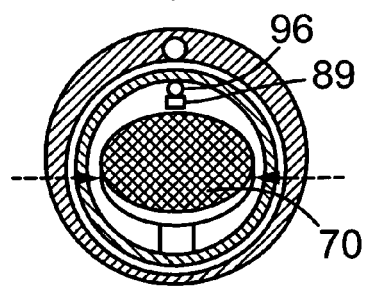

As the imaging assembly 30 rotates, the disc 70 will want to align itself such that the normal of the planes defined by the faces of the disc 70 are substantially parallel with the longitudinal axis. As seen in FIG. 5c, the other stop 82 shown (which corresponds to a minimum imaging angle) will prevent the disc 70 from reaching its preferred orientation at high rotational speeds of the imaging assembly. With a suitably configured imaging assembly, the stop 82 that corresponds to a minimum imaging angle can correspond to an angle of zero, providing imaging in a direction parallel to the longitudinal axis of the imaging probe. FIG. 5d shows a cross section along line 5d-5d of FIG. 5c.

Alternatively, magnetic, electrostatic, hydraulic or other mechanisms that apply a torque on the tiltable component around the tilting axis could be applied. Other examples of mechanisms that could be used to provide a restoring force include tension from an elastomer (such as rubber, polyurethane, silicone, fluoroelastomers, thermoplastics and many others) or by use of a cantilever spring or foil. In very small embodiments of the imaging device, where intermolecular forces such as electrostatic forces and Van der Waals forces between components in the imaging assembly may become quite significant even without the application of an external voltage, the innate intermolecular forces between the tiltable component and structures close to the tiltable component, such as the stops 80 and 82 described below, may be sufficient to provide a net restoring force. For example, a stop comprising a surface made of PVC or LDPE could provide sufficient attraction between the tiltable component and the stop. This is similar to the way that plastic film is used to cover household containers for food storage (i.e. Glad Wrap).

FIG. 5e shows an embodiment of a scanning mechanism for an imaging probe 600 where the torsion spring 76 of FIG. 5a is replaced by a simple cantilever wire 640 in contact with a surface of tiltable component 70 and to a post 787 to create the restoring force. The cantilever 640 may be made of nitinol, platinum, gold or several other suitable materials, including polymers.

Figure 5G:
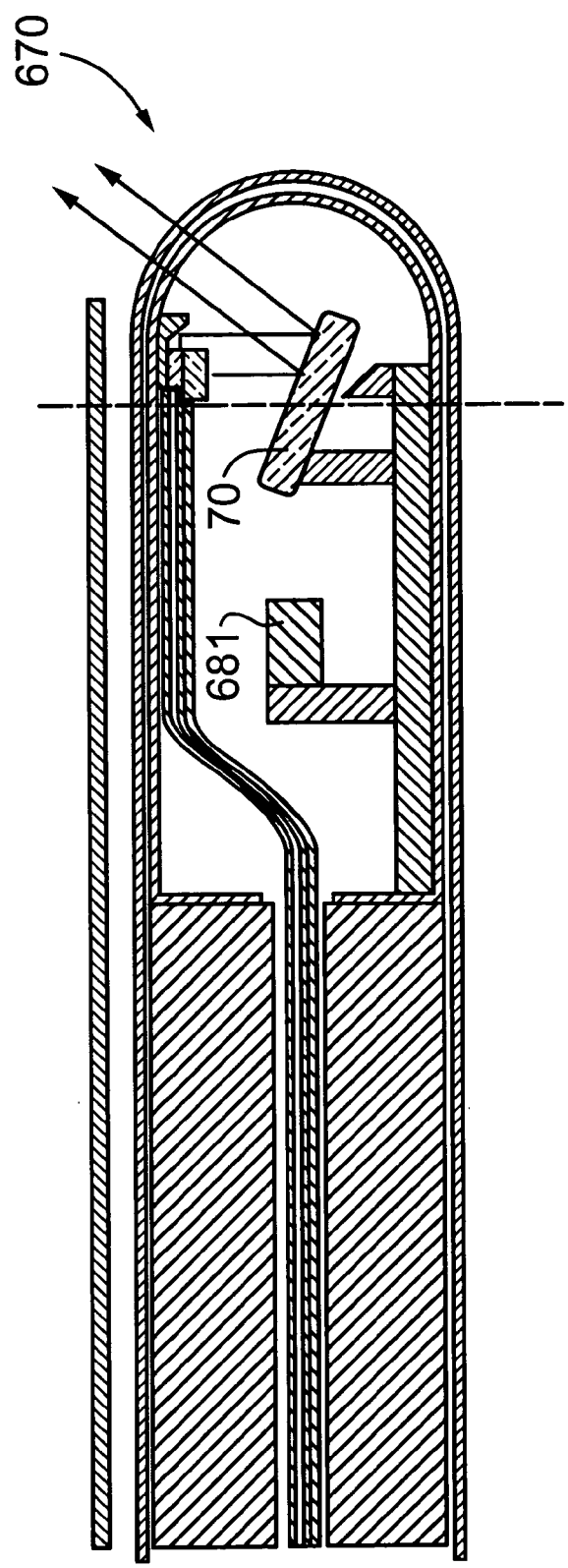

FIG. 5f shows an embodiment of a scanning mechanism for an imaging probe 670 where both the tiltable component 70 comprises a magnet 680 and a non-tiltable component of the imaging assembly comprises a magnet 681 that are used to create the restoring force. The magnets can be oriented such that they either attract or repel one another, depending on their relative positions within the imaging assembly. One of the magnets 681 can be an electromagnet so that its strength can be adjusted or varied as necessary to change the imaging angle. The electromagnet would be powered via conductors (not shown) running from the magnet towards the proximal end of the probe. If the tiltable component 70 has a degree of ferromagnetism, it may not be necessary to have a magnetic component (680 in FIG. 5f) on the tiltable component 70, and one magnet 681 alone may suffice to produce a restoring force, as shown in FIG. 5g.

It should be noted that an electromagnet could be used to deflect the tiltable component 70 and, by varying the current through the electromagnet, produce a scanning pattern for imaging in the absence of any rotational motion of the imaging assembly or imaging conduit.

Figure 5H:
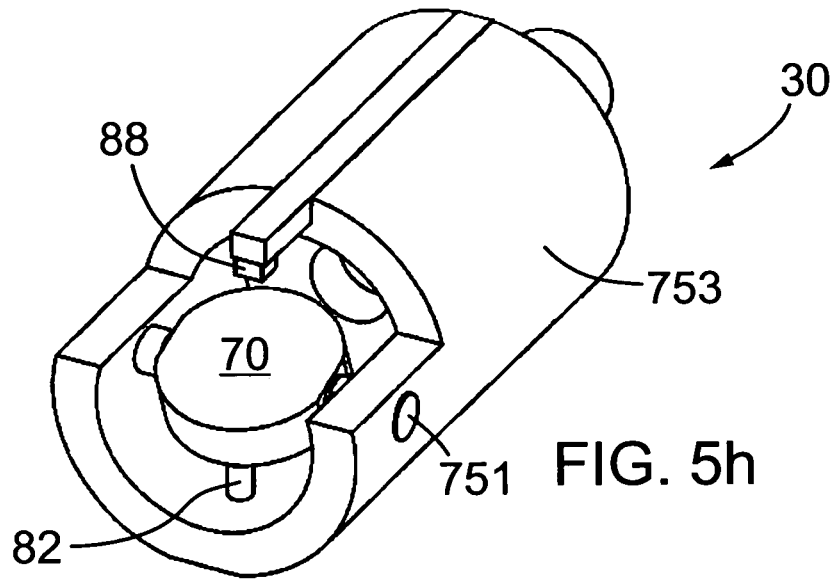
FIGS. 5h and 5i demonstrate collapsed and exploded perspective views of an imaging assembly that could be used to implement the embodiments described in FIGS. 5e to 5g.
Figure 5I:
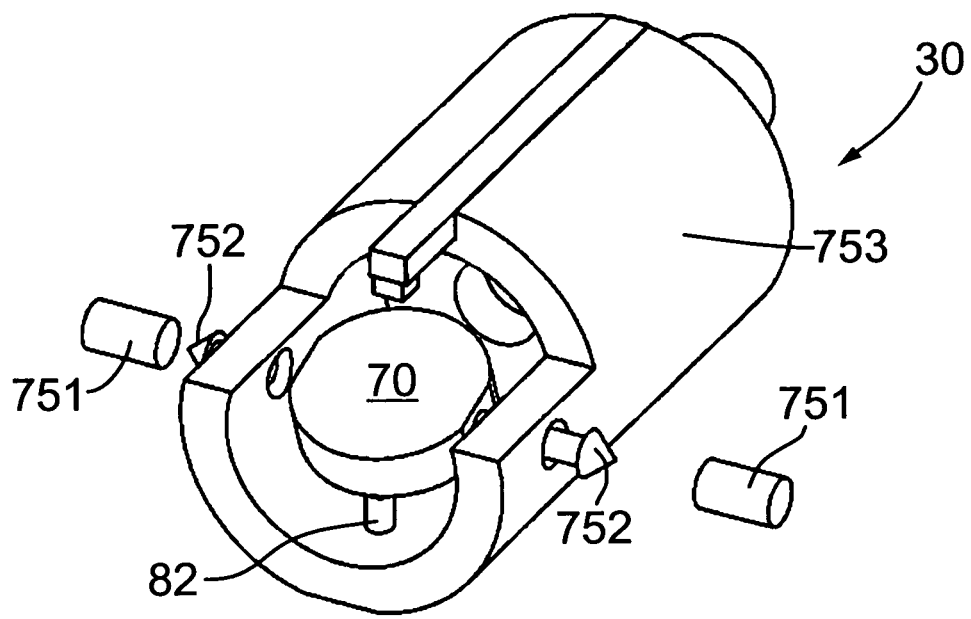

FIG. 5h provides a perspective view of an imaging assembly 30 embodiment, while FIG. 5i provides an exploded view of the same embodiment. A tiltable component 70 acts as a deflector for imaging energy produced by ultrasound transducer 88. Pins 752 are recessed into holes in the side of tiltable component 70 and affixed therein such as by press-fitting or by bonding. In this embodiment, the pins point outwards and are received by a divot (not visible) in each of pin holders 751. During assembly, the pin holders 751 are affixed within the shell 753 of the imaging assembly 30. The pins 751 and the pin holders 752 create a pivot axis on which the tiltable component can pivot with low friction. A stop 82 attached to shell 753 limits the maximum tilt angle of the tiltable component 70. A cantilever spring extends from the back of the shell and is in contact with the bottom surface of the tiltable component so that the tiltable component rests at its maximum imaging angle when there is little or no rotation of the imaging assembly around the longitudinal axis.

Referring to FIGS. 5a to 5g, the imaging assembly 30 may include either optical emitters/receivers and associated directing and focusing optics and/or ultrasound transducers. The ultrasound transducer 88 is mounted at the end of small coaxial cable 89. An optional optical spacer (not shown) and a lens 92 and are mounted at the end of a fiber optic cable 96 adjacent to a mirror 94 in the imaging assembly 30 in FIG. 5a with the optical and ultrasonic emitters configured to transmit imaging towards, and receive imaging energy from, the tiltable component 70. The optional optical spacer is simply a transparent medium, such as glass or polymer, such as a no-clad fiber, that can be interposed in between the distal end of the fiber optic and the lens to improve the working distance or tolerances of the optical imaging system, as described by Mao.

Preferably, the emitter and or receiver is mounted on a component of the imaging assembly that rotates with the imaging assembly. However, it is also possible that the emitter and/or receiver is mounted on a component of the imaging probe that does not rotate with the imaging assembly while the energy deflecting mechanism within the imaging assembly does rotate. This could be achieved by mounting the emitter and/or receiver on an external sheath for example, or by having the imaging assembly divided into two or more sub-assemblies, one of which rotates and includes the tiltable component 70.

The use of an energy deflecting component, as shown in FIGS. 5a to 5i, to vary the imaging angle rather than directly mounting an emitter and/or receiver on a tiltable component (as shown in FIGS. 6a to 6e) may be advantageous. When the transducer is directly mounted on the tiltable component, the tilting action may be impeded by the mechanical properties of the emitter and/or receiver as well as by the mechanical properties of the electrical and/or optical conduits that connect the emitter and/or receiver to the rest of the imaging system. The emitter and/or receiver may be too bulky to be conveniently placed on a tiltable or bendable component.

Furthermore, the use of a reflective surface effectively doubles the change in the imaging angle. For example, a change in the tilt angle of a reflective surface results in a change in the imaging angle that is usually twice the change in tilt angle. Such doubling of the imaging angle can increase the size of the field of view achievable by the scanning mechanism in many embodiments.

In the case of acoustic imaging, it is possible that the application of a strong acoustic pulse onto the acoustically reflective surface will impart some mechanical energy into the tiltable component. This would occur in the event that the acoustically reflective surface does not act as a theoretically perfect reflector and would cause the tiltable component, or some subcomponents of the tiltable components to vibrate. Such vibrations might contribute to artifacts in any images made, especially if the energy of such vibrations were to be directed back towards the acoustic receiver. Therefore, it may be necessary to include a dampening mechanism in the tiltable component. Materials suitable for backing an acoustic ultrasound transducer, such as epoxy with tungsten powder mixed within, could be used for this purpose. The dampening mechanism could be an additional layer within the tiltable component, or could be incorporated into the design of the hinge or pin that that tiltable component is mounted upon, such as by adding a layer of a dampening material to the pin, or into any holes in the tiltable mechanism that accept a pin.

Referring to FIGS. 5a to 5g, the imaging assembly 30 may include counteracting springs or other such mechanisms to produce a lower restoring force than would occur without a counteracting mechanism. For example, if the restoring force produced by a restoring mechanism such as a spring 76, cantilever wire 640 or magnet 681 is too much to overcome by centripetal acceleration alone, than a counteracting mechanism such as another spring, wire or magnet, can be used to urge the tiltable component in the same direction that it would tilt under centripetal acceleration. The use of such a counteracting mechanism can reduce the net restoring force. For example, a first torsion spring 76 made of wire can be used as a restoring mechanism. A second torsion spring, configured to counteract the restoring force of the first torsion spring can be added to reduce the net restoring force for the tiltable member.

FIGS. 6a to 6e illustrate a distal end of an imaging probe containing imaging probes capable of acoustic imaging where the scanning mechanism includes an acoustic transducer directly mounted on a tiltable component. More particularly, FIG. 6a shows an embodiment of an imaging assembly 300 that comprises a tiltable component 302 that is pivotally mounted on a pin 312 and upon which an acoustic transducer 304 is mounted. A stop 306 defines the maximum imaging angle that can be achieved. A pair of electrically conducting elements 308 extend from the imaging conduit 34 to the acoustic transducer 304. The conducting elements 308 are preferably of a very flexible composition such as thin coaxial wires or of a thin film composition that allows for one or more conducting pathways within the thin film. As a result of their mechanical properties, the conducting elements 308 may provide a restoring mechanism whereby the conducting elements 308 tend to force the tiltable component 302 into a configuration with a maximum tilt angle. Alternatively, an additional spring or other restoring force may be used to contribute to the net restoring force. Furthermore, an additional spring or other restoring force can be used to reduce the net restoring force. For example, if the restoring force produced by conducting elements 308 is too much to overcome by centripetal acceleration alone, a spring or other mechanism that urges the tiltable component to tilt in the same direction that it would tilt under centripetal acceleration can reduce the net restoring force.

For example, as in FIG. 6a, the stiffness of the conducting elements 308 provides sufficient force to cause the tiltable component 302 to rest against the stop 306 and therefore to achieve a maximum imaging angle for the particular embodiment. This angle would be achieved while the imaging assembly 300 is not rotating or is rotating at low angular velocity around the longitudinal axis of the imaging probe. The imaging assembly 300 shown in FIG. 6b demonstrates how the tiltable component 302 would tend to align itself into a preferred configuration when the angular velocity is increased and therefore change the imaging angle.

It can be appreciated that while the imaging angle and the tilt angle demonstrated in FIGS. 6a and 6b are substantially equal, the acoustic transducer 304 can be mounted onto the tiltable component 302 so that the imaging angle and tilt angle are offset. For example, the geometric configuration of the tiltable component 302 can include a beveled surface onto which the transducer 304 is mounted, or a shim can be included between the transducer 304 and the tiltable component 302 to offset the imaging angle and tilt angle. It can also be appreciated that other restoring mechanisms can be included with the embodiment presented in FIGS. 6a and 6b. The acoustic transducer 304 can also be recessed within the tiltable component 302, as seen in FIG. 6C.

For certain embodiments, the connection of conductors from to an acoustic transducer on the tiltable component may result in the conductors being too rigid to allow the tiltable component to tilt with adequate fidelity for the desired application. The use of an inductive coupler can be used in such circumstance, as described by Maroney et al in U.S. Pat. No. 5,373,849. Alternatively, one or more parts of the pivot mechanism, such one or more of the pins of the pivot mechanism for the tiltable component can serve a second purpose as electrical contacts to electrically isolated conductors on the tiltable component.

FIGS. 6d and 6e illustrate the use of pins 310 that are electrically connected to the coaxial cable to provide electrical contacts to conducting paths within the tiltable component 302 to provide connections with the transducer 304 on the tiltable component 302. The electrically conductive paths may be insulated within the core of the pins 310 except at the tips of the pins 310 where they come into contact with the tiltable component 302. Similarly, the indentations of the tiltable component for receiving the pins 310 may be electrically insulated except at their points of contact with the tips of the pins 310. In this circumstance, the fluid in the vicinity of the tiltable component 302 may optionally comprise a fluid that has lower conductance than saline, such as distilled water or mineral oil. Alternatively, o-rings may be used to improve electrical isolation at the electrical contact points.

Alternatively, the conducting elements 308 can be replaced by a fiber optic and the acoustic transducer 304 can be replaced by one or more optical receivers and/or emitters.

Alternatively, the tiltable component 302 can be suspended by two or more tension elements, in place of pins 310. For example, a thin wire anchored to tiltable component 302 can replace a pin 310. The thin wire can be mechanically coupled to the imaging assembly or shell 753. By having two such wires on opposing sides of tiltable component 310, and applying some tension to the wires while mechanically coupling the wires to the shell 753, the tiltable component will have a similar tilt axis around which it can tilt. The tensions wires may also serve as conducting elements 308 to transmit electrical signals to the transducer 304.

FIGS. 6f to 6j demonstrate the distal end of an imaging probe capable of optical imaging where at least a portion of an optical emitter and/or receiver is mounted directly on a tiltable component. In FIGS. 6f and 6g the energy deflecting component is made of a transmissive refractive element 392, such as glass, clear polymers, and many others, and deflect the imaging energy in a manner similar to a prism or lens. Light from fiber optic 391 mounted within imaging assembly 30 emits light towards the refractive element 392 mounted on tiltable component 70. The distal end of the fiber optic may terminate with an optical spacer or GRIN lens, as shown in other figures in the present invention. In the embodiment of FIGS. 6f and 6g only a portion of the optical emitter and/or receiver is mounted directly on a tiltable component. The transmissive refractive element 392 is not directly attached to the distal end of fiber optic 391 making it easier for the tiltable component 70 to tilt without hindrance from any mechanical influence from the fiber optic 391.

In FIGS. 6h to 6j the complete distal end of an optical emitter and/or receiver, including distal end of fiber optic 391 is mechanically coupled with the tiltable component 70. The fiber optic 391 may also act as a mechanical component providing a restoring force to tilt the tiltable component 70 at its maximum tilt angle, as shown in FIG. 6h. At higher rotational speeds, the tiltable component 70 will tend to align as shown in FIG. 6i. FIG. 6 provides a front view of the imaging assembly 30.

Alternatively, the conducting elements 308 and fiber optics 391 in FIGS. 6a to 6j can be replaced by a combination of conducting elements 308 and one or more fiber optics 391 while the acoustic transducer 302 is replaced by a combination of conducting elements 308 and one or more fiber optics 391. It is appreciated that increasing the number of conducting elements 308 and/or fiber optics in certain embodiments may impact the range of imaging angles that can be achieved by the tiltable component as a result of the increased stiffness of the conducting elements 308 and/or fibers.

For certain embodiments a rotary optical joint may be included in the pivot mechanism, such as by including a fiber through a pin and a pin-receiving element. While such a rotary joint for single mode fiber optic transmission would require considerable precision (for alignment of fibers with diameters on the order of 4-12 microns), a rotary joint suitable for coupling of optical lightpaths with dimensions similar to those found in multimode fibers (diameters on the order of 50 to 250 microns) would be easier to implement. Planar lightwave circuits (such as those available from Grintech, Germany), free space channels, prisms and lenses can be used to direct light through components incorporated with the tiltable component to direct the light in a manner suitable for optical imaging, such as for OCT, angioscopy, infrared imaging, near-infrared spectroscopy and fluorescence imaging.

There are further alternative embodiments in which varying the rotational velocity of the imaging assembly could be used to vary the imaging angle. Rather than causing a tiltable component to tilt around a pivot axis, a bendable component can be used to carry an emitter and/or receiver or to carry an energy deflecting mechanism. The bendable component comprises a structural assembly that is constrained at one or more points along its length with respect to its radial distance from the rotational axis of the imaging assembly, but is not constrained over a substantial portion of its length.

For the purposes of this description, a "radially constrained" portion of the bendable component is meant to refer to a portion of a bendable component that has a relatively fixed distance from the rotational axis of the imaging assembly. Similarly, a "radially unconstrained" portion of the bendable component is referring to a portion of the bendable component whose radial distance from the rotational axis of the imaging assembly can vary as a result of centripetal motion, gravity, electrostatic forces, magnetic forces and others. The structural assembly may comprise a thin, elongate portion of bendable plastic, wire, foil or even a rod made of fiber optic. It may comprise collection of subcomponents of varying mechanical properties in terms of strength, elasticity, mechanical hysteresis to deformations and others.

The principle of operation for the use of a bendable component to vary an imaging angle is that as the imaging assembly rotates, the bendable component will bend as a result of centripetal acceleration. Different portions of the bendable component may bend in different directions or to a different extent for a given rotation, depending on many factors including the mechanical properties of the bendable component and subcomponents, as well as the geometry of the bendable component. For the purposes of illustration, the bendable component can be modeled as a collection of infinitesimally small volumes, referred to as voxels. Voxels within radially constrained portions of the bendable component will maintain their approximate distance from the rotational axis, while voxels in the radially unconstrained portions will tend to travel in a direction tangential to their roughly circular path as a result of inertia.

Internal forces within the bendable component (tension, compression etc.) will usually prevent the voxels from following a completely tangential path. The shape that is assumed by the bendable component will depend greatly on the material properties and geometry of the bendable component, but it will change shape as the rotational velocity changes. Examples of different geometries and the anticipated changes in shape are described below. There may be optional components added along the length of the bendable component that will adjust the bending properties of the bendable component as a result of their mass while being rotated. The weighted components may serve to simply adjust the bending properties of the bendable component, or they may also serve a functional purpose, such as acting as an deflecting component that deflects imaging energy.

An example is now provided of an imaging assembly where an imaging axis is varied as a result of a bendable component. Consider a bendable rod that is fixed to the imaging assembly at the proximal end of the bendable rod, but is otherwise not attached or anchored to the imaging assembly. At rest, the longitudinal axis of the bendable rod lies roughly parallel to the rotational axis, and may be slightly offset from the rotational axis. As the imaging assembly rotates, each voxel in the unconstrained portion of the bendable rod will gradually increase its distance from the rotational axis. The rod will assume a bend in its curvature in the radially unconstrained portion of the rod. This is made useful for imaging purposes if the bendable rod is a fiber optic through which light is being emitted and/or received. As the rod bends, the imaging angle will vary.

There may be a lens at the distal end of the fiber optic, which would be a weighted component that would result in increasing the degree of curvature of the bendable rod at a given rotational velocity. Optionally, additional weights, such as a stainless steel cylinder or ring could be added to further increase the degree of curvature. Similarly, the rod could be made useful for imaging purposes if the bendable rod is a flexible conduit that contains conductive wires for transmitting electrical signals to and from an ultrasound transducer. The ultrasound transducer would be a weighted component that would result in changing the degree of curvature of the bendable rod at a given rotational velocity. The bendable component could be reinforced by other materials to alter its mechanical properties. For example, a thin nitinol rod could be used to reinforce a fiber optic or electrical conduit to reduce the degree of curvature incurred at a given rotational velocity and improve the predictability of the bendable component returning to a straighter configuration when at rest. In this example, the emitter and/or receiver of imaging energy is mounted directly on the bendable component.

The bendable component may comprise several different geometries, including circular, square or rectangular rods as well as thin films and foils. It may alternatively or additionally comprise helical or spiral shaped geometries such as found in compression springs. Materials used would ideally have a degree of elasticity that allows them to predictably and repeatably return to their starting position. Examples would include polymers, including polyimides and polyurethanes, as well as silicones, rubber and many other materials. Metals with good elasticity include nitinol, brass, gold, silver, platinum, steel, and many others. The degree of elasticity required as an innate property of the material will vary significantly depending on the geometry of the material in the bendable component. For example a given material may not have sufficient flexibility or elasticity while in the form of a square rod, but if incorporated into a spring-shaped component, may have both sufficient flexibility and elasticity.

Figure 7A:
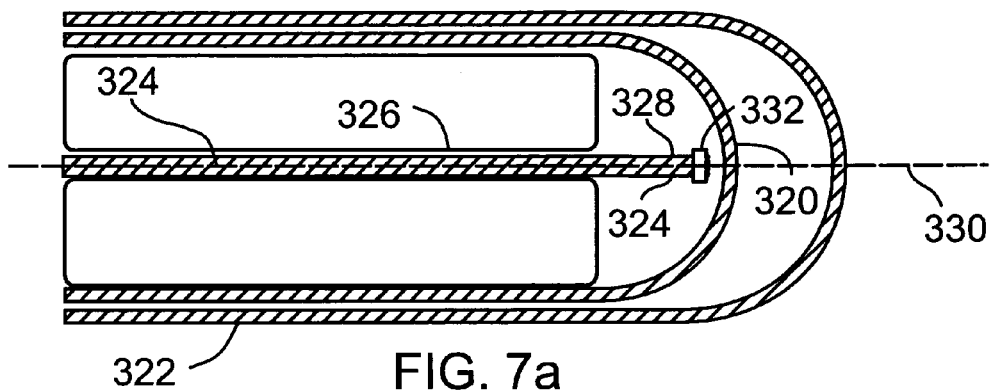
FIGS. 7a to 7c demonstrates an example of the distal end of an imaging probe capable of acoustic imaging where a deformable component carries either an emitter and/or receiver of imaging and/or therapeutic energy. The imaging angle varies as a function of the rotational velocity of the imaging assembly.
Figure 7B:
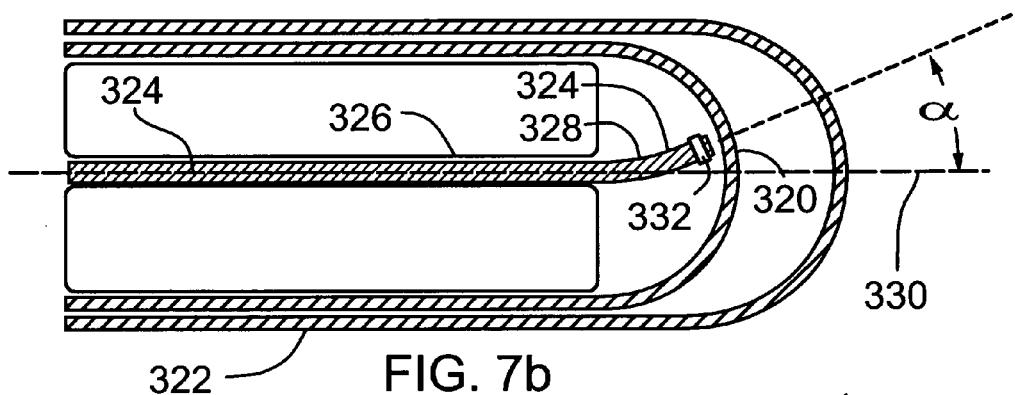
Figure 7C:
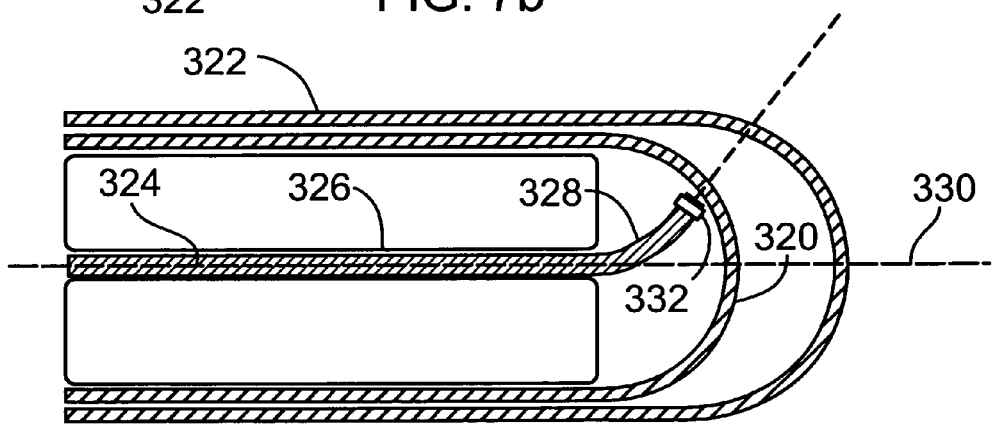

FIGS. 7a to 7c show an embodiment of an imaging assembly 320 near the distal end of an imaging conduit 322. A deformable component comprises a fiber optic 324 that has a substantially unconstrained portion 328 near the distal tip of the fiber 324 and a substantially constrained proximal portion 326. In these FIGS. 7a to 7c, the constrained portion 326 lies within the bulk of the imaging conduit 322, while the unconstrained portion 328 lies distal to the imaging conduit 322. When the imaging probe is not rotating, as in FIG. 7a, the fiber 324 tends to minimize internal stresses, which in this example is shown to cause the fiber 324 to assume a generally linear configuration. However, as the imaging conduit 322 and the fiber 324 within are rotated around the longitudinal axis 330, as in FIG. 7b, the centripetal acceleration experienced by the fiber 324 will cause the unconstrained portion 328 of the fiber 324 to deform from the resting position and change the imaging angle. Further increase in the rotational velocity can cause further changes in the imaging angle α, as seen in FIG. 7c. The use of one or more optional weighted components 332 may increase the amount of deformation achieved at a given rotational velocity. An acoustic transducer can replace or accompany the optical imaging emitter/receiver.

Figure 8A:
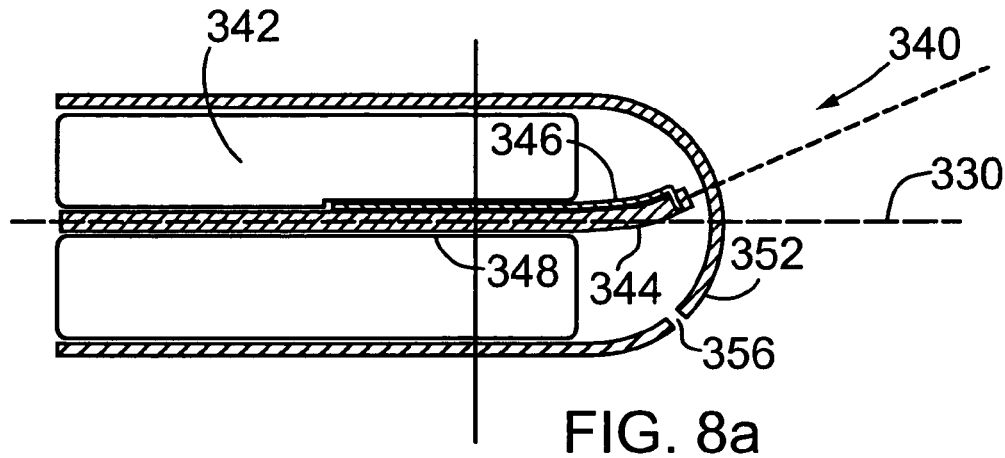
FIGS. 8a and 8b demonstrate an example of an imaging probe where the deformable component is reinforced by an elastic supporting structure and the imaging assembly and external sheath have optional flush ports.
Figure 8B:
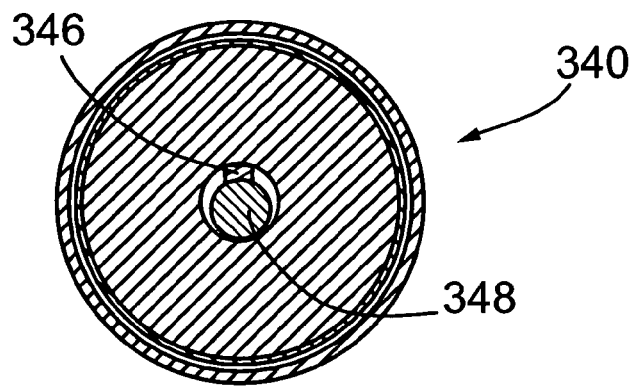

FIG. 8a shows an embodiment of an imaging assembly 340 near the distal end of an imaging conduit 342 where the deformable component 344 is associated with an elastic support member 346. The mechanical properties of a deformable component, such as an optical fiber 348 when the imaging sensor is an optical based system, are such that they may not tend to sufficiently restore the fiber 348 to a resting configuration such as a straight configuration. Therefore, the use of an elastic support member 346, such as a length of nitinol wire can be associated with the distal region of the deformable component to improve the performance of embodiments that contain a deformable component 346. FIG. 8b shows an axial cross-section of the embodiment 340 that contains elastic support member 346. The deformable component 344 can be used to facilitate either optical or acoustic imaging or both.

Additionally, optional flush port 356 in sheath 352 of the imaging conduit 342 of imaging probe 340 are shown in FIG. 8a. Port 356 serves to facilitate flushing of the imaging probe 340 with a desired fluid medium, such as water or saline, in combination with one or more flush ports near the proximal end of the imaging probe, as seen in FIG. 2. Flush ports may be optionally included all the embodiments of the present invention.

Figure 8C:
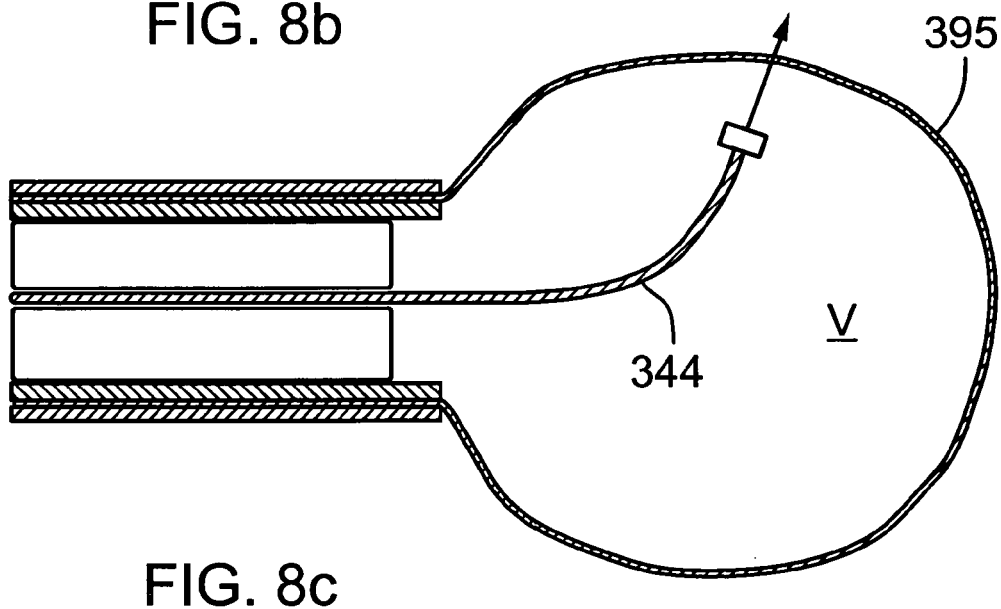
FIGS. 8c and 8d demonstrate an example of an imaging probe where the deformable component is surrounded by an expandable balloon that provides a protected region in which the probe can move while the balloon is expanded.
Figure 8D:
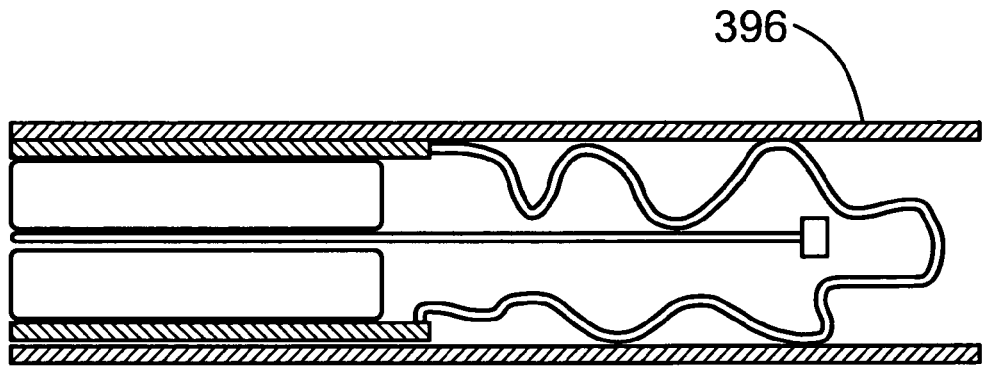

FIGS. 8c and 8d depict an embodiment wherein the distal end of the imaging probe 30 comprises an expandable component 395. The expandable component 395 serves the purpose of provide a larger safe volume V within which the deformable component can deflect at higher rotational speeds without coming into contact with anatomic structures. The expandable component 395 may be inflatable via a separate inflation lumen (not shown) or via the imaging conduit lumen. As seen in FIG. 8d, an additional external sheath 396 may be included to slide over the expandable component 395 during delivery or removal of the imaging probe.

Figure 9A:
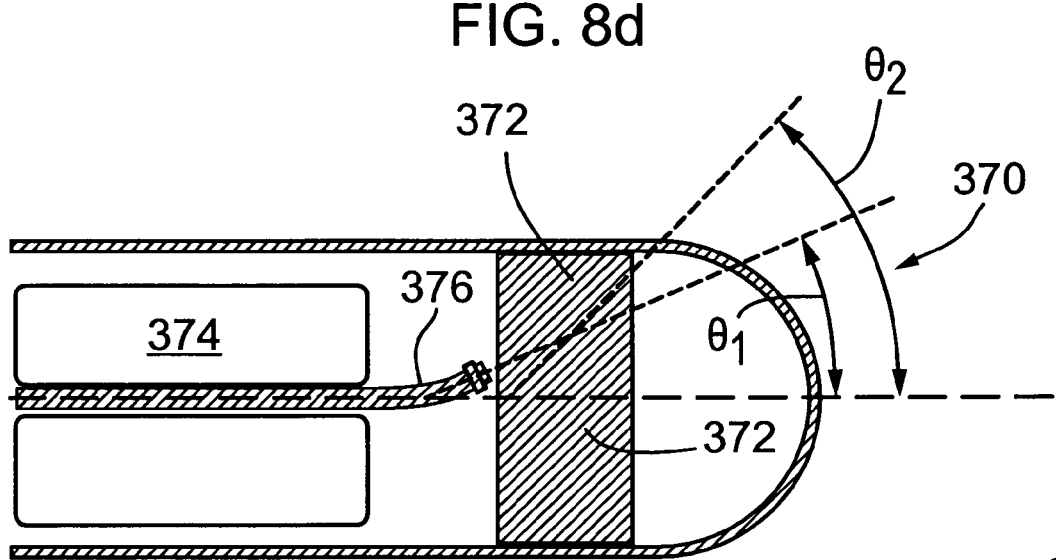
FIGS. 9a and 9b demonstrate the use of a GRIN lens or a refractive medium to amplify the imaging angle achieved.

FIG. 9a shows an embodiment of an imaging probe 370 which uses a GRIN lens 372 (gradient index of refraction lens) to increase the imaging angle achieved with optical imaging. The GRIN lens 372 is located near the distal end of the probe after the imaging conduit 374 which contains a fiber optic 376. The GRIN lens 372 is placed adjacent to the distal end of fiber optic 376. GRIN lenses can be selected that have the property whereby a displacement of a distal end of the fiber 376 that emits light towards one end of the lens 372 results in a change in the angle at which the light emitted from the other end of the lens. Light received from by the lens 372 from the imaged tissue is focused in a reciprocal fashion back towards the fiber 376 along the same path in which light emission occurs. The original imaging angle $\theta_1$ is shown in FIG. 9a, while the presence of the GRIN lens 372 results in the larger effective imaging angle $\theta_2$, also shown in this figure. This is helpful as many of the deformable components may have limitations in the range of imaging angles achieved due to the properties of several deformable components such as flexibility and geometry. For example, the fiber optic 376 has a minimum radius of curvature that can be obtained before the fiber breaks or loses performance. Also, the desire to miniaturize the imaging assembly for many of the imaging probes for intravascular use results in geometric constraints on the deformable components. Using a GRIN lens 372 can help amplify the range effective imaging angles that can be achieved under these circumstances.

Figure 9B:
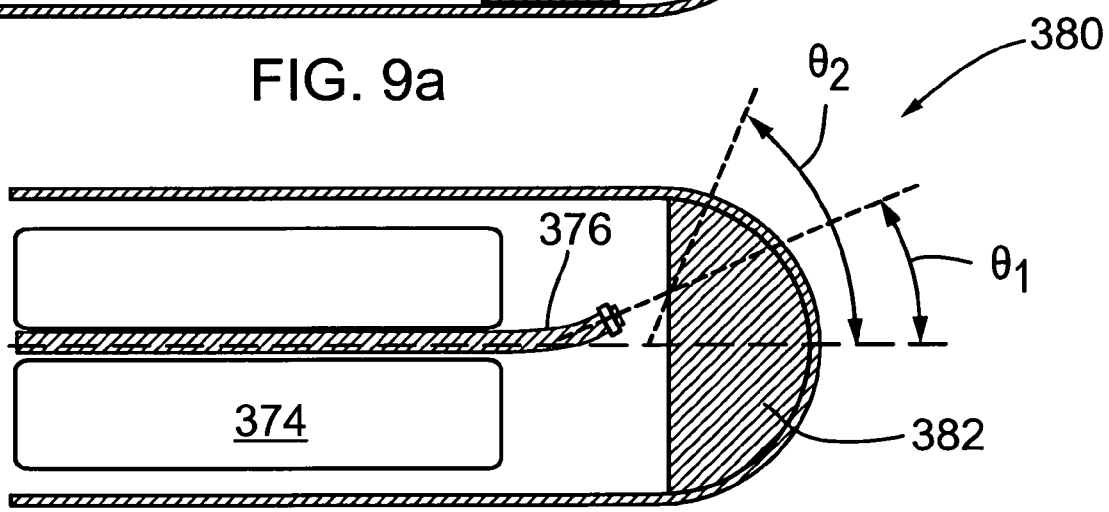
Figure 11A:
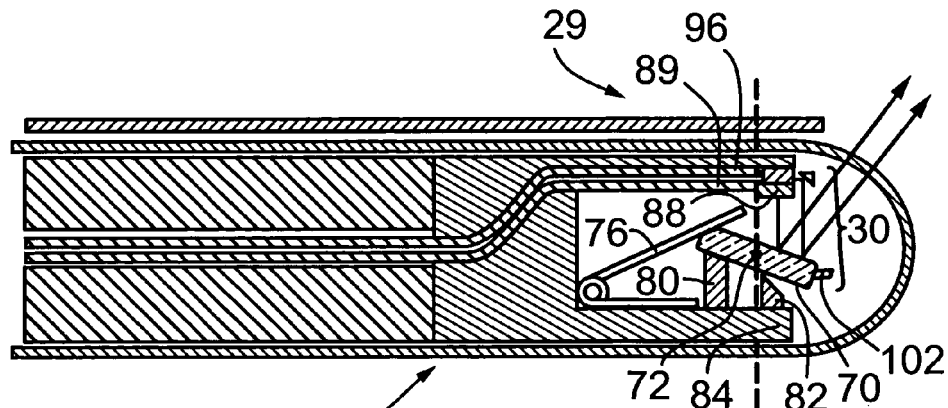
FIG. 11a-11d is an example of a tiltable component where the tilting action is modulated and preferably augmented by including one or more structural features on the tiltable component to act as wings within the fluid medium of the imaging assembly.
Figure 11B:
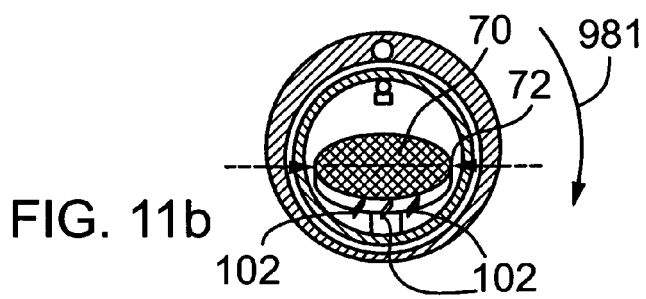
Figure 11C:
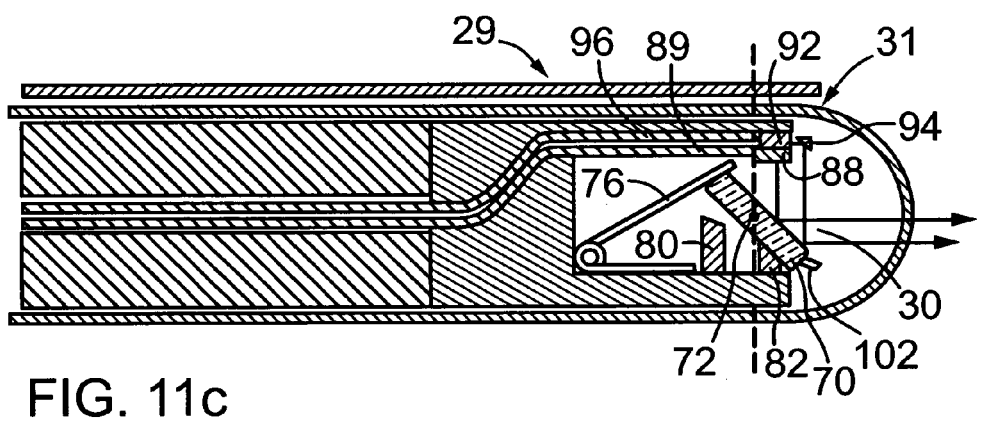
Figure 11D:
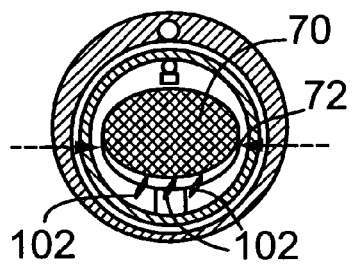

Other transmissive optical elements can be added to amplify the effective imaging angle. For example, a hemisphere 382 made of a medium with an index of refraction less than the index of refraction within the imaging assembly 380 shown in FIG. 9b. Such an element 382 may comprise a gas-filled chamber, such as a carbon dioxide filled chamber, or it may be a chamber filled with air. If the index of refraction of the low index medium is not strongly dependent on wavelength, the effects of dispersion will be minimized. Similarly, if the light used for imaging spans a narrow spectrum of wavelengths, the effects of dispersion will be minimized.

A bendable component may be used in combination with an imaging energy deflecting component to change an imaging angle. At least one emitter and/or receiver is oriented to direct imaging energy towards the energy deflecting component and/or receive imaging energy from the energy deflecting component.

An example of an imaging assembly comprising an energy deflecting component mounted onto a bendable component within a rotating imaging assembly is provided in FIG. 10.

FIG. 10 shows an embodiment of the probe at 120 in which an energy deflecting component 122 is mounted onto a deformable component 124 to enable imaging at different angles, dependent on the speed of rotation. In the top image, the deformable component 124 holds the deflecting component 122 at an angle that causes a large imaging angle. As previously described for deformable components, the deformable component 124 can be a foil, a spring, a metal or polymer element, such as a nitinol rod and several other. In order to accentuate the deformation incurred at a given rotational velocity, an optional deflector weight 128 can be added to either the deformable component or other elements mounted to the free end of the deformable component 124, such as the deflecting component 122. While in this particular embodiment the imaging angle could potentially be derived from the OCT imaging circuitry, a strain gauge 130 and connection 132 for a strain gauge is shown. The strain gauge 130 enables an alternative mechanism for estimating the imaging angle. At high rotational speeds, the deformable component 124 would tend to bend as shown in FIG. 10b.

FIG. 11 shows another embodiment of an imaging probe at 100 that can be used to cause the rotational velocity to affect the imaging angle is the use of one or more hydrofoil elements, such as a wing, on the deflectable or tiltable component. Mechanism 100, which is very similar to probe 31 in FIG. 5, has three wings 102 affixed to the distal edge of a disc-shaped deflectable component. As the rotational velocity is increased in the indicated direction 981, the wings will create a pressure gradient to take effect that will, in the present example, cause the imaging angle to increase. Also in this figure, note how the imaging assembly need not necessarily have a shell completely surrounding the components of the imaging assembly. Removing the shell, or parts thereof, minimizes the bulk of the imaging assembly 30. Also, in the case where one or more hydrofoil elements are incorporated into the design, it may be advantageous to have the fluid in which the hydrofoils travel be in direct fluid communication with a non-rotating surface, such as the external sheath. By having such fluid in direct communication with the external sheath, the fluid will generally develop a flow pattern where the velocities of the fluid within this region are reduced by drag secondary to the relatively static surface of the external sheath. This will increase the relative speed through which the "wings" travel through the fluid and thus increase the lift generated by the wings.

Figure 12:
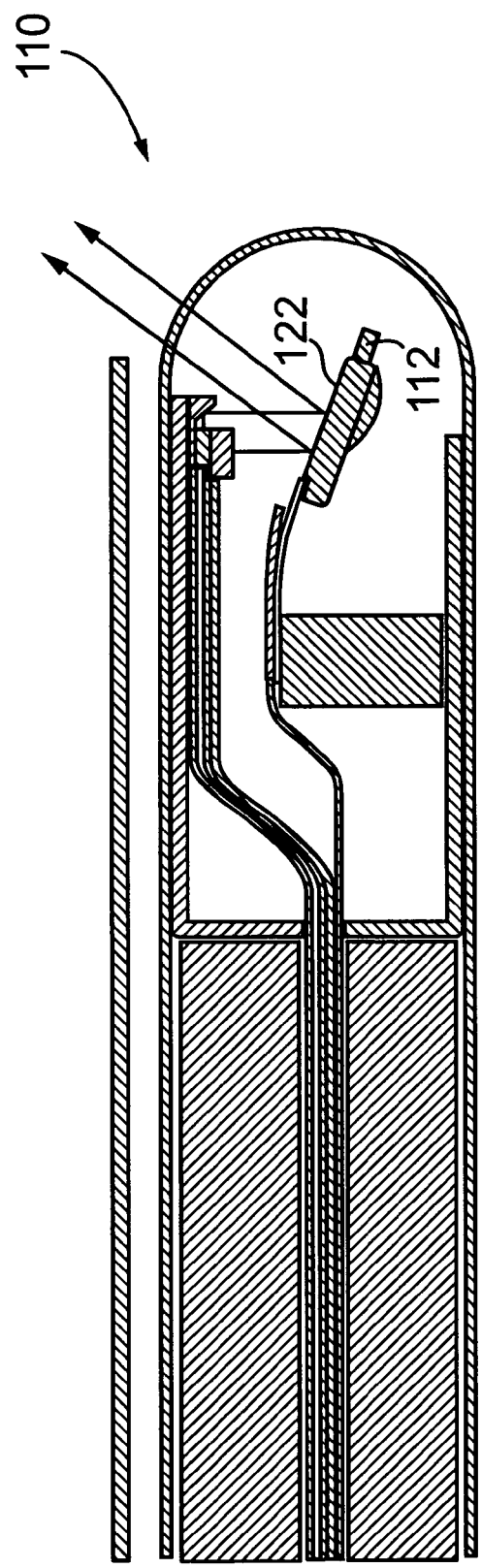
FIG. 12 is an example of a deformable component where the deformation is modulated and preferably augmented by including one or more structural features on the tiltable component to act as wings within the fluid medium of the imaging assembly.

Similarly, FIG. 12 shows an embodiment of a probe at 110 similar to probe 120 in FIG. 10 in which the deflecting component 122 includes wings 112 which give the same result as with the probe 100 having the wings on the tiltable element 70.

In some uses, the rotational speed will be changed in a stepwise fashion, while in others, the rotational speed will be swept through a range of speeds. The desired scanning patterns and the related functions of rotational speed required to achieve those scanning patterns will be strongly dependent on the application. For example, if the desired scanning pattern is to scan a volume that approximates the surface of a cone, a particular rotational speed might be actuated by the rotational motor. The pitch of the cone can be changed by changing the rotational speed. If the desire is to scan an entire volume, multiple cones can be imaged by stepwise changing the rotational speed, or the scanning volume can include a spiral path by sweeping through a range of rotational speeds. Multiple other scanning patterns can be achieved by varying the rotational speed over time.

Figure 13A:
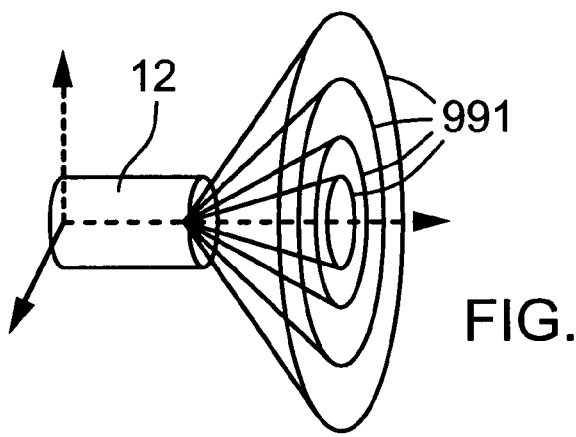
FIGS. 13a and 13b are examples of some forward looking scanning patterns that can be achieved by the present invention.
Figure 13B:
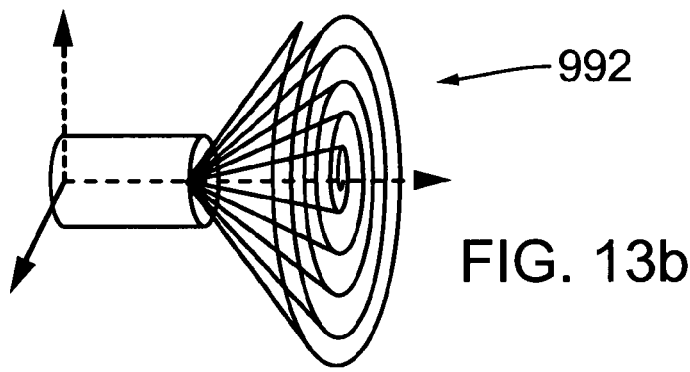
Figure 13C:
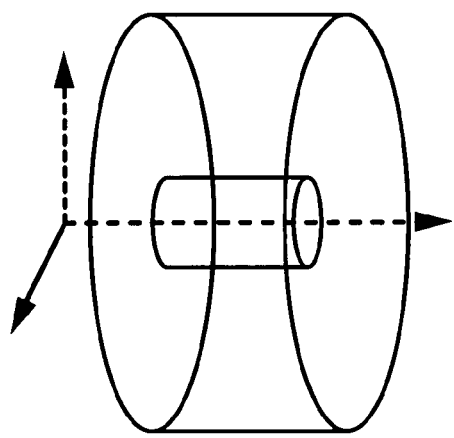
FIGS. 13c and 13d are examples of a side viewing volume that can be imaged by the present invention.
Figure 13D:
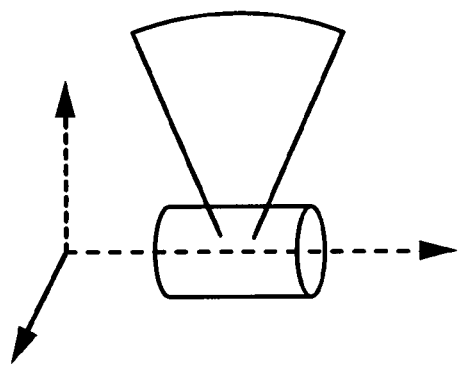

FIG. 13a shows an example of one of the many scanning patterns that can be achieved by several of the embodiments of the present invention. The imaging assembly 12 is shown along with Cartesian coordinate axes. A volume of interest can be imaged by rotating the imaging conduit and imaging assembly. By varying the imaging angle in a step wise fashion and acquiring imaging data over one or more revolutions at different imaging angles, imaging data is collected along the surfaces of a series of concentric cones 991. Such a scanning pattern is simpler for image reconstruction purposes, but would be suboptimal with respect to the acquisition time of the imaging data. FIG. 13b demonstrates an example of a scanning pattern where the imaging beam follows a more spiral-like path 992 by having the imaging angle vary continuously while the imaging probe is rotated. Such a scanning pattern may increase the complexity of algorithms to reconstruct 3D imaging data, but would be more time efficient with respect to data acquisition than the pattern in FIG. 13a.

Current intravascular imaging methods typically estimate a rotational angle by assuming that the rotational velocity at the proximal end of the imaging conduit is a suitable approximation of the rotational velocity at the distal end of the imaging conduit. As imaging conduits become smaller to access smaller vessels and be incorporated into guidewires, they also become more easily deformed, and the problem of non-uniform rotational distortion worsens.

Also, many of the intravascular imaging systems use a constant rotational speed for a long enough period of time that the system assumes a steady state where the average rotational speed at the distal end of the imaging conduit sufficiently approximates the average rotational speed at the proximal end of the imaging conduit. In the case of the present invention, many of the embodiments involve changing the rotational speed frequently or continuously, and the assumption of a steady state being achieved between the rotational speed at the proximal and distal ends of the imaging conduit may not be a reliable one. For this purpose, a rotary encoder near the distal end of the imaging conduit or incorporated into the imaging assembly may be of benefit. Optical, resistive or other rotary encoders would be of use here.

An optical pattern on a non-rotary component in the vicinity of a rotary component could be viewed by an optical receiver on the rotary component. The optical pattern may be as simple as a line pattern that extends around circumference of the non-rotary component and each time a line is passed over, the optical receiver generates an optical or electrical signal to indicate that the line has been passed. The spacing between the lines would represent a known degree of rotation. Alternatively, two receivers can be used to enable quadrature encoding, which would provide direction information in addition to information regarding increments in rotational displacement.

Alternatively, the encoder can encode a position by using multiple receivers and an optical pattern such as a Gray code, commonly used on larger scale rotary encoders. Alternatively, the spectrum of wavelengths of light absorbed, reflected or otherwise emitted from the optical pattern can represent an absolute position. Thin films, diffraction gratings and other optical surfaces or components can be used for this purpose. Alternatively, the optical pattern can be on the rotary component and the optical receiver can be on the non-rotary component.

Other implementations of rotary encoders might include, a resistive rotary encoder, one or more accelerometers near the distal end of the imaging conduit, identification of fiduciary landmarks or features within the catheter. For example, the thickness of the imaging shell may vary as a function of angle around the longitudinal axis.

FIG. 14 shows an embodiment of the imaging probe at 150 containing an encoding pattern 156 contained within sheath 152 located just behind the imaging assembly 160 for encoding the rotational position of the imaging assembly 160. Near or within the imaging assembly 160 is placed a non-rotating encoding pattern 156 that is free to travel along a portion of the length of the imaging probe. Hence, while the imaging conduit 34 and the imaging assembly 160 may rotate, the optical encoding pattern 156 does not rotate. In this example, the encoding pattern has a protruding feature 158 that is received by a similarly shaped channel along the length of the external sheath. The one or more protruding features prevent the optical encoder from rotating while the adjacent imaging assembly 160 and imaging conduit 34 rotate.

A signal line within a rotating portion of the imaging probe is directed towards the encoder to facilitate reading the rotary position. In this example, a non-imaging fiber optic 164 is included to illuminate light onto the optical encoder element 156. The illuminating light interacts with the optical encoder in a manner that depends on the rotary angle. Light then travels from the optical encoder element 156 back through the non-imaging fiber optic 164. The proximal end of the fiber 164 may be connected to a photodetector or other optical transducer in the proximal end of the imaging probe and convert the light signal into one or more electrical signals that can then be communicated to the imaging system through the adapter. An advantage of this configuration is that the imaging assembly can be translated within the external sheath without affecting the ability to detect rotational position.

Further details and embodiments of the encoding pattern 156 and other embodiments for encoding on an imaging probe are disclosed in co-pending U.S. patent application Ser. No. 12/010,207, which is U.S. Patent Publication No. 20080177139, entitled MEDICAL IMAGING PROBE WITH ROTARY ENCODER, filed concurrently herewith, which is incorporated herein by reference in its entirety."

The performance of a deformable or tiltable component to achieve a desired imaging angle may be improved by mechanically coupling the deformable or tiltable component to another deformable or tiltable component.

Figure 15:
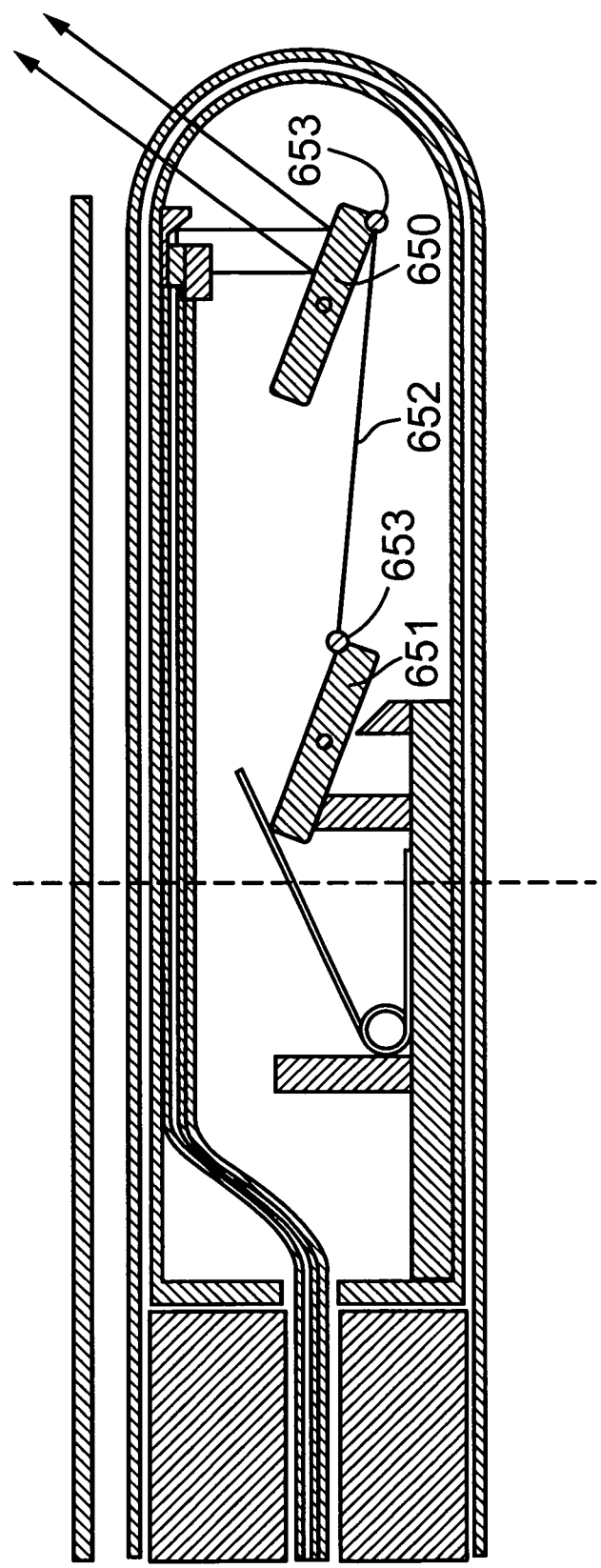
FIG. 15 is an example of an imaging probe where a tiltable component's tilt is effected in part by being mechanically coupled with another tiltable component.

FIG. 15 demonstrates an example of a distal tiltable component 650 that comprises an energy deflecting component. The distal energy deflecting component is mechanically coupled to a more proximal second tiltable component 651 via a connector 652 with a connection point 653 at each end where the connector couples to each of the two tiltable components. The second tiltable component may have better properties for achieving the desired imaging angle than can be designed into the first tiltable component such as being made of a more dense material. Alternatively, the second tiltable component may provide an advantage by providing a component to which a strain gauge or other component for measuring the imaging angle.

Alternatively, a plurality of tiltable components can be used to help achieve the desired effect of tilting or deflecting one or more energy deflecting components. For example, while the centripetal forces experienced by a single tiltable or deflectable component may be adequate to overcome a restoring force, it may be helpful to use several tiltable or deflectable components to overcome a restoring force. The several tiltable or deflectable components would mechanically interact with each, such as by direct mechanical coupling, by direct contact with or by intermittent contact with each other.

Figure 16A:
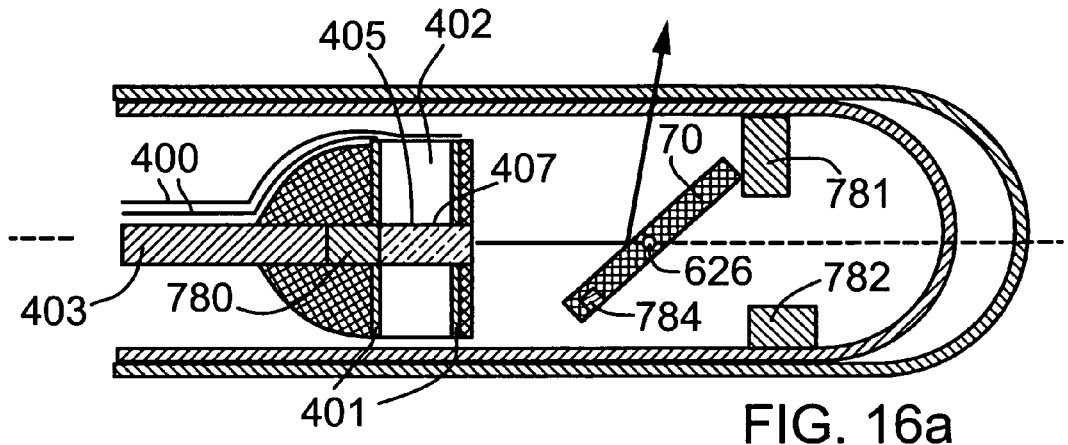
FIGS. 16a to 16c are examples of imaging probes where the ultrasound transducer or optical imaging emitter is configured for primarily side viewing imaging where the scanning mechanism allows variation in the imaging angle.

Referring to FIG. 16a, in order to allow imaging of by ultrasound and optical means in the same direction, an acoustic transducer that allows light energy to travel through a conduit in the transducer is provided. Essentially, a piezoelectric material is altered to have an opening, such as a hole, made through its substrate. Electrical contacts 400 are directed to the conducting layers 401 on either side of the transducer's acoustic substrate 402. A fiber optic 403 provides an optical conduit for enabling optical imaging. An optional optical spacer 780 and GRIN lens 405 or other optical component can reside in the opening 407 of the acoustic substrate 402, as seen in FIG. 16a. Optical imaging energy from the fiber is directed towards a tiltable component 70 which is tiltable around a pivot axis 626. The tiltable component comprises a reflective surface. Conductive layers 401 on either side of the piezoelectric material are incorporated as required for applying a voltage to the piezoelectric.

A stop 781 is shown as well as a magnet 782 as part of the imaging assembly. There is also a second magnet 784 on the tiltable component 70. The magnets act as one of several possible sources of a restoring force that tends to bring the tiltable component into contact with stop 781. At higher rotational speeds, the tiltable component 70 will tilt away from the stop 781 around its pivot axis 626 resulting in a change in the imaging angle. Thus, FIG. 16a depicts an embodiment of imaging probe 10 suitable with a scanning mechanism that enables side viewing at multiple imaging angles.

Figure 16B:
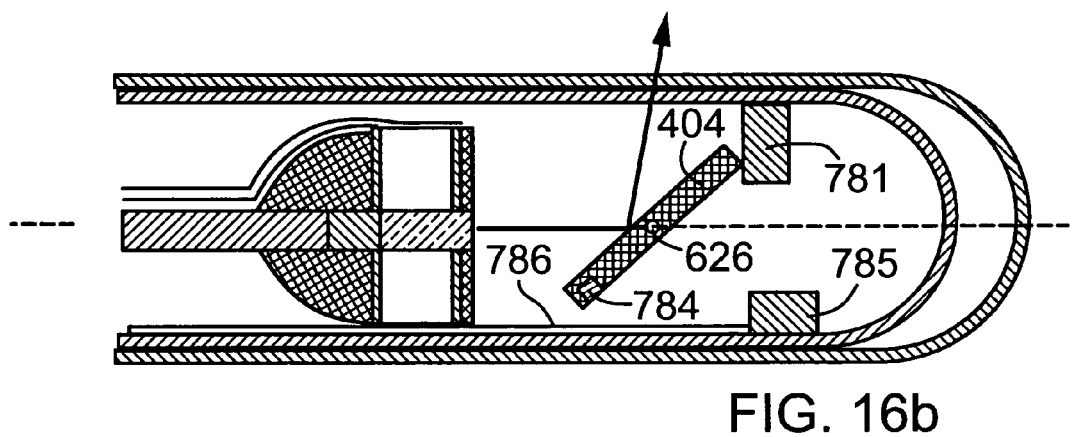

FIG. 16b depicts a similar embodiment except that the magnet 782 is an electromagnet 785, with an electrically conductive circuit 786 extending from the proximal end of the imaging probe to the electromagnet 785 to provide the electromagnet with electrical current. By varying the strength and direction of the magnetic field produced by electromagnet 785 it is possible to adjust the restoring force of the tiltable component 70 as may be desired during use. The tilting mechanism in this particular embodiment is not dependent on centripetal acceleration. Therefore, a scanning pattern can also be generated independent of rotational motion by using an to electromagnet and a tiltable component that is affected by the electromagnet, such as by having a second magnet on the tiltable component. The use of magnetic forces can be applied to the embodiments for forward-viewing imaging (as seen in FIGS. 5a to 5i) and for embodiments that use a deformable component (as in FIGS. 10a and 10b) to change an imaging angle. Similarly, if the tiltable component or deformable component does not include a magnet, a force to torque the tiltable or deformable component in a first direction can be provided by other means, such as a spring, cantilever and other means described for restoring forces above.

An electrically controllable electromagnetic force can then be used to torque the tiltable or deformable component in the opposite direction.

Figure 16C:
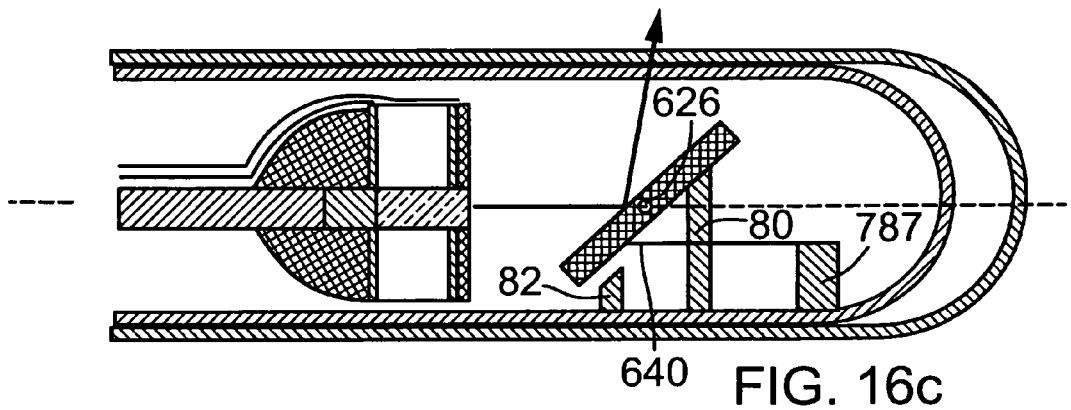

An alternative embodiment for sideviewing that uses a non-magnetic restoring force, in combination with centripetal forces for enabling side-viewing imaging is shown in FIG. 16c. Stops 80 and 82 limit the range of motion of the tiltable component 70. A cantilever wire 640 is mounted on a post 787 and comes into contact with a surface of the tiltable component 70.

At higher rotational speeds, the tiltable component will pivot (counterclockwise in FIG. 16c) and cause a change in the imaging angle.

As shown in some of the embodiments of the present invention, the combination of ultrasound and one or more optical imaging means for use with the scanning mechanisms of the present invention may be desired. FIGS. 16a to 16c depict examples of how an ultrasound transducer can be combined with an optical imaging emitter and/or receiver.

FIGS. 17a to 17g also depict various embodiments for combining an ultrasound transducer with an optical imaging emitter and/or receiver. These embodiments incorporate a deflecting mechanism for the optical imaging emitter and/or receiver, such as a mirror or prism.

Figure 17A:
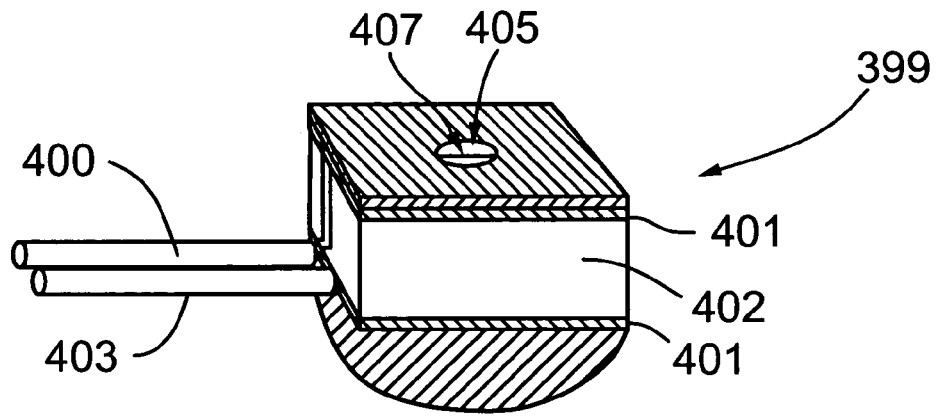

Referring to FIG. 17a, an imaging sub-assembly 399 is provided which is configured to allow imaging by acoustic and optical means in the same direction, so that an acoustic transducer that allows light energy to travel through a conduit in the transducer is utilized. Essentially, probe 399 uses an acoustic transducer 402 which is altered to have an optically transmissive channel made through its substrate. The acoustic transducer 402 can be any kind of ultrasound transducer known in the art, such as piezoelectric composition (e.g. PZT or PVDF), a composite transducer or a single crystal transducer.

Electrical contacts 400 are directed to the conducting layers 401 on either side of the transducer's acoustic substrate 402. A fiber optic 403 provides an optical conduit for enabling optical imaging. One or more matching layers can be added to the emission surfaces of the transducer, such as an epoxy layer (such as a silver or copper conductive epoxy layer which may functionally also serve as one or both of the electrodes that drives the transducer), or a polymer (such as parylene or PVDF).

The optically transmissive channel 407 is made by any of several techniques, such as precision drilling, laser ablation, photo-etching, inclusion of a feature in a mold to create the opening and others.

Conductive layers 401 on either side of the piezoelectric material 402 are incorporated as required for applying a voltage to the piezoelectric. The opening 407 is coupled to an optical waveguide 403, either directly, or by means of one or more mirrors 404 or prisms and one or more lenses 405.

Figure 17B:
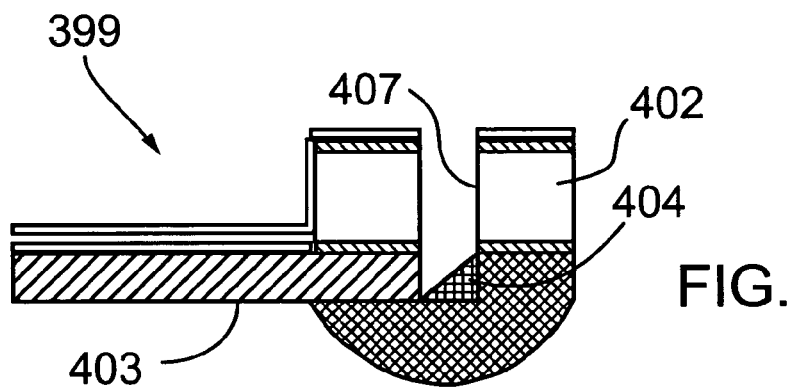

As in FIG. 17b, the light from the fiber can be directed towards a mirror (or prism) 404 that causes the light from the fiber to be deflected through the optically transmissive channel 407. Alternatively, as in FIG. 17c, a prism 397 can be used to deflect the light through the optically transmissive channel. The prism 397 may deflect light either as a result of total internal reflection or be assisted by a reflective coating on its deflecting surface. The prism 397 may be a separate optical component that is affixed to the appropriate position along the optical path. For example, it can be glued in place onto the end of a fiber, onto a lens or onto a spacer using bonding methods such as UV cured glue. Alternatively, attaching a no-clad optical fiber along the optical path and cutting the segment of no-clad fiber at a desired length can be performed to make the prism. The segment of clad fiber can be cut and/or polished to achieve the desired angle. Mao describes this method in the previously cited reference.

Figure 17C:
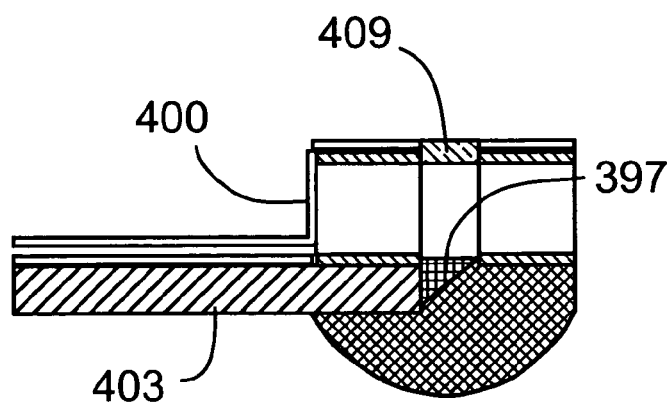
Figure 17E:
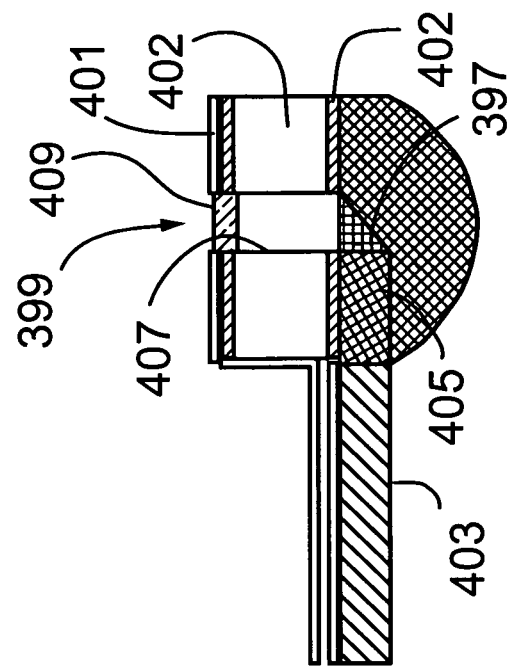

Also seen in FIG. 17c, an optically transparent window 409 may optionally be found at the end of the optically transmissive channel 407 and any unoccupied space within the channel may be filled with a gas, fluid or optically transparent material such as glass or any of several transparent polymers known in the art. The purpose of the window 409 is to prevent undesired air bubbles from being created or retained in the channel 407 and to protect the components in the optically transmissive channel 407.

Figure 17D:
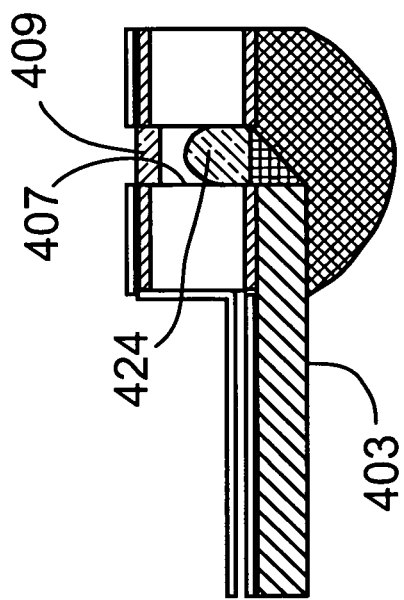

As seen in FIG. 17d it may be desirable to have a gas instead of fluid or solid material inside the channel 407 to improve the refractive power of certain optical components such as a curved lens 424, which may be a ball lens.

As seen in FIGS. 4e to 4g, the GRIN lens 405 or other optical component can reside adjacent to the distal dip of the optical fiber 403, between the fiber 403 and the deflecting mirror or prism 404 along the optical path. In this case, the opening in the acoustic substrate 402 can be left free of any optical components and simply contain an optically transparent material, or be covered by a window 409.

Referring to FIG. 17f an optical spacer 433 is located between the distal end of the optical fiber 403 and GRIN lens 405. The optical spacer element 433 may comprise an optically transparent medium, such as no-clad fiber, glass, plastic, a gas-filled gap or a fluid-filled gap. The use of an optical spacer element 433 may help reduce the required precision for the alignment and sizes of optical components in order to achieve a desired focal length.

Alternatively, as seen in FIG. 17g, the path length of the prism or mirror 404 can act as all or a portion of the optical spacer in between the distal end of the optical fiber and the lens. The advantage of using the distance that light must travel through the mirror or prism 404 as a substitute for a portion of a functional optical spacer is that the focusing element (e.g. the GRIN lens 405 or other lens) is closer to the region being imaged, thus improving the effective working distance of the optical imaging system. In some situations, the lens 405 can be offset from either edge of the optically transmissive channel to achieve the desired depth of focus, as in FIG. 17h.

Further details of various combined IVUS/OCT devices which may used with the scanning mechanisms disclosed herein are disclosed in copending application Ser. No. 12/010,208, which is U.S. Patent Publication No. 20080177183, entitled IMAGING PROBE WITH COMBINED ULTRASOUND AND OPTICAL MEANS OF IMAGING filed concurrently herewith, which is incorporated herein by reference in its entirety.

FIGS. 18a through 18d depict a tiltable deflecting component that has an optically reflective surface that is distinct from the acoustically reflective surface. FIG. 18a is a perspective drawing of a deflector that has holes on its side for receiving pins on which the deflector can pivot within an imaging assembly. FIG. 18b shows a cross-section through the deflector near the center of the deflector. The holes for receiving pins 465 are seen. The top layer is a flat, optically reflective layer 461. Under the optically reflective layer is a generally acoustic transparent layer 462, which lies between the optically reflective layer and an acoustically reflective substrate 463. Such a device can be constructed by taking a disc of an acoustically reflective material such as stainless steel and drilling the necessary holes or indentations so that the deflector can eventually be mounted into an imaging assembly. A parabolic or spheroid indentation can be made into one face of the disc. The indented surface can then be filled with an acoustically transparent medium, such as TPX. An optically reflective film, such as a thin layer of gold, can then be added onto the top surface of the acoustically transparent medium. FIGS. 18c and 18d show cross-sectional images of such a deflector at different points away from the center of the disc.

Figure 19A:
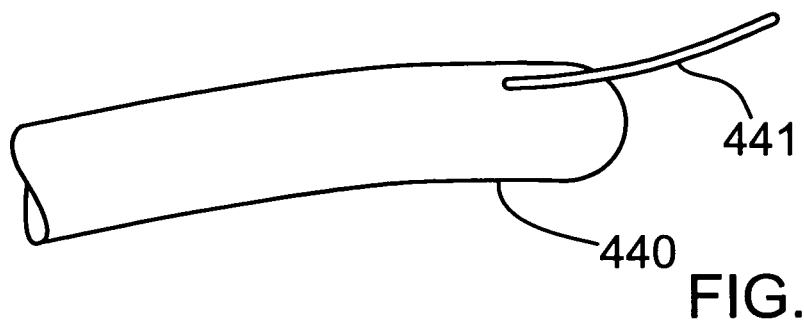
FIGS. 19a and 19b depict an example of using of a flexible imaging probe or imaging catheter with a steerable guidewire to deflect the distal region of the forward looking catheter.
Figure 19B:
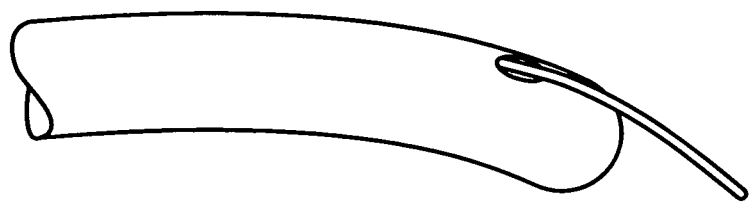

FIGS. 19a through 19h demonstrate the use of the imaging probe of the present invention in conduction with one or more steerable components. Steerable guidewires, such as the STEER-IT guidewire from CORDIS are available, where the distal portion of the wire can be controllably deflected by the operator. Similarly, steerable catheters, such as those using a mechanism described by Badger (U.S. Pat. No. 4,898,577), are available where the operator can controllably deflect the distal tip of the catheter. FIG. 19a demonstrates the distal portion of a flexible embodiment of the imaging probe 440 with a guidewire lumen wherein a steerable guidewire 441 resides substantially within guidewire lumen of the external sheath of the imaging probe. FIG. 19b demonstrates how a deflection of the steerable guidewire results in a deflection of the distal region of the imaging probe.

Figure 19C:
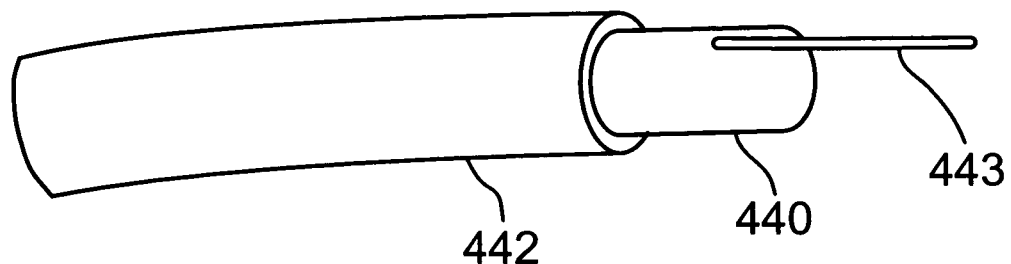
FIGS. 19c and 19d demonstrate an example of an imaging probe where a steerable guiding catheter is used to deflect the distal region of the imaging probe.
Figure 19D:
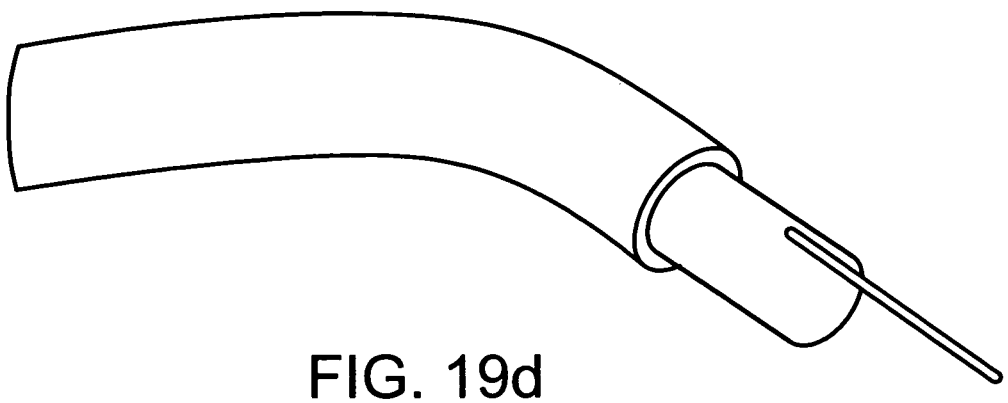

FIG. 19c demonstrates the distal portion of an imaging probe 440 which substantially resides within a steerable catheter 442. A guidewire 443 may also extend through the imaging probe. The guidewire may also be steerable or may be a conventional, non-steerable guidewire. FIG. 19d demonstrates how a deflection of the steerable catheter results in a deflection of the distal region of the imaging probe.

Alternatively, the same mechanisms that allow for steering in steerable guidewires or steerable catheters can be incorporated directly into the imaging probe.

Figure 19E:
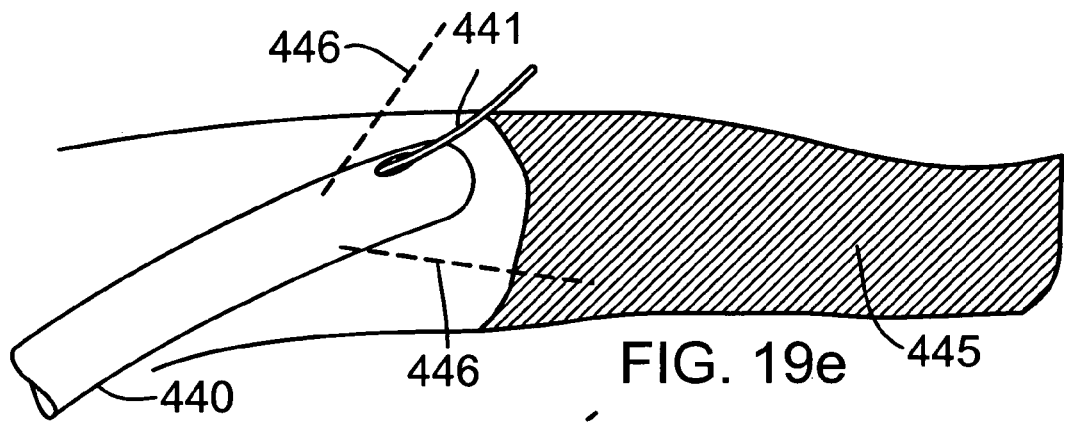
FIGS. 19e through 19h demonstrate an example of an imaging probe used in conjunction with a steerable guidewire that incorporates an inflatable balloon over the distal region of the guidewire so that a path can be made that is large enough for the imaging probe to travel through an occlusion.
Figure 19F:
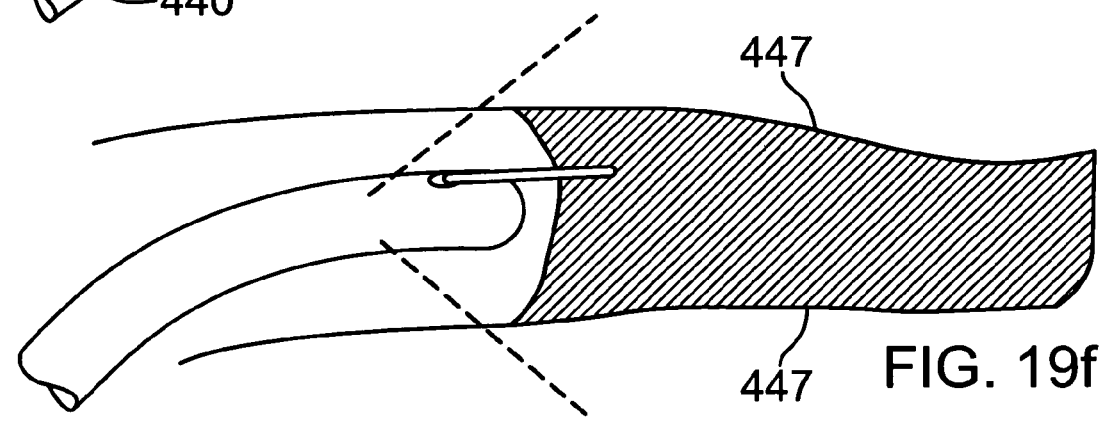

FIGS. 19e through 19h more specifically demonstrate how a steerable component can be used in conjunction with the imaging probe to facilitate crossing an occluded lumen of a vessel. In FIG. 19e, a steerable guidewire 441 resides substantially within the imaging probe 440. When the imaging probe is advanced adjacent to the occluded segment of the vessel 445, the imaging means has a field of view defined by the extremes of the range of imaging angles 446 achievable by the imaging probe. The steerable guidewire can be controlled to deflect the imaging probe and guidewire in a desired orientation, as seen in FIG. 19f. The guidewire can then be advanced under image guidance into the occluded segment. If desired, image guidance of the advancement of the wire can help ensure that the wire remains within the vessel wall boundaries 447 while being advanced. The guidewire may have properties such as a hydrophilic coating, or sufficient stiffness to facilitate initial penetration of the occluded segment. The imaging probe 440 can then be advanced into the occluded segment 445 over the wire 441. An iterative process of imaging, steering the wire, advancing the wire and/or advancing the imaging probe can be used to facilitate penetration through an occluded segment.

Figure 19G:
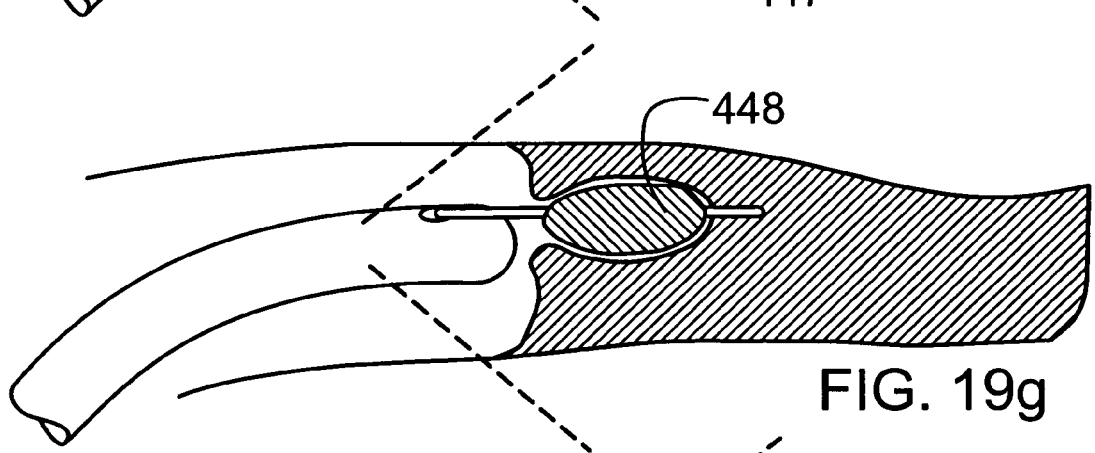
Figure 19H:
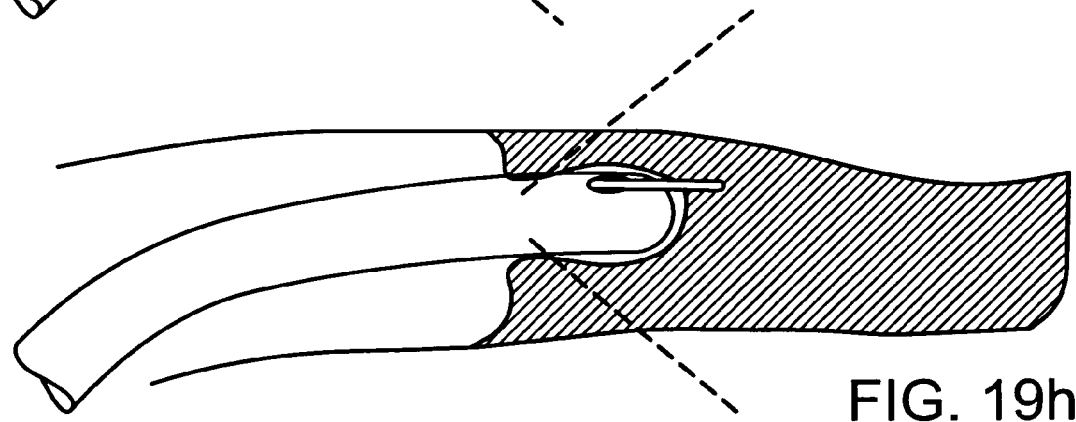

Optionally, as seen in FIG. 19g, the guidewire may comprise an expandable component, such as an inflatable balloon 448 and an inflation lumen (not seen), to facilitate the creation of a region in the occlusion into which the bulkier imaging probe can be more easily advanced. An iterative process of imaging, steering the wire, advancing the wire and/or advancing the imaging probe can be used to facilitate penetration through an occluded segment. FIG. 19h demonstrates the imaging probe having been advanced into the occluded segment from which point another iteration can be started.

Optionally, a component that resembles the tip of a guidewire can be mechanically coupled to the distal end of the imaging probe to form an integrated guidewire tip (not shown). The integrated guidewire tip may be bendable, and have the property of shape memory. The tip may be an additional feature of the imaging probe to minimize the likelihood of trauma to the anatomic region in which the probe is advanced. The tip may alternatively serve the purpose of providing a manner for directing the distal end of the probe in a preferred direction within the anatomic regions of use.

Figure 20A:
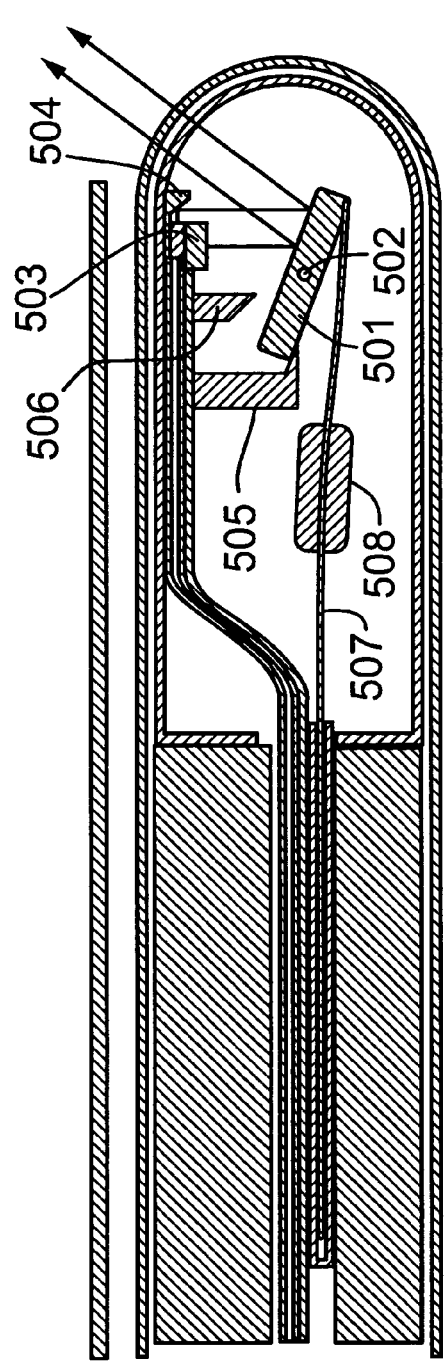
FIGS. 20a and 20b demonstrate how a weighted elastic member can be attached to a tiltable component to help cause a deflection of the tiltable component.
Figure 20B:
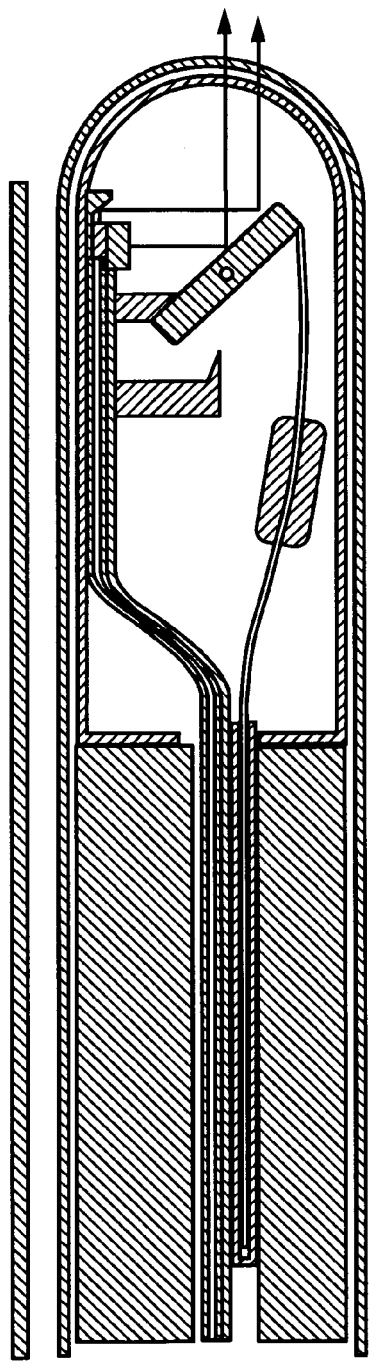

FIG. 20a depicts another embodiment for causing a tiltable component to be able to effect a change in imaging angle as a function of the rotational speed of the imaging assembly. A tiltable deflecting component 501 is mounted on pin 502. An acoustic transducer 503 and optical emitter/receiver 504 are included, as is a first stop 505 for the maximum imaging angle and a second stop 506 for the minimum imaging angle. A weighted elastic component is attached to the tiltable component and attaches to either the imaging assembly or imaging conduit. The weighted elastic component may comprise a nitinol rod 507 with a stainless steel weight 508 attached to it or be made of other suitable materials. At low rotational speeds, the elastic component assumes a relatively linear profile as seen in FIG. 20a. As the rotational speed is increased, the centripetal acceleration of the weighted elastic component will cause weight to move towards the wall of the imaging assembly. Subsequently, the elastic component will deform and cause the deflecting component to changes its tilt angle as seen in FIG. 20b. This configuration may augment the ability of the present invention to reliably achieve a desired imaging angle.

The imaging probe may include a motion detector for detecting movement of the movable member (tiltable or bendable members) relative to a remainder of the imaging assembly. The motion detector may be based on any of optical coherence based detection means, reflection intensity detection means, and a strain gauge based detection means. The pivotally mountable members may be pivotally mounted on a low friction pivot mechanism. The restoring mechanism is provided by any one or combination of a spring and a magnetic/electromagnetic assembly as discussed above. The restoring mechanism may also include a surface exhibiting electrostatic properties which interact with the movable member. It will be understood that the hollow shaft may be an external catheter sheath which may have memory properties.

The imaging probe disclosed herein may be fitted to existing control and image processing system and display systems to which the probe is connectable. The processing and display system would be configured to process the received energy signals and produce images of interior surfaces or adjacent structures of said bodily lumens and cavities or exterior surfaces or adjacent structures of a body.

Image Reconstruction

While several embodiments have been described above for varying the imaging angle, it will be helpful to either presume, estimate, measure (either directly or indirectly) or otherwise derive the imaging angle and rotational angle associated with the imaging data acquired. Each pixel or sample of imaging data can be associated with both 1) an angle around the rotational axis referred to as the rotation angle, 2) an angle from the rotational axis referred to as the imaging angle and optionally 3) a distance from a reference point within or near to the imaging assembly, such as from the imaging receiver or from the energy deflecting component. These two angles and the optional distance measurement can be used to help reconstruct the 3D geometry of the imaged objects/tissue.

In ultrasound the distance from the transducer or deflecting component is estimated based on the time of flight of the ultrasound signals in combination with the speed of sound. In optical coherence tomography, distance from the receiving end of the optical circuit or from the deflecting surface is measured using either interferometry or a technique referred to optical frequency domain imaging (OFDI). For optical coherence tomography, a range of depths to be imaged, or a "window" is usually selected to optimize the performance of the system. The window size can be as small as 4 microns to as large as several millimeters and is selected based on the performance requirements of the system, such as the number of pixels or vectors to be acquired per time interval and the optical properties of the is media (such as blood, tissue, air and/or clear liquid) through which the imaging occurs. For angioscopy and for infra-red imaging as described by Amundson, there is no distance information, although the enabling of stereo vision by using two sets of optical emitters and/or receivers in the present invention would facilitate some depth perception.

In the simplest embodiments, the imaging angle or rotational angle may not be of interest and the ability to vary the imaging angle without actually knowing the imaging angle would be a sufficient improvement over the prior art.

However, in many cases the imaging angle is of interest for generating adequate 2D or 3D representations of the imaged region and/or for making measurements within the imaged region. Several methods can be used to derive the imaging angle. In the simplest case, the imaging angle may be a function of the rotational velocity. Therefore, an estimate or measurement of the rotational velocity of the imaging assembly can be mapped to an estimate of the imaging angle based on a function or look-up table that is derived from experiments or first principles. In many cases the rotational velocity will be a time-varying function and the mechanism for mapping the rotational velocity to an imaging angle may not simply use the instantaneous rotational velocity as an input to the mapping scheme, but may also incorporate rotational velocities that have occurred or are planned to occur near that instant. This process of simply mapping the rotational velocity to an imaging angle is most appropriate when the tiltable component or bendable component is not markedly susceptible to external forces to the imaging assembly. For example, unless the rotational axis of the tiltable component goes through the approximate center of mass of the tiltable component, the effect of gravity on the tiltable component may affect the actual imaging angle sufficiently to distort the resulting image or any measurements made based on an assumption of the imaging angle.

The degree of the tilt angle over a period of time may be adequately assumed to approximate a pre-selected parametric or arbitrary function which can be used as an input to the image reconstruction process. The pre-selected imaging angle function may be dependent on the probe type and the rotational motion control sequence that is applied to the motor controller. The user may be able to adjust the imaging function and thus adjust the reconstructed images by altering one or more parameters of a parametric function or by adjusting arbitrary points of the arbitrary function.

More direct assessments of the imaging angle are possible. A strain gauge can be added to assess the deformation or rotation of either a bendable or tiltable component. Alternatively, an optical tilt encoding interface can be incorporated into to the tiltable or bendable component and monitored through a separate fiber optic channel or using local LEDs and photodetectors. For example, a fiber optic may direct light towards a surface of the tiltable or bendable component and the intensity of light back-reflected into the fiber may vary as a function of the tilt angle. This intensity can then be detected using a photodetector at the proximal end of the encoder's fiber optic.

Resistive, capacitive, magnetic and inductive encoders can also be used. Alternatively, information acquired by the imaging energy may be used to provide an assessment of the imaging angle. For example, in the case where the imaging assembly comprises an energy deflecting surface for either ultrasound or optical coherence tomography, most of the imaging energy will be reflected in the direction of the imaging angle. However, there will be a small amount of imaging energy that is reflected towards the imaging energy receiver. This amount of backreflected imaging energy can be increased by making small changes in the smoothness or texture of the reflecting surface to make it an imperfect optical reflector.

Using the conventional techniques for measuring distance that are used in ultrasound or OCT imaging, it is possible to identify changes in the distance from between the receiver and the deflecting component. Therefore, if the region of the deflecting surface on which the imaging energy is deflected changes its distance from the imaging receiver as a result of a tilt or bend, this distance can be used to determine the imaging angle using trigonometric principles.

Furthermore, a separate OCT fiber, with the necessary distal optical components (such as a lens and/or spacer) may be included for the dedicated purpose of assessing tilt angle. The OCT fiber may be used to track the motion of any suitable surface of the tiltable or deflectable member. Alternatively, a separate high frequency ultrasound transducer (such as a transducer ranging from 20 to 120 MHz in center frequency) may be used for the dedicated purpose of assessing tilt angle.

OCT imaging has much higher resolution than ultrasound imaging, so it would be preferred in many cases to use the OCT receiver to measure this change in distance as a surrogate marker of change in imaging angle. Alternatively, the shell of the imaging assembly or another feature of the imaging probe can act as an interface that produces a reflection detectable by either acoustic or optical means. Such an interface therefore provides an intrinsic landmark that can be used. Therefore, the distance of the path length between the receiver and this interface or between the deflector and the interface can be detected. If this path length changes as a function of the imaging angle (due to the morphology of the shell) then the imaging angle can be inferred.

A signal detection mechanism incorporated into the imaging system can be used to automatically detect the reflection produced by either the deflecting surface or the intrinsic landmark interface and provide information regarding the imaging angle to other components of the imaging system. Such a signal detection system could be enabled using either a hardware or software detection system or a combination of both.

A schematic for an imaging angle encoder circuit 200 for detecting the imaging angle of a tiltable or deflectable member is shown in FIG. 21a. Light is generated by a light source 222 and is coupled into a first fiber optic segment 211. The coupling can occur by positioning and orienting the proximal end of the first fiber optic segment 211 adjacent to the light source 222. The coupling of light into fiber optics is well known in the art and may optionally involve the use of a lens 220, collimator or other optical components useful for coupling light into optical fibers. The light source may be any light source known in the art, such as a laser, LED, bulb or other such component. Light propagates along the first segment 211 of the fiber optic towards an optical coupling component 212, such as a beam splitter, fiber coupler or circulator for example. Light then travels along a second fiber optic segment 213 that substantially resides along the length of the imaging probe to a position proximate to where the imaging angle is to be estimated or measured based on the tilt or deformation of the tiltable component or deformable component. The second fiber optic segment 213 may include an optional optical rotary joint 214 if the imaging probe design requires such a joint to minimize or relieve torque within the encoder circuit.

Light from the second fiber optic segment 213 may propagate through some optional optical components 215 at its distal end before propagating towards an encoder interface 204. The optional distal optical components 215 may include any of the following, including one or more lenses, collimators, mirrors, prisms or optical spacers. The light emitted from the distal optics then interacts with an imaging angle encoder 204. The possible interactions of the imaging angle encoder 204 with the emitted light are several and will vary based on the angle of deflection or tilt of the deflectable or tiltable component, as described later. As a result of the interaction between the emitted light and the imaging angle encoder 204, some light may then return back towards the second fiber optic segment 213. Optional distal optics 215 may facilitate the coupling of the returned light into the second fiber optic segment. Light coupled back into the second segment 213 of the fiber optic will return towards the proximal end of the encoder circuit 200. The returning light will travel through the optical coupling component 212, some of which will be directed towards a photodetector 218 via a third segment 216 of fiber optic. The output of the photodetector 218 will then be used to estimate or measure the imaging angle based on the degree of deflection or tilt of the deflectable or tiltable component 70 (as will be discussed with respect to FIGS. 22a to 22d below).

It should be noted that the inclusion of the optional rotary joint 214 is shown in the second fiber optic segment 213 of the embodiment in FIG. 21a, but could alternatively be included in either the first 211 or third 216 segments of fiber optic. In those embodiments where the rotary joint 214 is in the first segment 211, the photodetector 218, third segment 216 of fiber optic and the coupling mechanism 212 (splitter, optical coupler or circulator) would be rotary components of the adapter 14 and imaging probe 12. In those embodiments where the rotary joint 214 is in the third segment 216, the light source 222, first segment of fiber optic 211, proximal optics 220 and the coupling mechanism 212 would be rotary components of the adapter and imaging probe. It should be noted that in many embodiments, the optional rotary joint may be completely omitted.

FIG. 21b demonstrates a schematic for an alternative optical encoder circuit 230 whereby the light from the light source 222 towards the encoder interface 204 is carried on a separate optical fiber 217 than the light that returns from the encoder interface 204 to the photodetector 226. This modification makes it possible to avoid the need for the optical coupling mechanism 212 (e.g. beam splitter, fiber coupler or circulator) shown in FIG. 21a. The light source 222 is optically coupled to an emitting fiber 217, possibly through some optional proximal optics 220. The emitted light then travels through some optional distal emission optics 232 and interacts with the encoder interface 204. Based on the interaction of the emitted light with the encoder interface 204, some light will, during at least one or more periods during operation of the probe, return towards the detection fiber 221 via some optional distal detection optics 231.

Light coupled into the detection fiber 221 will then be transmitted to a photodetector 226 for further analysis. In the case of the embodiment of FIG. 21b, the optional distal emitting optics 232 or the optional distal detection optics 231 may comprise one or more lenses, collimators, spacers, mirrors or prisms.

Figure 22A:
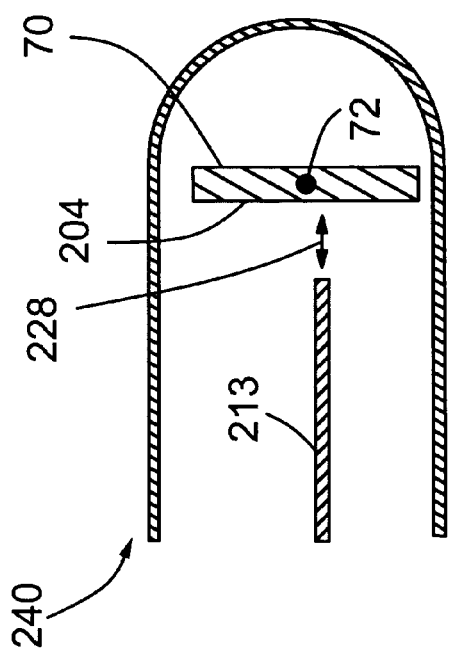

FIG. 22a shows an embodiment of a probe 240 with a tiltable component 70 configured to use the imaging angle encoder circuit 200 of FIG. 21a. Tiltable component 70 can tilt around tilt axis 604 within the external sheath 48 of probe 240. Light 228 is emitted from the distal end of fiber optic 213 of the imaging angle encoder circuit and directed towards an encoder interface 204. Light 228 then returns into the distal end of fiber optic 213. The encoder interface 204 may comprise a surface of the tiltable component 70. The surface may be polished, pigmented, marked, grated or textured in order to augment changes in the amount of light that returns to the fiber optic 213 during changes in the imaging angle created by changes in the tilt angle of tiltable component 70. Alternatively, the encoder interface may comprise a variable thickness thin film or other optical interface.

Figure 22B:
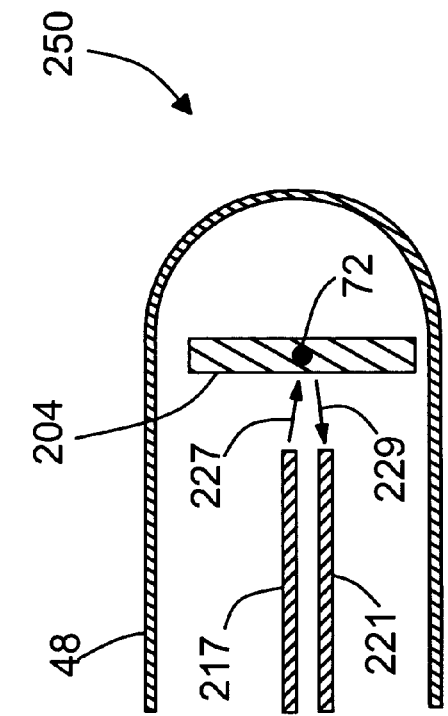
FIG. 22b shows an embodiment of an imaging probe configured to use the imaging angle encoder circuit of FIG. 21b.

FIG. 22b shows an embodiment of a probe 250 with a tiltable component 70 configured to use the imaging angle encoder circuit 230 of FIG. 21b. Tiltable component 70 can tilt around tilt axis 72 within the external sheath 48 of probe 250. Emitted light 227 is emitted from the distal end of emitting fiber optic 217 of the imaging angle encoder circuit and directed towards an encoder interface 204. Received light 229 then returns into the distal end of the detection fiber optic 221. The encoder interface 204 may comprise a surface of the tiltable component 70. The surface may be polished, pigmented, marked, grated or textured in order to augment changes in the amount of light that returns to the fiber optic 213 during changes in the imaging angle created by changes in the tilt angle of tiltable component 70. Alternatively, the encoder interface may comprise a variable thickness thin film or other optical interface.

Figure 22C:
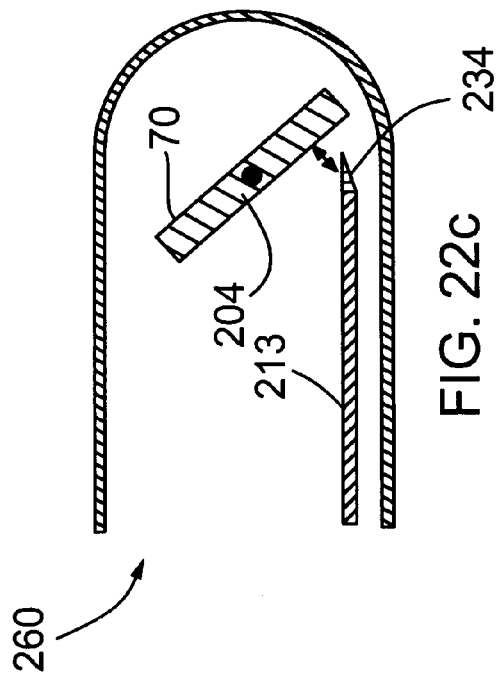

FIG. 22c shows an alternative embodiment 260 of the probe seen in FIG. 22a wherein a light deflection element, such as a mirror or prism 234, is incorporated as one of the optional distal optics components 215 of the imaging angle encoder circuit (see FIG. 21a). If a prism is used as the light deflection element, one or more of the surfaces of the prism may be coated with a reflective coating. The use of a light deflection element, such as prism 234, can allow the light used for detection of the imaging angle to approach the encoder interface 204 with a preferred general angle of incidence to allow for improved performance of the imaging angle encoder.

Figure 22D:
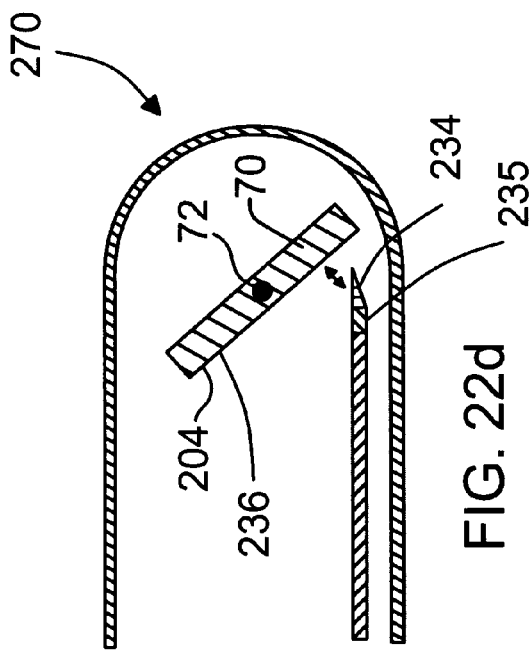
FIG. 22d shows an alternative embodiment of the probe shown in FIG. 22c which uses a lens.

FIG. 22d shows an alternative embodiment 270 of the probe seen in FIG. 22c, wherein a lens 235 is included as one of the optional distal optics components 215 of the imaging angle encoder circuit (see FIG. 21a). The use of a lens can be used to change the sensitivity of the imaging angle encoder circuit. For example, if the encoder interface 204 in imaging probe 270 comprises a reflective surface 236 on tiltable component 70, then the amount of light detected that is back-reflected from the reflective surface 236 would be dependent on both the imaging angle and how strongly focused the light emitted from fiber optic 213 is. FIG. 22e shows an exemplary plot of the intensity of light that would be detected as a function of angle of deflection without the use of a lens 235. FIG. 22f shows a comparison plot of how the intensity of light detected would be more sensitive to slight changes in the angle of deflection or tilt as a result of adding a focusing element to the distal end of fiber optic 213.

Alternatively, rather than using fiber optics to channel the light for the imaging angle encoder, either the distal end of the emitting fiber or the distal end of the receiving fiber optics could be replaced by a light source 293 or a photodetector 294 sized with adequate miniaturization to fit within the distal end the imaging probe. Such an alternative embodiment 280 is shown in FIG. 22g. The emitting and receiving fiber optics are replaced by electrical wiring 291 and 292 to connect the light source 293 and photodetector 294 to a power sources and measurement instrumentation such as an analog to digital converter. FIG. 22h shows an embodiment of the imaging probe 290 where a prism 295 is further employed to deflect light from the light source 293.

FIG. 23a shows an alternative embodiment of imaging probe 520 wherein the encoder interface comprises a generally arc-shaped encoder 524 that extends proximate to the distal end of a fiber optic 213 in the imaging angle encoding circuit. An optional lens 235 is also included. The arc-shaped encoder 524 is relatively thin and may not have a substantial mass relative to the mass of the tiltable component 70. The arc-shaped encoder can be made using any number of techniques, including laser marking, laser drilling, photolithography and many other techniques known in the art. Preferably, the arc-shaped encoder can be made from a thin sheet of a material, such as a metal, such as nickel or gold. It can then be attached at both ends to the tiltable component to assume the general shape of an arc. Alternatively, it can be formed to have an arc-like shape and attached to the tiltable component at a single end, as shown in FIG. 23b.

An example of an embodiment of the encoder interface 524 prior to being formed into the shape of an arc is shown in FIG. 23c. The encoder interface may have a series of slots or marks 525 on its surface that enable detection of an incremental change in the angle of tilt. Alternatively, as shown in FIG. 23d there may be more than one column of slots or marks and the slots or marks in adjacent columns may be offset from each other to enable quadrature encoding, that would provide the ability to detect not only an incremental change in the tilt angle, but also the direction of the change in tilt angle. Alternatively, multiple columns and multiple fibers could be used to enable absolute position encoding, such as by using a Gray Code. Alternatively, the encoder interface 524 may have a variable width slot or marking 526 as seen in FIG. 23e, whereby the width of the slot or marking varies along the length of the encoder interface.

FIG. 24a shows an alternative embodiment 530 of imaging probe 31 seen in FIG. 5a. Imaging probe 530 includes encoder circuit fiber optic 213 within imaging conduit, with fiber optic 213 being part of encoder circuit 200 of FIG. 21a. A prism 234 is attached to distal end of the fiber optic 213 to deflect the light 228 used for imaging angle detection towards the back surface of tiltable component 70. Light 228 reflected back from the back surface of tiltable component 70 is used to assess the imaging angle via the imaging angle encoder circuit. Similarly, FIG. 24b shows an alternative embodiment of an imaging probe 540 which includes an encoder circuit where the encoder interface is an arc-shaped encoder 524 (see FIGS. 23a, 23b) that resides proximate to the distal end of encoder circuit fiber optic 213 that is terminated with a lens 235. Of note, the methods for assessing the imaging angle described above and in FIGS. 21 through 24 can be applied to many of the embodiments of imaging probes described herein, including without limitation those in FIGS. 4-6, 10-12, 14-16 and FIG. 20.

Display of 3D data on a typical 2D display screen can be performed in several ways, including serial 2D images and other methods known in the art of medical imaging. For example, the 2D images can represent arbitrary planes sliced through the 3D volume, maximal intensity projection images multiplanar reformatted images and several others. It is also possible to represent the data in polar coordinates such as using the coordinates: (rotational angle, imaging angle, distance). An arbitrary surface in the 3D space based on polar coordinates can be selected for display. For example, the data corresponding to a single imaging angle over a range of rotational angles and a range of distances can be displayed.

Figure 25A:
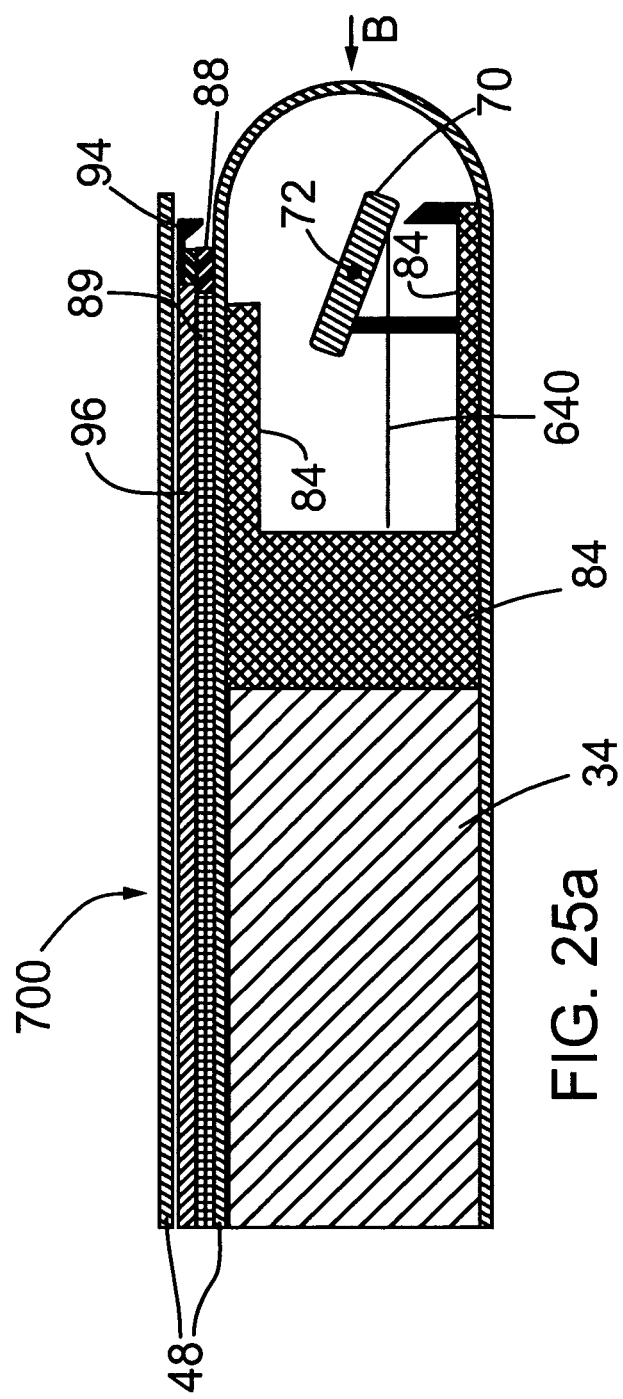
FIG. 25a is a cross sectional view of an embodiment of an imaging probe configured such that the imaging assembly rotates independent of any rotational motion which may or may not be applied to an ultrasound transducer or an optical emitter/receiver.
Figure 25C:
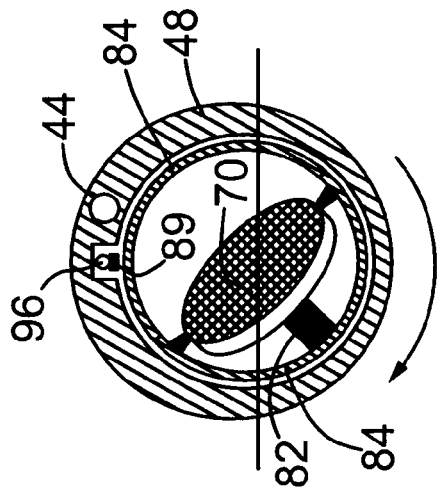
FIGS. 25b and 25c are views along arrow B of FIG. 25a but showing different relative rotational positions between the tiltable component and the ultrasound transducer.
Figure 25B:
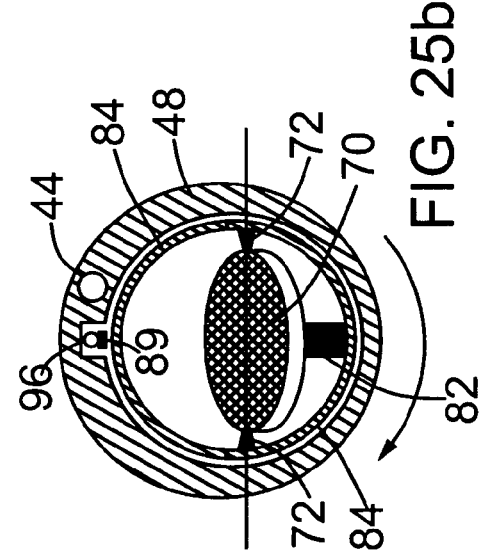

FIG. 25a shows a cross sectional view along a length of an embodiment of an imaging probe 700 where the imaging assembly rotates independent of any rotational motion which may or may not be applied to the ultrasound transducer 88 or an optical emitter/receiver 94. If ultrasound is used for imaging, ultrasound will be emitted from the ultrasound transducer 88 towards tiltable component 70 and will project ultrasound waves in a direction that is determined by the tilt angle of the tiltable component 70. The ultrasound transducer 88 and associated coaxial cable 89 in this embodiment may be embedded within or attached to external sheath 48 and is not directly attached to the shell 84, imaging conduit 34 or tiltable component 70 which acts as a deflector of the ultrasound imaging beam. Therefore, there is relative rotational motion between the tiltable component 70 and the ultrasound transducer 88, as seen in FIGS. 25b and 25c which represent different time points during a single rotation of the imaging conduit 34, shell and tiltable component 70. The direction of the ultrasound imaging beam will scan a non-planar surface that generally lies in front of the imaging probe 700.

Similarly, an optical imaging beam is emitted from fiber optic probe 96 and mirror 94 towards the tiltable component 70. As with the ultrasound transducer 88 in this embodiment the fiber 96/mirror 94 are may be embedded within or attached to external sheath 48 and are not directly attached to the shell 84, imaging conduit 34 or tiltable component 70 which acts as a deflector of the optical beam so that the imaging assembly comprised of the imaging conduit 34 and tiltable component 70 rotates independent of any rotational motion which may or may not be applied to the optical emitter/receiver 94.

Figure 25D:
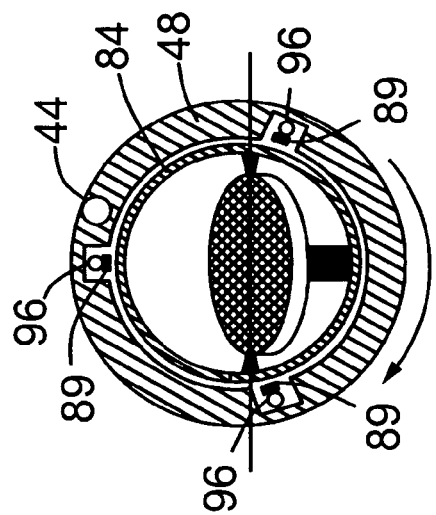
FIG. 25d is an end view of an alternative embodiment of the imaging probe of FIG. 25a having additional ultrasound transducers and/or optical imaging emitters and receivers positioned around the circumference of the imaging probe.

With a single ultrasound source 88 and/or optical source 96, the deflecting surface is not facing the source of the imaging energy beam for a substantial portion of each revolution of the rotary components. Therefore, additional ultrasound transducers 88189 and/or optical imaging emitters 96/94 and receivers can be added around the circumference of the imaging probe as seen in FIG. 25d which undergo motion independent of the imaging conduit 34 and tiltable component 70. A benefit of the present invention is that optical and/or ultrasound imaging can occur using the principle of relative rotational motion to creating a scan plane that lies generally forward of the imaging probe while simultaneous using an imaging energy deflector whereby the imaging angle is varied in part as a result of changing the rotational velocity of the rotary components (e.g. by using centripetal acceleration or hydrofoil forces in combination with a restoring force).

Of note, the principle of relative rotational motion can be applied to any of the embodiments of imaging probes described in this invention that use a tiltable or deformable surface to deflect an imaging beam, including those in FIGS. 5, 10-12, 14-16 and 20. This can be accomplished by moving any of the following components from the rotary portion of the imaging probe to a non-rotary portion of the imaging probe (such as the external sheath): the ultrasound transducer, coaxial cable for the ultrasound transducer, imaging fiber optic, prism or mirror. In addition, the concept of relative rotational motion depicted in FIGS. 25a to 25d can be applied to an ultrasound imaging probe, an optical imaging probe or a combined ultrasound and optical imaging probe. One possible advantage of using embodiments that exploit relative rotational motion is that components such as slip rings and fiber optic rotary joints can often be dispensed with by configuring the probe so that the optical or ultrasound imaging means are mounted onto a non-rotary component.

Figure 26:
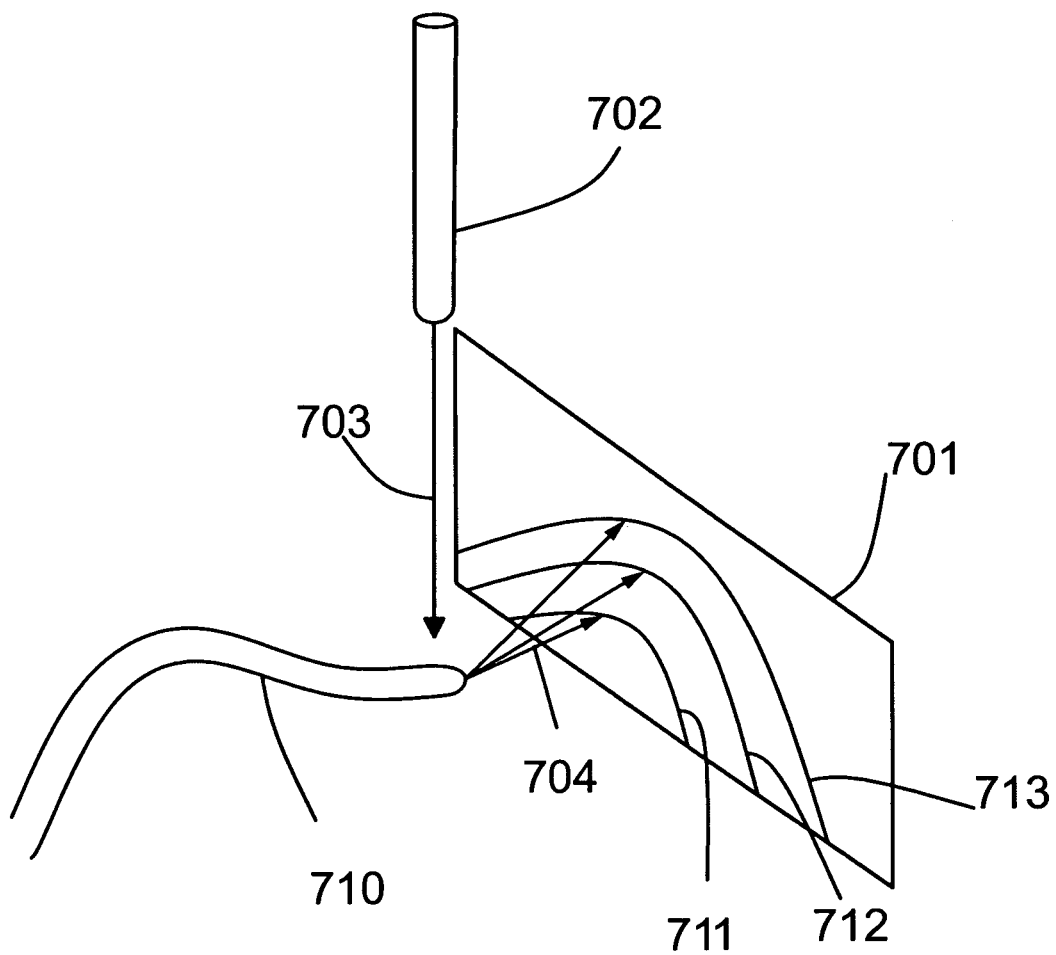

FIG. 26 shows an experimental setup used to demonstrate the functioning of the scanning mechanism described in FIG. 25a. An imaging probe 710 was placed in front of a projection screen 701. A laser light source 702 emitted a beam of light 703 onto a scanning mechanism similar to that shown in FIG. 25a. The probe 710 included the following rotary components which have been previously discussed in the various imaging probe embodiments: an imaging conduit, a shell, a tiltable component mounted on the shell via pins and a restoring force provided in the form of a cantilever wire. The rotary components were rotated via a drive mechanism (not shown) attached to the imaging conduit within the external sheath of the imaging probe. The light beam was deflected by the tiltable component in a generally forward direction. At faster speeds, the deflected light beam 704 was directed in a more forward direction than at slower speeds of rotation. The projection of the deflected light beam at a relatively fast speed is shown as curve 711 on the screen, while the projection of the light beam at a relatively slower speed is shown as curve 713, with curve 712 representing a projection of the light beam at an intermediate speed of rotation.

FIGS. 27a and 27b shows an embodiment of an imaging probe 720 which makes use of relative rotational motion, but allows the rotational position of the ultrasound transducer 88 and/or optical emitter/receiver 94/96 to be adjusted by mounting the ultrasound transducer 88 and/or optical emitter/receiver 94196 on a separate sheath 721. This additional ability to rotate the acoustic and optical imaging components independent of the external sheath 48 is helpful when the external sheath 48 is shaped to have a curved or 3D morphology, such as a curved tip as opposed to a shaft that is generally linear. Imaging probes and other catheters are often shaped near their distal end to enable the catheters to be delivered to specific anatomical regions that are best accessed or viewed by having the longitudinal axis of the catheter follow a curve or 3D path.

Furthermore, a single imaging probe may have more than one imaging transducer or optical emitter/receiver along its length and one or more scanning mechanisms along its length. For example, a probe with a scanning mechanism that enables forward looking imaging from the distal end, such as shown in FIG. 5A, could be on the same imaging probe that incorporates a separate side-viewing ultrasound transducer or optical emitter/receiver at a point remote from the distal end. Additionally, this separate ultrasound transducer or optical emitter/receiver may have a side-viewing scanning mechanism that allows a change in the imaging angle, such as that shown in FIG. 16c.

Embodiments of the present invention can be used in conjunction with or incorporated into devices that are used for intervention, such as those used for cardiovascular intervention, such as an angioplasty balloon, atherectomy device, stent delivery system, valvuloplasty system, percutaneous valve repair or replacement system, septal defect or foramen ovale closure device or localized drug delivery system. It can also be used in conjunction with or incorporated into devices that facilitate biopsies, radio-frequency ablation, resection, cautery, localized brachytherapy, cryotherapy, laser ablation or acoustic ablation. In particular, the use of the current device to enable laser or acoustic ablation of tissue can be facilitated by using the image scanning mechanism to direct higher powers of optical or acoustic energy to a targeted region. For example, while imaging a region of a blood vessel with an OCT or ultrasound embodiment of an imaging probe described in the present invention a region for the delivery of therapy can be selected through a user interface. Then, powerful pulses of energy can be delivered at times when the scanning mechanism is oriented to delivery energy in the desired direction. For example, pulses of laser energy can be transmitted down the same fiber optic used for optical imaging, be deflected by a deflecting component in those embodiments that include a deflecting component, and travel towards the targeted tissue for the desired effect. The timing of the pulses of laser energy is coordinated with the scanning pattern effected by the imaging probe to direct the energy towards the targeted region.

As mentioned previously, the combination of OCT and IVUS is helpful for the imaging probe because one of the two modalities (preferably OCT because of its higher resolution) can be used to assess the imaging angle. Also the combination of OCT and IVUS is very useful as the two modalities often provide complementary information to each other, such as in assessing vascular plaque structure and function. Images from the two modalities, when properly mapped to each other, can help to provide composite images that may provide important information regarding the tissue being assessed. In fact, any of the imaging data generated by the various acoustic and optical imaging modalities described in the present invention can potentially be combined to improve the assessment of the interrogated tissue.

Additionally, the ability to make a forward looking imaging probe that has the ability to adjust its imaging angle raises the possibility of using forward looking imaging as an alternative to fluoroscopic imaging for visualizing a vascular tree or other collections of anatomic volumes. As the probe is advanced into the body, 3D volumes of imaging data are acquired. If consecutive 3D volumes of imaging data overlap sufficiently, the possibility of assembling a series of 3D images together to form a superset of 3D imaging data becomes attractive. For example, if volume (i) is acquired and volume (i+1) is subsequently acquired, the imaging data from both volumes can undergo a series of transformations such as translations, rotations and stretches where features within the overlapping regions of the two volumes are matched to each other. This can be facilitated by use auto-correlation techniques and other well-known techniques for stitching together 2D or 3D imaging data sets.

Angioscopy and infrared imaging can also be enabled with particular advantages based on the present invention. Typically, angioscopy and infrared imaging rely on the use of bundles of fiber optics to produce an image. The volume or surface to be imaged is illuminated with light spanning a desired range of wavelengths and the back-reflected light provides an image of the interfaces that lie in the field of view. For angioscopy, the range of wavelengths substantially spans the visible spectrum, while for infra red imaging a more select range of longer wavelengths as described by Amundson is used to facilitate improved penetration through blood. For both conventional angioscopy and infrared imaging, the number of fibers within a bundle impacts the resolution of the system and the size of the field of view. However, adding more fibers to a bundle increases the size of the bundle and reduces the flexibility of the bundle.

The present invention can be used to overcome these limitations by requiring fewer fiber optics to perform the desired imaging. In the simplest case, a single fiber optic is used. The ability to scan a region with a single optical receiver by using a tiltable or bendable component provides the ability to reduce the number of fibers to scan the same region of interest. In this case, illuminating light in the desired range of wavelengths is delivered to the region to be imaged, such as through a separate fiber optic connected to a light source, an LED illuminator located near the imaging assembly, or through the same fiber that the backreflected light is received. The advantages of not requiring a fiber bundle to perform such imaging potentially include a more flexible imaging probe, a smaller imaging probe, a reduced number of photodetectors required (where photodetectors array for infrared imaging can be costly) and the ability to use a small number (such as one to ten) of highly specialized photodetectors rather than a large array (such as an array larger than 64 by 64 elements) of less specialized detectors.

Photodetectors vary with respect to their wavelength specificity and their sensitivity. Disadvantages of such a system compared to a fiber bundle system include the requirement to reconstruct the image from the scanned data, a potentially lower signal to noise ratio, and distortion of the image due to possible imperfections in the fidelity of the scanning mechanism to achieve a desired scanning pattern.

The signal to noise ratio for the single fiber optic implementation for angioscopy or infrared imaging can potentially be improved by having the illuminating light focused in a narrow beam in the direction from which imaging takes place. This is can be done by transmitting the illuminating light down the same fiber and through the same lens in the imaging assembly from which the imaging light is received. This is of particular advantage when the imaging is through a scattering medium, such as blood, as the light received by the lens and fiber optic will substantially omit light that would have been scattered from adjacent volumes if a more diffuse illuminator was used.

Gastrointestinal endoscopy, colposcopy, bronchoscopy, laparoscopy, laryngoscopy, cystoscopy, otoscopy and fundoscopy are all examples of applications to which the scanning mechanisms described in the present invention may be adapted for use in a manner similar to angioscopy or infrared imaging. Non-medical uses of a flexible and/or miniaturizable imaging probe where a scanning mechanism described in this invention is used to produce an image, such as a picture taken in the visible or infrared spectrum are several.

The imaging probe 12 and its components may be of several dimensions and properties depending on the anatomic location and purpose of use for the imaging that is enabled by the imaging probe 12. For example, for the purposes of use in the cardiovascular system, including the cardiac chambers, the imaging probe 12 would preferably be elongate and flexible, with a length ranging from 5 to 3000 mm, preferably with a length ranging from 300 mm to 1600 mm. The imaging conduit 34 and imaging assembly 30 may have a maximum cross-sectional dimension ranging from 200 microns to 10 mm, preferably ranging from 500 microns to 8 mm. The imaging conduit 34 and imaging assembly 30 may both be surrounded by an external sheath 48. This would enable the imaging conduit 34 and imaging assembly 30 to rotate within the external sheath while mechanically isolating the rotational motion of these two components from the surrounding tissues.

In some instances, embodiments of the present invention can be used wherein the imaging conduit is very short or is effectively not required. For example, the imaging assembly may be directly attached to a micromotor, a turbine or a shaft with rapid reciprocal motion. The use of the centripetal acceleration to cause a change in the imaging angle of an acoustic or optical imaging device can be incorporated in such embodiments.

In yet another example, the use of the imaging probe 12 in the gastrointestinal system would typically have the imaging probe 12 being elongate and flexible, with a length ranging from 50 mm to 6000 mm and preferably in the range of 300 mm to 2000 mm. The maximum cross-sectional dimension would typically range from 3 mm to 20 mm.

In yet another example, the use of the imaging probe 12 to image soft tissue via percutaneous means would have the imaging probe with a rigid shaft. The external sheath would be replaced by a rigid hollow shaft, such as a stainless steel tube although many other polymers, metals and even ceramics would be functionally suitable.

In yet another example, the use of the imaging probe 10 in the intraoperative neurosurgical setting would typically have the imaging probe 10 being short and semi-flexible, with a length ranging from 50 mm to 200 mm. It would be preferable that the surgeon can bend and shape the probe during the procedure to provide optimal passage from extra-cranial space towards the intracranial target being imaged. The maximum cross-sectional dimension would range from 200 microns to 5 mm and preferably from 500 microns to 3 mm.

In yet another example, the use of the imaging probe 10 in the interventional neurovascular setting would typically have the imaging probe 10 being long and ultraflexible, with a length ranging from 200 mm to 4000 mm and preferably ranging from 1300 mm to 2000 mm. The maximum cross-sectional dimension would range from 200 microns to 5 mm and preferably from 500 microns to 3 mm. The distal end of the probe would preferably possess shape memory to enhance navigation through the neurovasculature.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. An imaging probe comprising:
   an outer elongate sheath;
   a rotatable conduit extending through said outer elongate sheath, said rotatable conduit defining a longitudinal axis, wherein said rotatable conduit is connectable to a rotational drive mechanism for adjusting an angular velocity of said rotatable conduit about said longitudinal axis;
   an energy emitting device affixed to said outer elongate sheath at a location remote from a proximal end thereof for producing an energy beam;
   an imaging assembly attached to said rotatable conduit at a location remote from a proximal end thereof, said imaging assembly including a movable member for delivering the energy beam along an energy beam path from said movable member out of said outer elongate sheath at a variable imaging angle with respect to said longitudinal axis of said rotatable conduit, wherein said movable member is mounted so that the variable imaging angle between the energy beam path and said longitudinal axis of said rotatable conduit is varied by adjusting the angular velocity of said rotatable conduit; and
   a restoring mechanism configured to apply a torque to said movable member for urging said movable member away from a preferred orientation.

2. The imaging probe according to claim 1 wherein said movable member is pivotally mounted about an axis perpendicular to said longitudinal axis for pivotal movement.

3. The imaging probe according to claim 1 wherein said movable member is mounted such that it is moved by being deflected about an axis perpendicular to said longitudinal axis.

4. The imaging probe according to claim 1 wherein said energy emitting device is an ultrasound transducer, the imaging probe further including an electrical cable electrically connected at one end thereof to said ultrasound transducer and connectable at another end thereof to a power supply and ultrasound signal processing circuit.

5. The imaging probe according to claim 1 wherein the energy beam is an optical beam and wherein said energy emitting device includes a fiber optic having a distal end mounted at a location remote from a proximal end of said outer elongate sheath, said distal end of said fiber optic including an optical imaging emitter/receiver, said fiber optic extending along said outer elongate sheath and having a proximal portion suitable for optical coupling to a light source.

6. The imaging probe according to claim 1 including additional energy emitting devices positioned around a periphery of the distal end section of said outer elongate sheath for directing multiple energy beams toward said imaging assembly.

7. The imaging probe according to claim 6 wherein said energy emitting device and said additional energy emitting devices are ultrasound transducers and/or optical imaging emitters/receivers.

8. An imaging probe comprising:
   an outer elongate sheath;
   an inner elongate sheath located in said outer elongate sheath;
   a rotatable conduit extending through said inner elongate sheath, said rotatable conduit defining a longitudinal axis, wherein said rotatable conduit is rotatable about said longitudinal axis;
   an energy emitting device affixed to said inner elongate sheath at a location remote from a proximal end thereof for producing an energy beam, wherein said inner elongate sheath is rotatable about said longitudinal axis;
   an imaging assembly attached to said rotatable conduit at a location remote from a proximal end thereof, said imaging assembly including a movable member for delivering the energy beam along an energy beam path from said movable member out of said inner elongate sheath and said outer elongate sheath at a variable imaging angle with respect to said longitudinal axis of said rotatable conduit, wherein said movable member is mounted so that the variable imaging angle between the energy beam path and the longitudinal axis of said rotatable conduit is varied by adjusting the angular velocity of said rotatable conduit; and
   a restoring mechanism configured to apply a torque to said movable member for urging said movable member away from a preferred orientation.

9. The imaging probe according to claim 8 wherein said movable member is pivotally mounted about an axis perpendicular to said longitudinal axis for pivotal movement.

10. The imaging probe according to claim 8 wherein said movable member is mounted such that it is moved by being deflected about an axis perpendicular to said longitudinal axis.

11. A scanning device for directing an energy beam during rotary motion, comprising:

a rotary component having a rotary axis, wherein said rotary component is connectable to a rotary drive mechanism;

an energy emitting device coupled to said rotary component, wherein said energy emitting device is configured to produce the energy beam;

a movable member configured to direct the energy beam along an energy beam path at a variable angle with respect to said rotary axis of said rotary component, wherein said movable member is coupled to said rotary component such that the variable angle between the energy beam path and the rotary axis of said rotary component is varied by adjusting the angular velocity of said rotary component; and a restoring mechanism configured to apply a torque to said movable member for urging said movable member away from a preferred orientation.

12. The scanning device according to claim 11 where the energy is one or both of optical energy and ultrasound energy.

13. The scanning device according to claim 11 where the energy is therapeutic energy.

14. The scanning device according to claim 13 wherein the therapeutic energy includes continuous wave laser light or pulses of laser light.

15. The scanning device according to claim 11 wherein said movable member is a tiltable component pivotally mounted about an axis perpendicular to said rotary axis for pivotal movement.

16. The scanning device according to claim 11 wherein said movable member is a deflectable component mounted such that it is moved by being deflected about an axis perpendicular to said rotary axis.

17. The scanning device according to claim 11 wherein said energy beam is an acoustic ultrasound energy beam and said energy emitting device is an ultrasound transducer.

18. The scanning device according to claim 11 wherein the energy beam is an optical beam, wherein said energy emitting device includes a fiber optic.

19. The scanning device according to claim 11 wherein said energy emitting device is an imaging device configured to emit incident imaging energy and to receive reflected imaging energy.

20. The scanning device according to claim 11 wherein said energy emitting device is a therapeutic energy emitting device configured to emit therapeutic energy.

21. The scanning device according to claim 11 wherein said movable member is a first movable member, and wherein said rotary component includes a second movable member, and wherein said second movable member is mounted is such a way that said second movable member's movement is a function of the angular velocity of the rotary component, and wherein movement of said second movable member urges said first movable member to move.

22. The scanning device according to claim 13 wherein the therapeutic energy includes acoustic energy.

23. An imaging probe comprising:
a hollow shaft;
a rotatable conduit extending through said hollow shaft, said rotatable conduit defining a longitudinal axis;
a scanning mechanism attached to said rotatable conduit at a location remote from a proximal end of said rotatable conduit, said scanning mechanism including a tiltable member configured for controlling a direction of an imaging beam emitted from said scanning mechanism, wherein said tiltable member is tiltable such that a tilt angle of said tiltable member is variable relative to the longitudinal axis;

an imaging angle encoder coupled to said scanning mechanism, wherein said imaging angle encoder is configured to produce a signal dependent on the tilt angle of said tiltable member; and a signal delivery channel connected to said imaging angle encoder and extending through said hollow shaft for delivering the signal dependent on the tilt angle to a proximal end of said hollow shaft;

wherein said imaging angle encoder is an optical imaging angle encoder configured to direct an incident optical beam onto a surface associated with said tiltable member and to receive a reflected optical beam from said surface, such that a change in the tilt angle of the tiltable member produces a corresponding change in the reflected optical beam;

wherein said signal delivery channel is a fiber optic, and wherein the signal is the reflected optical beam;

wherein said imaging angle encoder includes one or more distal optical components in optical communication with a distal end of said fiber optic for directing the incident optical beam onto the surface associated with said tiltable member and for collecting the reflected optical beam from said surface; and wherein said distal optical components are selected from the group consisting of a lens, collimator, mirror, prism and optical spacer, and a combination thereof.

24. An imaging probe comprising:
a hollow shaft;
a rotatable conduit extending through said hollow shaft, said rotatable conduit defining a longitudinal axis;
a scanning mechanism attached to said rotatable conduit at a location remote from a proximal end of said rotatable conduit, said scanning mechanism including a tiltable member configured for controlling a direction of an imaging beam emitted from said scanning mechanism, wherein said tiltable member is tiltable such that a tilt angle of said tiltable member is variable relative to the longitudinal axis;

an imaging angle encoder coupled to said scanning mechanism, wherein said imaging angle encoder is configured to produce a signal dependent on the tilt angle of said tiltable member; and a signal delivery channel connected to said imaging angle encoder and extending through said hollow shaft for delivering the signal dependent on the tilt angle to a proximal end of said hollow shaft;

wherein said imaging angle encoder is an optical imaging angle encoder configured to direct an incident optical beam onto a surface associated with said tiltable member and to receive a reflected optical beam from said surface, such that a change in the tilt angle of the tiltable member produces a corresponding change in the reflected optical beam; and wherein said imaging angle encoder includes one or both of a light source for producing the incident optical beam and an optical detector for detecting the reflected optical beam.

25. An imaging probe comprising:
a hollow shaft;
a rotatable conduit extending through said hollow shaft, said rotatable conduit defining a longitudinal axis;
a scanning mechanism attached to said rotatable conduit at a location remote from a proximal end of said rotatable conduit, said scanning mechanism including a tiltable member configured for controlling a direction of an imaging beam emitted from said scanning mechanism, wherein said tiltable member is tiltable such that a tilt angle of said tiltable member is variable relative to the longitudinal axis;

an imaging angle encoder coupled to said scanning mechanism, wherein said imaging angle encoder is configured to produce a signal dependent on the tilt angle of said tiltable member; and a signal delivery channel connected to said imaging angle encoder and extending through said hollow shaft for delivering the signal dependent on the tilt angle to a proximal end of said hollow shaft;

wherein said imaging angle encoder is an optical imaging angle encoder configured to direct an incident optical beam onto a surface associated with said tiltable member and to receive a reflected optical beam from said surface, such that a change in the tilt angle of the tiltable member produces a corresponding change in the reflected optical beam; and wherein said surface includes a variable thickness thin film.

26. An imaging probe comprising:

a hollow shaft;

a rotatable conduit extending through said hollow shaft, said rotatable conduit defining a longitudinal axis;

a scanning mechanism attached to said rotatable conduit at a location remote from a proximal end of said rotatable conduit, said scanning mechanism including a tiltable member configured for controlling a direction of an imaging beam emitted from said scanning mechanism, wherein said tiltable member is tiltable such that a tilt angle of said tiltable member is variable relative to the longitudinal axis;

an imaging angle encoder coupled to said scanning mechanism, wherein said imaging angle encoder is configured to produce a signal dependent on the tilt angle of said tiltable member; and a signal delivery channel connected to said imaging angle encoder and extending through said hollow shaft for delivering the signal dependent on the tilt angle to a proximal end of said hollow shaft;

wherein said imaging angle encoder is an optical imaging angle encoder configured to direct an incident optical beam onto a surface associated with said tiltable member and to receive a reflected optical beam from said surface, such that a change in the tilt angle of the tiltable member produces a corresponding change in the reflected optical beam; and wherein said surface includes a surface profile configured to produce a change in the intensity of the reflected optical beam in response to a change in the tilt angle of the tiltable member.

27. The imaging probe according to claim 26 wherein said surface profile is selected from the group consisting of polished, pigmented, marked, grated and textured.

28. An imaging probe comprising:

a hollow shaft;

a rotatable conduit extending through said hollow shaft, said rotatable conduit defining a longitudinal axis;

a scanning mechanism attached to said rotatable conduit at a location remote from a proximal end of said rotatable conduit, said scanning mechanism including a tiltable member configured for controlling a direction of an imaging beam emitted from said scanning mechanism, wherein said tiltable member is tiltable such that a tilt angle of said tiltable member is variable relative to the longitudinal axis;

an imaging angle encoder coupled to said scanning mechanism, wherein said imaging angle encoder is configured to produce a signal dependent on the tilt angle of said tiltable member; and a signal delivery channel connected to said imaging angle encoder and extending through said hollow shaft for delivering the signal dependent on the tilt angle to a proximal end of said hollow shaft;

wherein said imaging angle encoder is an optical imaging angle encoder configured to direct an incident optical beam onto a surface associated with said tiltable member and to receive a reflected optical beam from said surface, such that a change in the tilt angle of the tiltable member produces a corresponding change in the reflected optical beam; and wherein said signal delivery channel is a fiber optic suitable for optical coherence tomography, wherein said imaging angle encoder includes distal optical components for directing an incident optical coherence tomography beam onto a surface associated with said tiltable member and receiving a reflected optical coherence tomography beam from said surface, and wherein said optical imaging angle encoder is configured such that a path length of incident optical coherence tomography beam and the reflected optical coherence tomography beam is dependent on the tilt angle of the tiltable member.

29. An imaging probe comprising:

a hollow shaft;

a rotatable conduit extending through said hollow shaft, said rotatable conduit defining a longitudinal axis;

a scanning mechanism attached to said rotatable conduit at a location remote from a proximal end of said rotatable conduit, said scanning mechanism including a tiltable member configured for controlling a direction of an imaging beam emitted from said scanning mechanism, wherein said tiltable member is tiltable such that a tilt angle of said tiltable member is variable relative to the longitudinal axis;

an imaging angle encoder coupled to said scanning mechanism, wherein said imaging angle encoder is configured to produce a signal dependent on the tilt angle of said tiltable member; and a signal delivery channel connected to said imaging angle encoder and extending through said hollow shaft for delivering the signal dependent on the tilt angle to a proximal end of said hollow shaft;

wherein said imaging angle encoder is an ultrasonic imaging angle encoder including an imaging angle ultrasonic transducer, wherein said ultrasonic imaging angle encoder is configured to detect an acoustic reflection associated with tilt angle.

30. The imaging probe according to claim 29 wherein a frequency of said imaging angle ultrasonic transducer is between 20 and 120 MHz.

31. An imaging probe comprising:

a hollow shaft;

a rotatable conduit extending through said hollow shaft, said rotatable conduit defining a longitudinal axis;

a scanning mechanism attached to said rotatable conduit at a location remote from a proximal end of said rotatable conduit, said scanning mechanism including a tiltable member configured for controlling a direction of an imaging beam emitted from said scanning mechanism, wherein said tiltable member is tiltable such that a tilt angle of said tiltable member is variable relative to the longitudinal axis;

an imaging angle encoder coupled to said scanning mechanism, wherein said imaging angle encoder is configured to produce a signal dependent on the tilt angle of said tiltable member; and a signal delivery channel connected to said imaging angle encoder and extending through said hollow shaft for delivering the signal dependent on the tilt angle to a proximal end of said hollow shaft;

wherein said imaging angle encoder includes a strain gauge encoding mechanism.

32. An imaging probe comprising:

a hollow shaft;

a rotatable conduit extending through said hollow shaft, said rotatable conduit defining a longitudinal axis;

a scanning mechanism attached to said rotatable conduit at a location remote from a proximal end of said rotatable conduit, said scanning mechanism including a tiltable member configured for controlling a direction of an imaging beam emitted from said scanning mechanism, wherein said tiltable member is tiltable such that a tilt angle of said tiltable member is variable relative to the longitudinal axis;

an imaging angle encoder coupled to said scanning mechanism, wherein said imaging angle encoder is configured to produce a signal dependent on the tilt angle of said tiltable member; and a signal delivery channel connected to said imaging angle encoder and extending through said hollow shaft for delivering the signal dependent on the tilt angle to a proximal end of said hollow shaft;

wherein said imaging angle encoder includes an encoding mechanism selected from the group consisting of an electrically resistive encoding mechanism, a capacitive encoding mechanism, a magnetic encoding mechanism, and an inductive encoding mechanism.

33. An imaging probe comprising:

a hollow shaft;

a rotatable conduit extending through said hollow shaft, said rotatable conduit defining a longitudinal axis;

a scanning mechanism attached to said rotatable conduit at a location remote from a proximal end of said rotatable conduit, said scanning mechanism including a tiltable member configured for controlling a direction of an imaging beam emitted from said scanning mechanism, wherein said tiltable member is tiltable such that a tilt angle of said tiltable member is variable relative to the longitudinal axis;

an imaging angle encoder coupled to said scanning mechanism, wherein said imaging angle encoder is configured to produce a signal dependent on the tilt angle of said tiltable member; and a signal delivery channel connected to said imaging angle encoder and extending through said hollow shaft for delivering the signal dependent on the tilt angle to a proximal end of said hollow shaft;

wherein said tiltable member is mounted so that the tilt angle is variable by adjusting the angular velocity of said rotatable conduit.

34. The imaging probe according to claim 33 further comprising a restoring mechanism configured to apply a torque to said tiltable member for urging said tiltable member away from a preferred orientation.

35. An imaging probe comprising:

a hollow shaft;

a rotatable conduit extending through said hollow shaft, said rotatable conduit defining a longitudinal axis;

a scanning mechanism attached to said rotatable conduit at a location remote from a proximal end of said rotatable conduit, said scanning mechanism including a tiltable member configured for controlling a direction of an imaging beam emitted from said scanning mechanism, wherein said tiltable member is tiltable such that a tilt angle of said tiltable member is variable relative to the longitudinal axis;

an imaging angle encoder coupled to said scanning mechanism, wherein said imaging angle encoder is configured to produce a signal dependent on the tilt angle of said tiltable member; and a signal delivery channel connected to said imaging angle encoder and extending through said hollow shaft for delivering the signal dependent on the tilt angle to a proximal end of said hollow shaft;

wherein said imaging angle encoder is configured to receive reflected energy produced by a reflection of an imaging energy beam from a surface of said scanning mechanism, such that a change in the tilt angle of the tiltable member produces a corresponding change in the reflected energy.

36. An imaging probe comprising:

a hollow shaft;

a rotatable conduit extending through said hollow shaft, said rotatable conduit defining a longitudinal axis, wherein said rotatable conduit is connectable to a rotational drive mechanism for adjusting an angular velocity of said rotatable conduit about said longitudinal axis;

an imaging assembly attached to said rotatable conduit at a location remote from a proximal end of said rotatable conduit, said imaging assembly including a movable member for delivering an energy beam along an energy beam path from said movable member out of said hollow shaft at a variable imaging angle with respect to said longitudinal axis of said rotatable conduit, wherein said movable member is mounted so that the variable imaging angle between the energy beam path and said longitudinal axis of said rotatable conduit is varied by adjusting the angular velocity of said rotatable conduit; and a restoring mechanism configured to apply a torque to said movable member for urging said movable member away from a preferred orientation.

37. A scanning device for emitting or receiving an energy beam during rotary motion, comprising:

a rotary component having a rotary axis, wherein said rotary component is connectable to a rotary drive mechanism;

an energy emitting or receiving device coupled to said rotary component, wherein said energy emitting or receiving device is configured to emit or receive the energy beam;

a movable member configured such that the energy beam is emitted or received along an energy beam path at a variable angle with respect to said rotary axis of said rotary component, wherein said movable member is coupled to said rotary component such that the variable angle between the energy beam path and the rotary axis of said rotary component is varied by adjusting the angular velocity of said rotary component; and a restoring mechanism configured to apply a torque to said movable member for urging said movable member away from a preferred orientation.

* * * * *